United States Patent [19]

Summerton et al.

[11] Patent Number: 5,506,337
[45] Date of Patent: Apr. 9, 1996

[54] MORPHOLINO-SUBUNIT COMBINATORIAL LIBRARY AND METHOD

[75] Inventors: James E. Summerton; Dwight D. Weller, both of Corvallis, Oreg.

[73] Assignee: Antivirals Inc., Corvallis, Oreg.

[21] Appl. No.: 242,159

[22] Filed: May 11, 1994

Related U.S. Application Data

[63] Continuation-in-part of Ser. No. 15,211, Feb. 9, 1993, which is a continuation-in-part of Ser. No. 988,895, Dec. 10, 1992, abandoned, which is a continuation of Ser. No. 799,681, Nov. 21, 1991, Pat. No. 5,185,444, which is a continuation of Ser. No. 454,057, Dec. 20, 1989, abandoned, which is a continuation-in-part of Ser. No. 100,033, Sep. 23, 1987, Pat. No. 5,142,047, which is a continuation-in-part of Ser. No. 944,707, Dec. 18, 1986, Pat. No. 5,217,866, which is a continuation-in-part of Ser. No. 911,258, Sep. 24, 1986, abandoned, which is a continuation-in-part of Ser. No. 712,396, Mar. 15, 1985, abandoned, and a continuation of Ser. No. 979,158, Nov. 23, 1992, Pat. No. 5,405,938, which is a continuation-in-part of Ser. No. 719,732, Feb. 9, 1993, Pat. No. 5,166,315, which is a continuation-in-part of Ser. No. 454,055, Dec. 20, 1989, Pat. No. 5,034,506.

[51] Int. Cl.$^6$ ............ C07D 413/12; C07D 413/14; C08G 59/00; C08G 65/00
[52] U.S. Cl. ............ 528/391; 528/398; 528/399; 528/403; 528/405; 528/406; 528/422; 528/423; 528/425
[58] Field of Search .................... 528/391, 398, 528/399, 403, 405, 406, 422, 423, 425

[56] References Cited

U.S. PATENT DOCUMENTS

| 5,034,506 | 7/1991 | Summerton et al. | 528/391 |
|---|---|---|---|
| 5,166,315 | 11/1992 | Summerton et al. | 528/406 |
| 5,182,366 | 1/1993 | Huebner et al. | 530/334 |
| 5,185,444 | 2/1993 | Summerton et al. | 544/81 |
| 5,266,684 | 11/1993 | Rutter et al. | 530/334 |

OTHER PUBLICATIONS

Barbas, C. F. III, et al., "Semisynthetic combinatorial antibody libraries: A chemical solution to the diversity problem," *Proc. Natl. Acad. Sci. USA* 89: 4457–4461 (1992).

Brummel, C., et al., "A Mass Spectrometric Solution to the Address Problem of Combinatorial Libraries," *Science* 264: 399–402 (1994).

Dooley, C. T., et al., "Acetalins: Opioid receptor antagonists determined through the use of synthetic peptide combinatorial libraries," *Proc. Natl. Acad. Sci. USA* 90: 10811–10815 (1993).

Dooley, C. T., and R. A. Houghten, "The use of positional scanning synthetic peptide combinatorial libraries for the rapid determination of opioid receptor ligands," *Life Sciences* 52(18): 1509–1517 (1993).

Ecker, D. J., et al., "Rational screening of oligonucleotide combinatorial libraries for drug discovery," *Nucleic Acids Research* 21(8): 1853–1856 (1993).

Eichler, J., and R. A. Houghten, "Identification of Substrate--Analog Trypsin Inhibitors through the Screening of Synthetic Peptide Combinatorial Libraries," *Biochemistry* 32: 11035–11041 (1993).

Fodor, S. P. A., et al., "Light–Directed, Spatially Addressable Parallel Chemical Synthesis," *Science* 251: 767–773 (1991).

Houghten, R. A., et al., "Generation and use of synthetic peptide combinatorial libraries for basic research and drug discovery," *Nature* 354: 84–86 (1991).

Houghten, R. A., "Finding the needle in the haystack," *Current Biology* 4(6): 564–567 (1994).

Lam, K. S., et al., "A new type of synthetic peptide library for identifying ligand–binding activity," *Nature* 354: 82–84 (1991).

Needels, M. C., et al., "Generation and screening of an oligonucleotide–encoded synthetic peptide library," *Proc. Natl. Acad. Sci. USA* 90: 10700–10704 (1993).

Pinilla, C., et al., "Synthetic peptide combinatorial libraries (SPCLs): identification of the antigenic determinant of β–endorphin recognized by monoclonal antibody 3E7," *Gene* 138: 71–76 (1993).

*Primary Examiner*—Nathan M. Nutter
*Attorney, Agent, or Firm*—Charles K. Sholtz; Peter J. Dehlinger

[57] ABSTRACT

A method of generating a compound capable of interacting specifically with a selected macromolecular ligand is disclosed. The method involves contacting the ligand with a combinatorial library of oligomers composed of morpholino subunits with a variety of nucleobase and non-nucleobase side chains. Oligomer molecules that bind specifically to the receptor are isolated and their sequence of base moieties is determined. Also disclosed is a combinatorial library of oligomers useful in the method and novel morpholino-subunit polymer compositions.

14 Claims, 23 Drawing Sheets

1

2

3

4

5

6

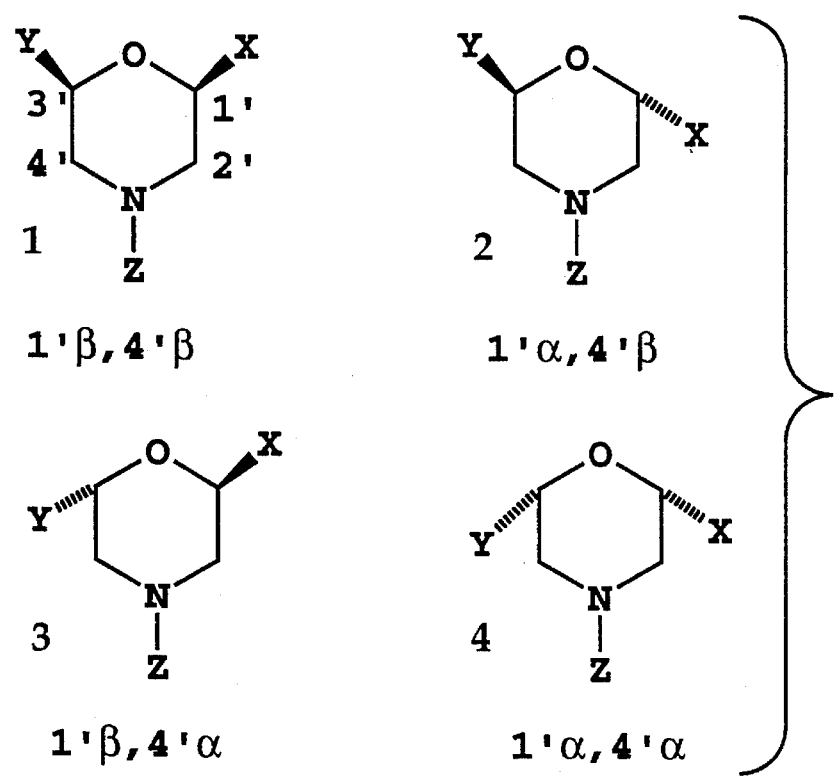
Fig. 6
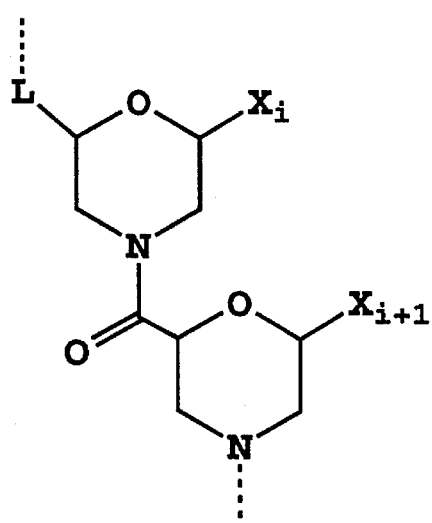
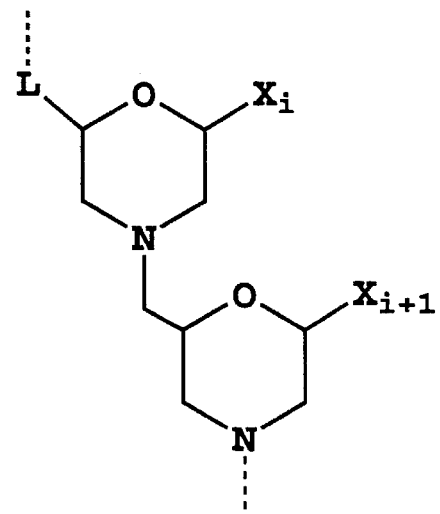
Fig. 12A          Fig. 12B

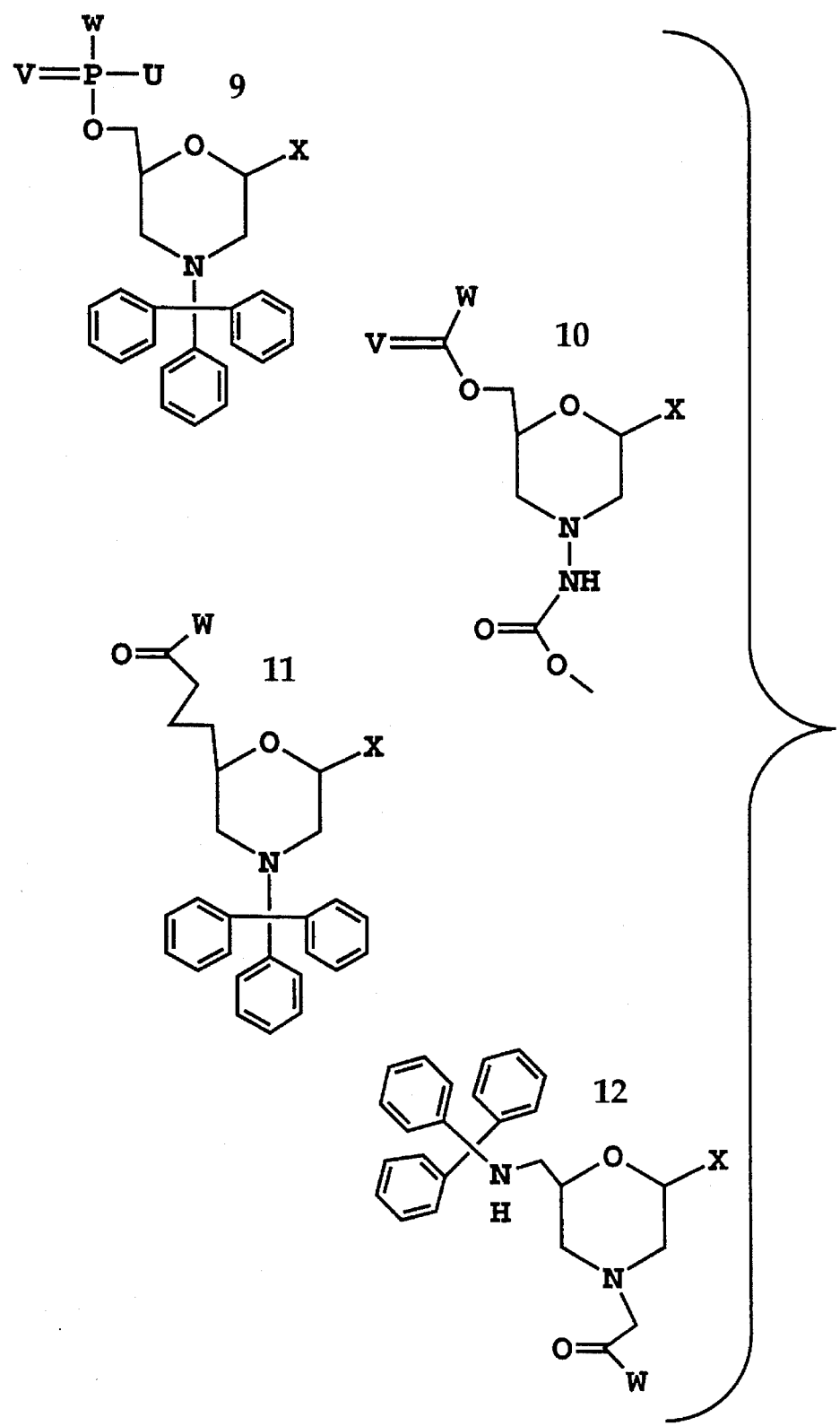
Fig. 7 con't

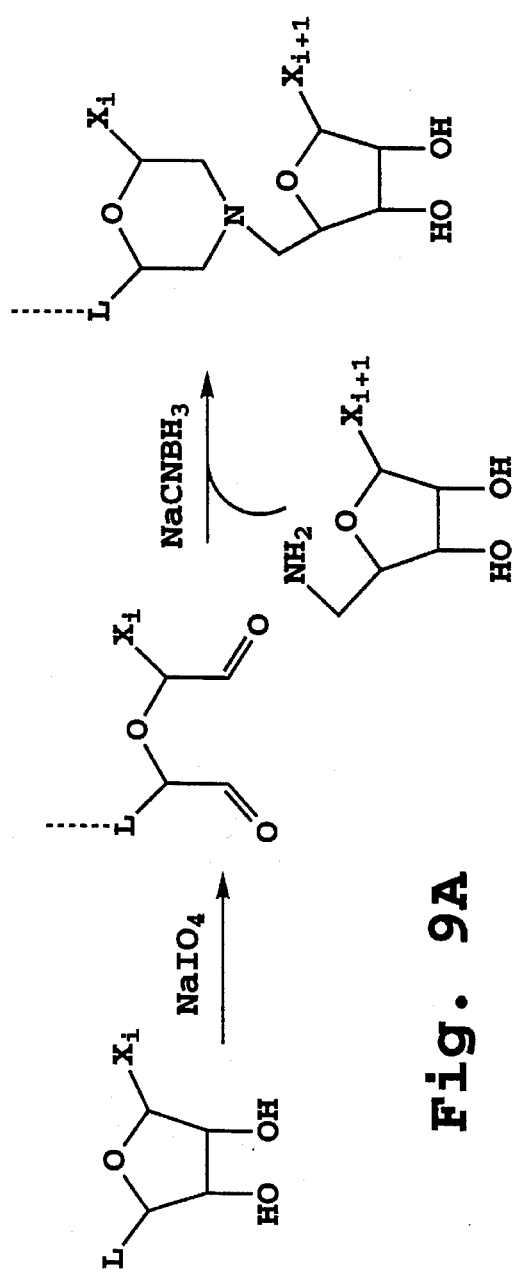
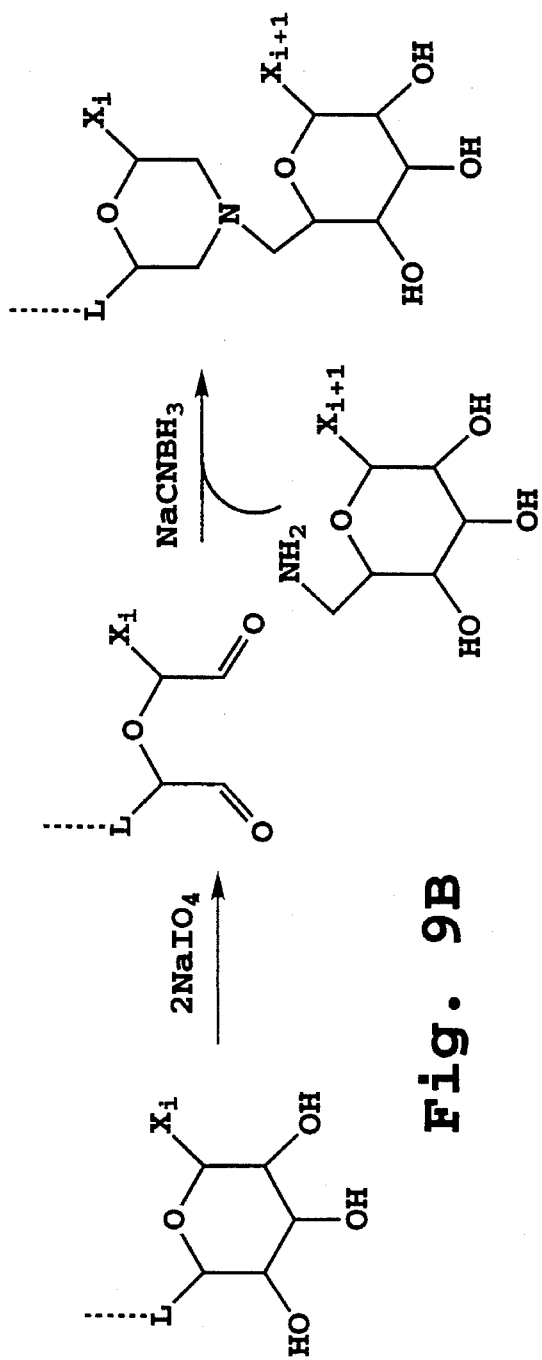
Fig. 9A
Fig. 9B

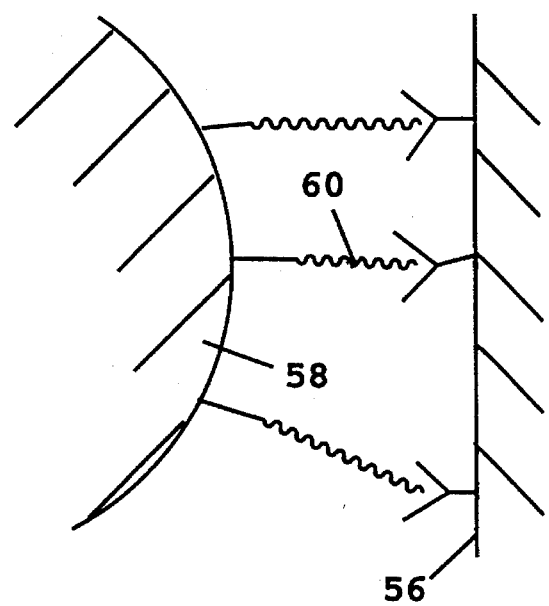
Fig. 22
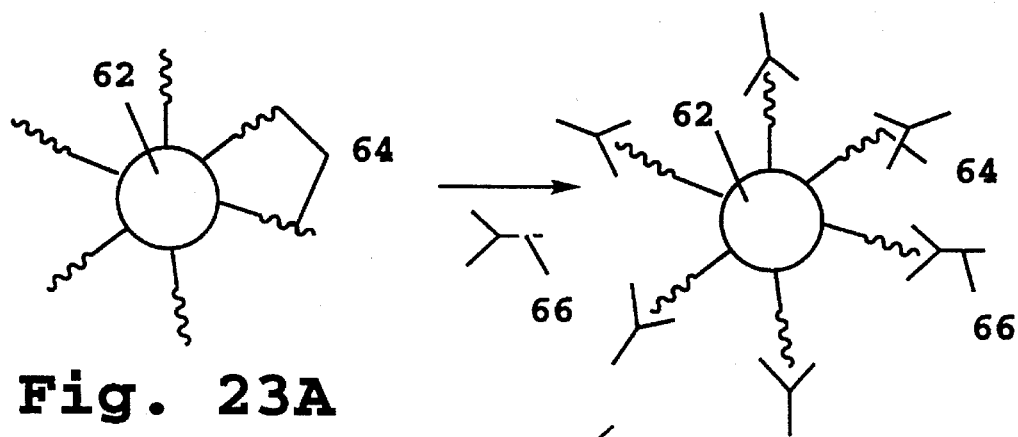
Fig. 23A
Fig. 23B
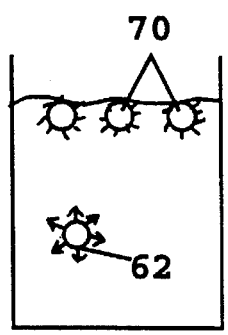
Fig. 23D
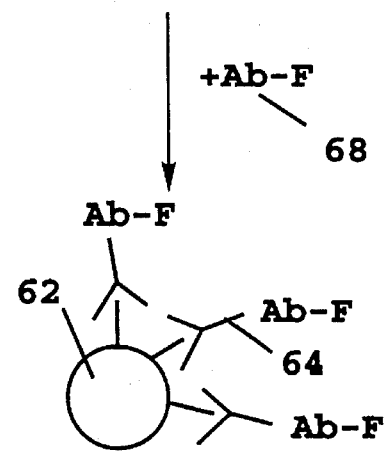
Fig. 23C

MORPHOLINO-SUBUNIT COMBINATORIAL LIBRARY AND METHOD

This application is a continuation-in-part of co-owned U.S. patent application Ser. No. 08/015,211 filed Feb. 9, 1993, which is a continuation-in-part of co-owned U.S. patent application Ser. No. 07/988,895 filed Dec. 10, 1992 (now abandoned), which is a continuation of co-owned U.S. patent application Ser. No. 07/799,681 filed Nov. 21, 1991 (now U.S. Pat. No. 5,185,444, incorporated by reference herein), which is a continuation of co-owned U.S. patent application Ser. No. 07/454,057 filed Dec. 20, 1989 (now abandoned), which is a continuation-in-part of co-owned U.S. patent application Ser. No. 07/100,033 filed Sep. 23, 1987 (now U.S. Pat. No. 5,142,047, incorporated by reference herein), which is a continuation-in-part of co-owned U.S. patent application Ser. No. 06/944,707 filed Dec. 18, 1986 (now U.S. Pat. No. 5,217,866, incorporated by reference herein), which is a continuation in part of co-owned U.S. patent application Ser. No. 06/911,258 filed Sep. 24, 1986 (now abandoned), which is a continuation-in-part of co-owned U.S. patent application Ser. No. 06/712,396 filed Mar. 15, 1985 (now abandoned), and a continuation of co-owned U.S. patent application Ser. No. 07/979,158 filed Nov. 23, 1992, now U.S. Pat. No. 5,405,938, which is a continuation-in-part of co-owned U.S. patent application Ser. No. 07/719,732 filed Feb. 9, 1993 (now U.S. Pat. No. 5,166,315, incorporated by reference herein), which is a continuation-in-part of co-owned U.S. patent application Ser. No. 07/454,055 filed Dec. 20, 1989 (now U.S. Pat. No. 5,034,506, incorporated by reference herein).

FIELD OF THE INVENTION

The present invention relates to a combinatorial library formed by sequences of morpholino subunit structures, and to a method of generating novel binding compounds using the library.

REFERENCES

Adlington, et al., *J. Chem. Soc., Chem. Commun.* 944 (1983).

Barbas, C. F., et al., *Proc Nat Acad Sci, USA*, 89(10):4457 (1992).

Dooley, C. T., et al., *Proc Nat Acad Sci, USA*, 90(22):10811 (1993a).

Dooley, C. T., et al., *Life Sci*, 52 (18): 1509 (1993 b).

Ecker, D. J., et al., *Nuc Acids Res*, 21(8):1853 (1993).

Eichler, J, et al., *Biochemistry*, 32 (41): 11035 (1993).

Fodor, S. P., et al., *Science* 251:767–773 (1991).

Furka, A., et al., *14th International Congress on Biochemistry* 5:47, Prague, Czechoslovakia, Jul. 10–15, 1988a.

Furka, A., et al., *10th International Congress on Biochemistry* 5:288, Prague, Czechoslovakia, Aug. 15–19, 1988b.

Furka, A., et al., *Int. J. Pept. Protein Res.* 37:487–493 (1991).

Houghten, R. A., et al., *NIDA Res Monograph*, 134:66 (1993 a).

Houghten, R. A.; *Gene*, 137(1):7 (1993b).

Houghten, R. A., and Dooley, C. T., *Bioorg. Med. Chem. Lett.* 3:405–412 (1993c).

Houghten, R. A., et al., *Biotechniques*, 13(3):412 (1992).

Houghten, R. A., et al., *Nature (London)* 354: 84–86 (1991).

Jung, G., and Beck-Sickinger, A. G., *Angew. Chem. Int. Ed. Eng.* 31:367–383 (1992).

Koppel and Robins, *J. Org. Chem.* 23:1459 (1958).

Kramer, A., et al., *Pept Res*, 6(6): 314 (1993).

Lam, K. S., et al., *Nature (London)* 354: 82–84 (1991).

Lam, K. S., et al., *Bioorg. Med. Chem. Lett.* 3:419–424 (1993).

Ohlmayer, M. H., et al., *Proc Nat Acad Sci, USA*, 90(23):10922 (1993).

Pavia, M. R., et al., *Bioorg. Med. Chem. Lett.* 3:387–383 (1993).

Pinilla, C., et al., *Gene*, 128(1):71 (1993).

Pinilla, C., et al., *Biotechniques*, 13(6):901 (1992).

Sebestyen, F., et al., *Bioorg. Med. Chem. Lett.* 3:413–418 (1993).

Zuckermann, R. N., et al., *Int. J. Pept. Protein Res.* 40:498–507 (1992).

BACKGROUND OF THE INVENTION

There is current widespread interest in using combinatorial libraries of random-sequence oligonucleotides, polypeptides, or synthetic oligomers to search for biologically active compounds (Kramer; Houghten, 1993a–1993c, 1992, 1991; Ohlmeyer; Dooley, 1993a–1993b; Eichler; Pinella, 1993, 1992; Ecker; and Barbas). Ligands discovered by screening libraries of this type may be useful in mimicking or blocking natural ligands, or interfering with the naturally occurring interactions of a biological target. They can also provide a starting point for developing related molecules with more desirable properties, e.g., higher binding affinity.

Combinatorial libraries of the type useful in this general application may be formed by a variety of solution-phase or solid-phase methods in which mixtures of different subunits are added stepwise to growing oligomers, until a desired oligomer size is reached. A library of increasing complexity can be formed in this manner, for example, by pooling multiple choices of reagents with each additional subunit step (Houghten, 1991; 1993c).

Alternatively, the library may be formed by solid-phase synthetic methods in which beads containing different-sequence oligomers that form the library are alternately mixed and separated, with one of a selected number of subunits being added to each group of separated beads at each step. An advantage of this method is that each bead contains only one oligomer specie, allowing the beads themselves to be used for oligomer screening (Furka, 1991; Lam, 1991, 1993; Zuckermann; Sebestyn).

Still another approach that has been suggested involves the synthesis of a combinatorial library on spatially segregated arrays (Fodor). This approach is generally limited in the number of different library sequences that can be generated.

Since the chance of finding useful ligands increases with the size of the combinatorial library, it is desirable to generate libraries composed of large numbers of different-sequence oligomers. In the case of oligonucleotides, for example, a library having 4-base variability at 8 oligomer residue positions will contain as many as $4^8$ (65,536) different sequences. In the case of a polypeptides, a library having 20-amino acid variability at six residue positions will contain as many as $20^6$ (64,000,000) different species.

Because each different-sequence specie in a large-number library may present in small amounts, one of the challenges in the combinatorial library selection procedure is isolating and determining the sequence of specie(s) that have the desired binding or other selected properties.

Where the combinatorial library consists of oligonucleotides, this problem may be solved by amplifying the isolated sequence, e.g., by polymerase chain reaction methods. In the case of polypeptide libraries, other methods must be employed. In one approach, where the library has been formed by pooling multiple choices of reagents during synthesis, a pool which is shown to have desired properties is resynthesized iteratively with lower and lower complexity until a single sequence compound is identified.

Where the library oligomers have been formed on beads, and each bead represents one oligomeric specie, it may be possible to conduct microscale sequencing on the oligomers contained on a single isolated bead.

In another approach, the library sequences, e.g., random peptide sequences, are cosynthesized with a sequenceable tag, e.g., an oligonucleotide sequence, attached to the library sequence oligomer. That is, each oligomer in the library is associated with a distinctive sequencecable tag. Once an oligomer with the desired selection properties is identified, its sequence can be determined by determining the corresponding sequence of the sequenecable tag (Brenner; Kerr).

A related approach has been to construct combinatorial libraries on beads that are themselves tagged with distinctive tagging molecules at each successive step in oligomer synthesis. Once an oligomer with desired binding properties is identified, the bead to which the oligomer is attached can be "read" to identify the oligomer sequence in terms of a sequence of tagging molecules (Ohlmeyer).

Another basic consideration in the generation of desired compounds by screening combinatorial libraries is the nature of the selected compound itself. Polynucleotide libraries are relatively easy to generate and can sequenced at low concentrations, but have two basic disadvantages. First, the molecular variation in the library is limited by the relatively few bases that are employed, typically the standard four bases/oligomer position. Secondly, even if an active compound is identified, the compound may have pharmacological limitations due to its susceptibility to nuclease digestion.

In the case of polypeptide libraries, these also can be synthesized readily by known solution or solid-phase methods, and the possibility of 20 (or more) different side chains at each oligomer position greatly expands the potential variability of the library. However, as indicated above, screened polypeptides may be relatively difficult to sequence at the low oligomer concentrations that are likely to be present. Further, polypeptide compounds may be susceptible to protease digestion in vivo.

Ideally, then, a combinatorial library should be easy to synthesis by stepwise solution-phase or solid-phase methods, should allow for a large number of different subunits at each residue position, should provide a broad range of structural diversity, and should be readily sequenceable, once a library oligomer with desired binding or other screened property is identified, and should be generally stable in living systems.

SUMMARY OF THE INVENTION

The invention includes, in one aspect, a combinatorial library of non-biological oligomers formed predominantly of morpholino subunit structures of the form:

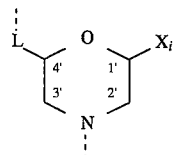

where (i) the structures are linked together by linkages "L" one to four atoms long joining the morpholino nitrogen of one subunit structure to the 4' cyclic carbon of an adjacent subunit structure, and $X_i$ is a purine or pyrimidine side chain, a non-nucleobase aromatic side chain, an aliphatic side chain, and/or a mixed aromatic/aliphatic side chain. At least 3 of the side chains $X_i$ are variable, and the library includes at least about 1,000 different side chain sequence oligomers.

In one general embodiment, the oligomer bases in the library include a combination of nucleobase side chains, i.e., purines and/or pyrimidines, and non-nucleobase side chains, such as non-nucleobase aromatic side chains, aliphatic side chains, and mixed aromatic/aliphatic side chains.

In another general embodiment, the oligomers are effective to hybridize, by Watson-Crick base pairing, to one of the oligonucleotide oligomers in combinatorial library of random sequence oligonucleotides.

The oligomers in the library may also have different sequences of linkages, or be composed of the same linkages.

One preferred linkage is a 3-atom carbamate or 3-atom phosphorodiamidate linkage.

The oligomers may also include branched structures, in which one or more of the subunit structures forming an oligomer is linked to multiple subunits.

The oligomers in the library may be formed on a plurality of particles, such as macroporous particles, where each particle has a surface coating of molecules containing one of the base-sequences in the library. The oligomer molecules are preferably attached to the particle through cleavable linkages, e.g., chemically or photolytically cleavable linkages.

Alternatively, or in addition, the particles may be macroreticular particles having selected sizes in the 40–200 μm range, where the oligomers are coupled to the particles through cleavable linkages.

Alternatively, or in addition, the oligomer molecules on each particle may represent a family of different-length oligomers having a common sequence from one oligomer end, but different termination subunit structures at the opposite oligomer end.

In another aspect, the invention includes a method of generating an oligomer compound capable of interacting specifically with a selected macromolecular ligand. The method includes contacting the receptor with a combinatorial library of oligomers of the type described above, isolating oligomer molecules that binds specifically to the receptor, and determining the sequence of bases in the isolated oligomer molecules.

Where the oligomers are designed to hybridize, by Watson-Crick base pairing, to complementary-sequence oligonucleotides in a combinatorial oligonucleotide library, the determining step includes reacting the isolated oligomers with a combinatorial library of oligonucleotides, under conditions effective to produce hybridization between the isolated oligomer molecules and complementary-base oligonucleotides, and determining the sequence of the oligonucleotides hybridized to the isolated oligomer molecules.

Where the combinatorial library is formed on a plurality of particles, the particle containing the desired binding molecules is isolated, e.g., by binding to a solid support, and oligomers on the particles are then sequenced, e.g., by release of the oligomers and micro mass spectrometry of the released oligomers.

Alternatively, particle(s) having surface-bound receptor may be identified by reacting the particles with fluorescent-labeled anti-receptor antibodies, or by exploiting the greater density of the particles with surface-bound receptor.

Also disclosed is a polymer composition assembled predominantly of morpholino subunit structures of the form:

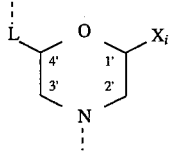

where (i) the structures are linked together by linkages one to four atoms long joining the morpholino nitrogen of one subunit structure to the 4' cyclic carbon of an adjacent subunit structure, and $X_i$ is a purine or pyrimidine side chain, a non-nucleobase aromatic side chain, an aliphatic side chain, and/or a mixed aromatic/aliphatic side chain.

In a related aspect, the invention includes polymer composition assembled predominantly from morpholino subunit structures of the form: where (i) the structures are linked together by linkages one to four atoms long joining the morpholino nitrogen of one subunit structure to the 4' cyclic carbon of an adjacent subunit structure, and $X_i$ is a purine or pyrimidine side chain, a non-nucleobase aromatic side chain, an aliphatic side chain, and/or a mixed aromatic/aliphatic side chain.

These and other objects and features of the invention will become more fully appreciated when the following detailed description of the invention is read in conjunction with the accompanying drawings.

BRIEF DESCRIPTION OF THE DRAWINGS

FIG. 6 shows stereochemical options for $X_i$ and linkage atoms Y in a morpholino subunit structure;

FIGS. 9A and 9B illustrate methods for the conversion of ribose and glucose compounds, respectively, to morpholino subunit structures during oligomer assembly;

FIGS. 12A and 12B show representative one-atom linkages in oligomers of the invention;

FIG. 22 illustrates a solid-phase method for isolating a particle carrying a surface coating of oligomer molecules that bind to a receptor attached to a solid support; and FIGS. 23A–23D illustrate various solution-phase methods for selecting particles carrying a surface coating of oligomer molecules that bind to a receptor attached to a solid support (23A), by first binding receptor to a particle having the desired oligomer sequence (23B), and identifying particle(s) having bound receptor by further reacting the particle with fluorescent-labeled anti-receptor antibody (23C), or by separating particle with bound receptor on the basis of its increased density (23D).

DETAILED DESCRIPTION OF THE INVENTION

I. Definitions

Figure 1:
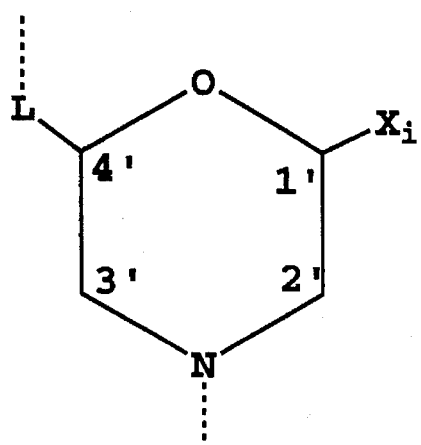
FIG. 1 shows a subunit of an oligomer formed of morpholino subunit structures joined by linkages L.

Unless otherwise stated, the terms below have the following meanings:

A "morpholino subunit structure" refers to a morpholino structure of the form:

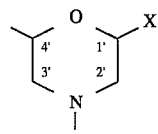

where $X_i$ is a side chain.

A "side chain" refers to one of several different X-groups that may be carried on a morpholino subunit structure.

A "subunit" in an oligomer includes a subunit structure and one of its associated linkages to an adjacent subunit structure. That is, the oligomer is composed of linked subunits, which in turn are composed of subunit structures and associated linkages.

An "oligomer" refers to a polymer composed of typically between about 4–15 subunits. The oligomers of the present inventions are formed of morpholino subunit structures that are linked together by linkages of one to four atoms long joining the morpholino nitrogen of one subunit structure to the 4' cyclic carbon of an adjacent subunit structure. Although morpholino subunit structures are the predominant subunit form in the oligomers, other subunit structures may also be employed.

The "sequence of side chains" in an oligomer refers to the sequence of individual side chains on successive subunit structures in an oligomer, on progressing from one end of the oligomer to the other.

The "sequence of linkages" in an oligomer refers to the sequence of individual linkages linking successive subunit structures in an oligomer, on progressing from one end of the oligomer to the other.

A "combinatorial library of oligomers" refers to a library of oligomer molecules containing a large number, typically between $10^3$ and $10^7$ different-sequence oligomers, typically defined by a different sequence of side chains, or a combination of different sequences of side chains and linkages. Each sequence in a library is preferably represented by a plurality, e.g., $10^{10}$–$10^{12}$ molecules of the same sequence.

A "branched oligomer" refers to an oligomer having one or more morpholino subunit structures that are covalently attached to a linkage that itself directly links two additional morpholino subunit structures in the oligomer. The sequence of side chains in a branched oligomer refers to the sequence of side chains in the longest chain of the oligomer, with branched side chains being indicated in parenthesis at the linkage position to which the branch is joined. Thus, an oligomer sequence of the form: $X_1X_2X_3X_4(X_{4-1}X_{4-2})X_5X_6$ refers to an eightmer having the linear sequence of sidchains $X_1X_2X_3X_4X_5X_6$, and a branched sequence of side chains $X_{4-1}X_{4-2}$ on a two-subunit chain attached to the linkage between the fourth and fifth subunit structures in the linear chain.

A "nucleobase" side chain is a purine or pyrimidine side chain attached to the morpholino moiety through the N9 of the purine or the N1 of the pyrimidine.

A "non-nucleobase aromatic" side chain is a substituted or unsubstituted aromatic side chain that is not a purine or pyrimidine.

An "aliphatic" side chain refers to a side chain having the general structure —$(CH_2)_m$—X where m=1–5 and X is H, an unbranched or branched alkane, alkene or alkyne, OH, SH, an amine, a halide, an aldehyde, an acid, an amide, or an ester group.

A "mixed aromatic/aliphatic" side chain is an aromatic side chain substituted with an aliphatic side chain.

A "receptor" is a macromolecule capable of specifically interacting with ligand molecule, including oligomers of the inventions. Binding of the ligand to the receptor is typically characterized by a high binding affinity i.e., $K_m > 10^5$ and is intended to affect, e.g., inhibit, the function of the receptor in its normal biological setting. The receptor is also referred to herein as a target structure.

II. Morpholino Subunit Structures

Figure 2:
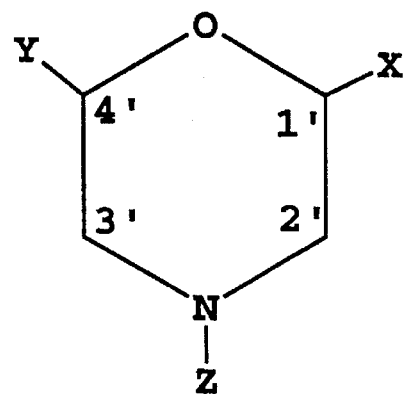
FIG. 2 shows a morpholino subunit structure used in the FIG. 1 oligomer.

The invention includes, in one aspect, a combinatorial library of oligomers having the general form shown in FIG. 1. The oligomers are formed from morpholino subunit structures of the form shown in FIG. 2, where the subunit structures are linked together by linkages L one to four atoms long joining the morpholino nitrogen of one subunit structure to the 4' cyclic carbon of an adjacent subunit structure. The $X_i$ groups or side chains in the oligomers are nucleobase or non-nucleobase X groups, as will be described below.

Each morpholino subunit structure contains a morpholino backbone moiety, which allows linking the subunit structure to other subunit structures in a defined order, and a side chain $X^i$. These morpholino subunit structures have the general structure shown in FIG. 2, where $X^i$, the side chain, is hydrogen or an organic substituent, which may be in a protected form; Y, which may be in an activated or protected form, is a group which allows coupling of the morpholino subunit to the morpholino nitrogen or Z group of another morpholino subunit, or other structure; Z is hydrogen, a protective group, or other group, which may be in an activated or protected form, which is suitable for coupling to the Y group of another morpholino subunit or other structure; and, X and Y substituents have defined stereochemical orientations.

A. Preparing Subunit Structures

Figure 3:
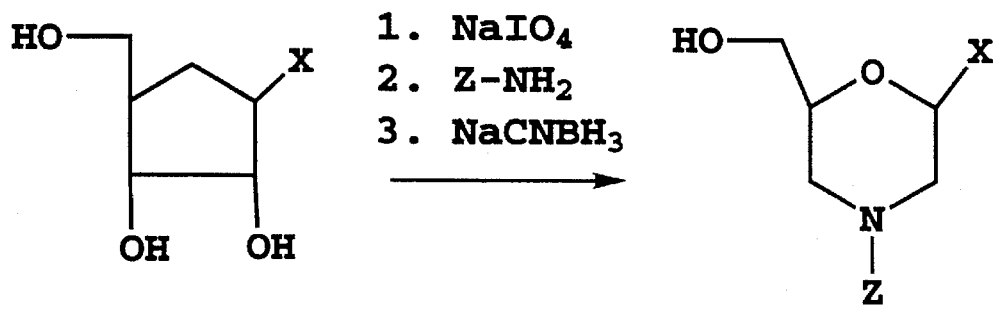
FIG. 3 illustrates the conversion of a ribonucleotide to a morpholino subunit structure.
Figure 4:
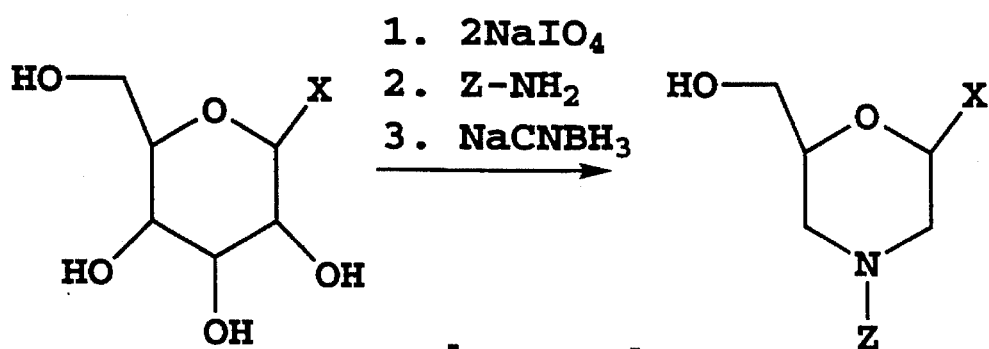
FIG. 4 shows the conversion of glucose to a morpholino subunit structure.

Morpholino subunit structures can be prepared from ribonucleosides and related substituted furanosides, as illustrated in FIG. 3 and described in Example 1, and from substituted glucose and related hexopyranosides, as illustrated in FIG. 4 and described in Example 2.

Figure 5A:
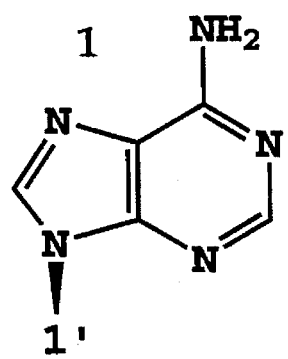
FIGS. 5A–5E shows representative $X_i$ purine and pyrimidine nucleobase side chains (3A), modified nucleobase side chains (3B); aromatic side chains (3C), aliphatic side chains (3D, and mixed aromatic/aliphatic side chains (3E), where the $X_i$ side chains are shown attached to the 1' morpholino ring position in FIG. 1.
Figure 5A:
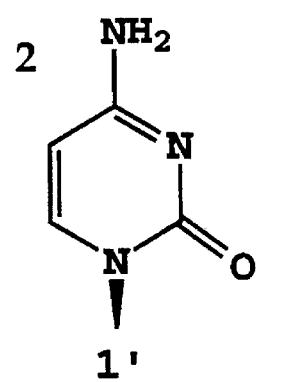
Figure 5A:
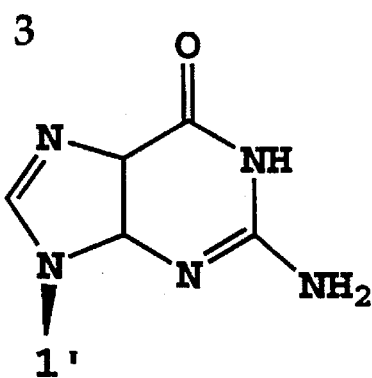
Figure 5A:
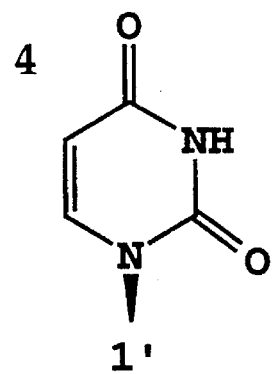
Figure 5A:
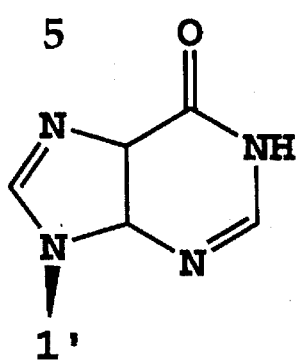
Figure 5A:
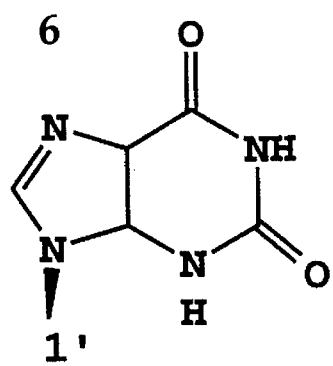

A variety of side chains, X, contribute to the structural diversity achievable with this class of oligomers, which in turn facilitates the selection of oligomer species with desirable biological activities. FIGS. 5A–5E illustrate representative types of side chains of morpholino subunits which can be prepared from natural products and simple chemical reagents. FIG. 5A shows representative nucleobase side chains. Example 3 describes synthetic routes to such structures.

Figure 5B:
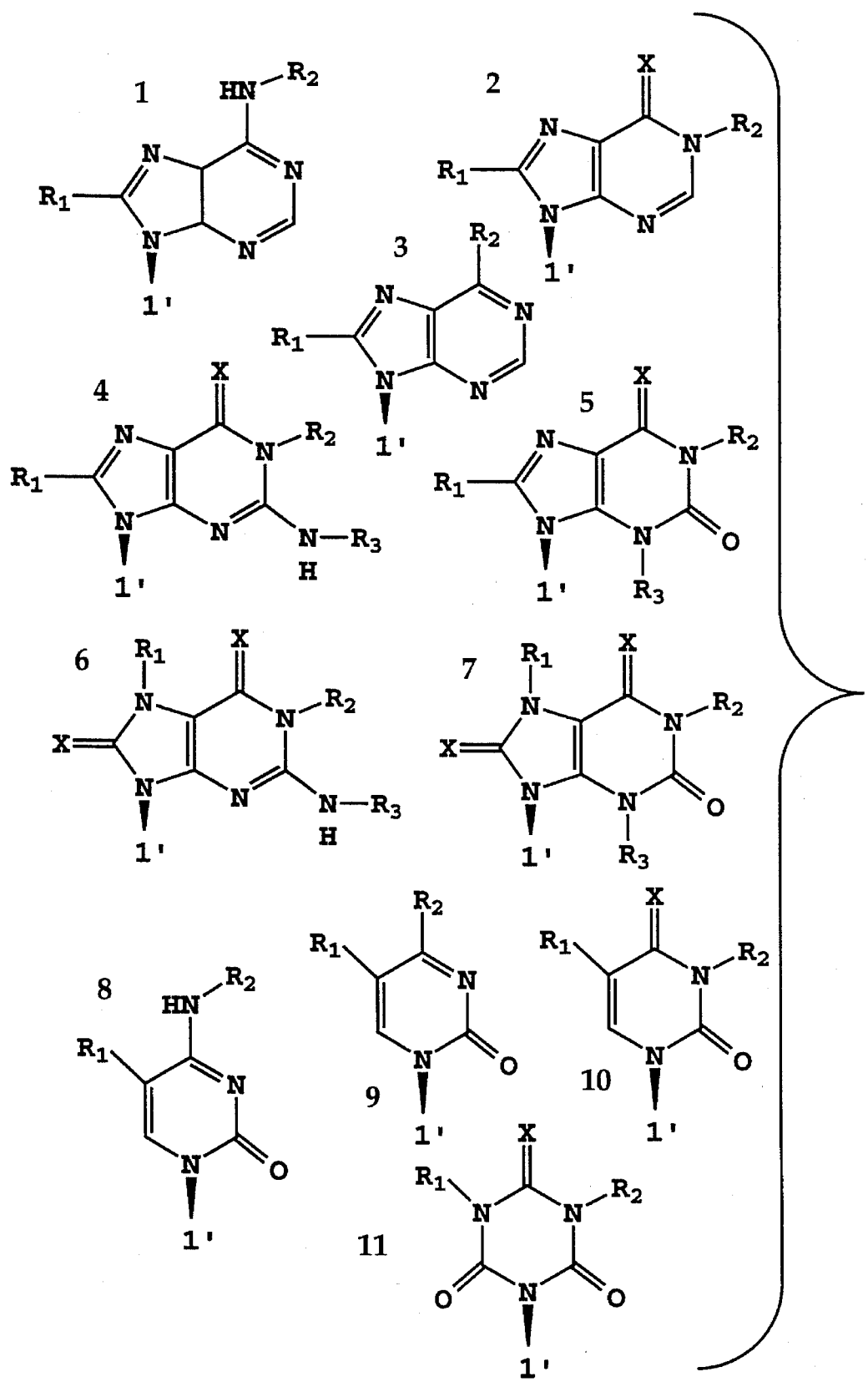

FIG. 5B shows a number of modified nucleobase side chains modified by addition of R groups at various ring positions, as indicated. Here R is preferably an aliphatic group, such as methyl. Example 4 describes synthetic routes to nucleobases modified at one or more such sites.

Figure 5C:
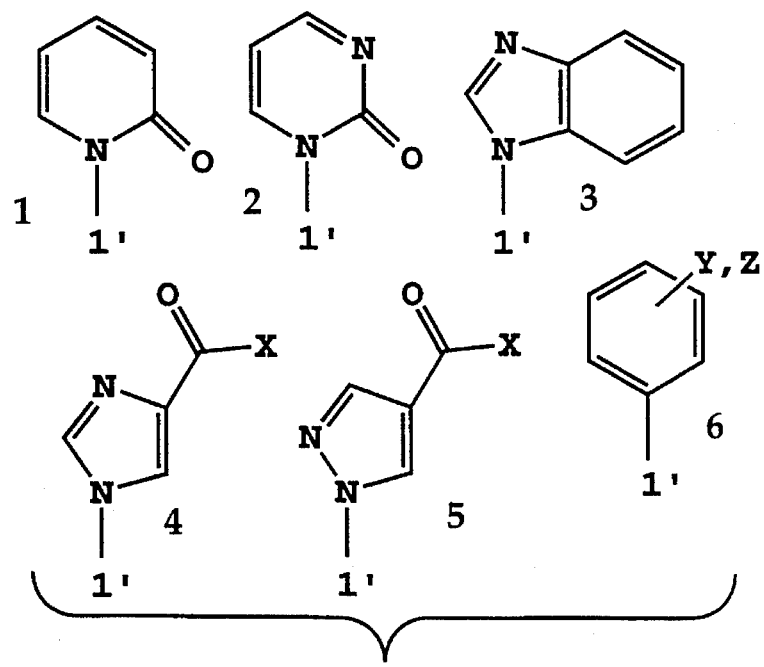

FIG. 5C shows representative, aromatic, non-nucleobase side chains. Here X is OH or OR, where R is a lower alkyl, or a primary, secondary or tertiary amine. Y and Z may be any of a variety of small groups, such as CN, halogen, $NO_2$, OH, alkoxy, aldehyde, and amine groups. Examples 5A–5E disclose methods for preparing morpholino subunit structures with exemplary non-nucleobase aromatic side chains.

Figure 5D:
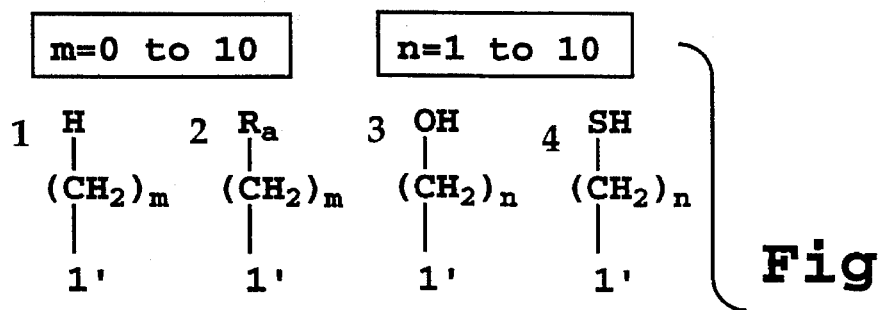
Figure 5E:
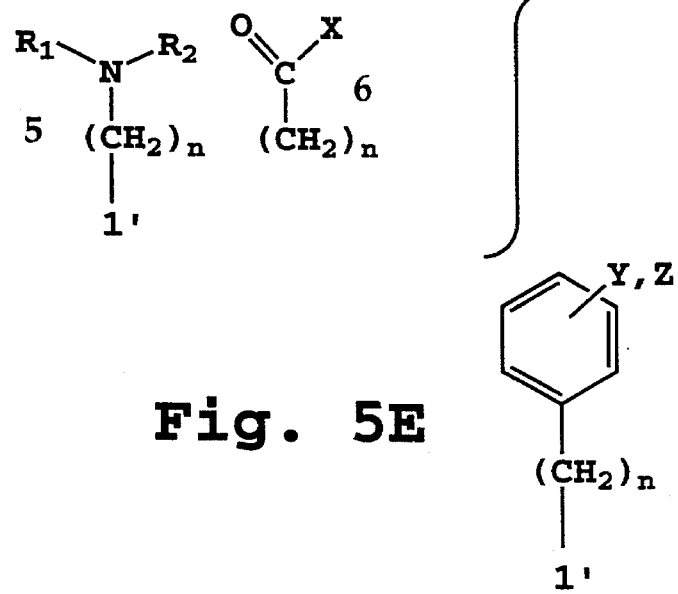

Also contemplated are morpholino subunit structures with aliphatic side chains, as shown in FIG. 5D, where the R groups may be branched or unbranched alkanes, alkenes, or alkynes. Exemplary morpholino subunits having these types of side chains are described in Examples 5F–5I. Finally, the side chains may be mixed aromatic/aliphatic groups, such as shown in FIG. 5E.

B. Stereochemical Control of X and Y

The stereochemistry of the X side chain about the 1' carbon of the morpholino moiety can be selected to be either alpha or beta, and the stereochemistry of the Y group about the 4' carbon of the morpholino moiety can also be selected to be either alpha or beta, as illustrated in FIG. 6. Basic synthetic strategies for achieving these selected stereochemical options are illustrated in Example 6.

Morpholino oligomers are assembled predominantly by linking the Y group of one morpholino subunit structure to the morpholino nitrogen or Z group of another morpholino subunit structure (FIG. 2), where one of these groups is nucleophilic and the other is electrophilic. The resulting intersubunit linkage, L, should be stable to conditions of synthesis and any required deprotection steps, as well as stable under the conditions of use.

Figure 7:
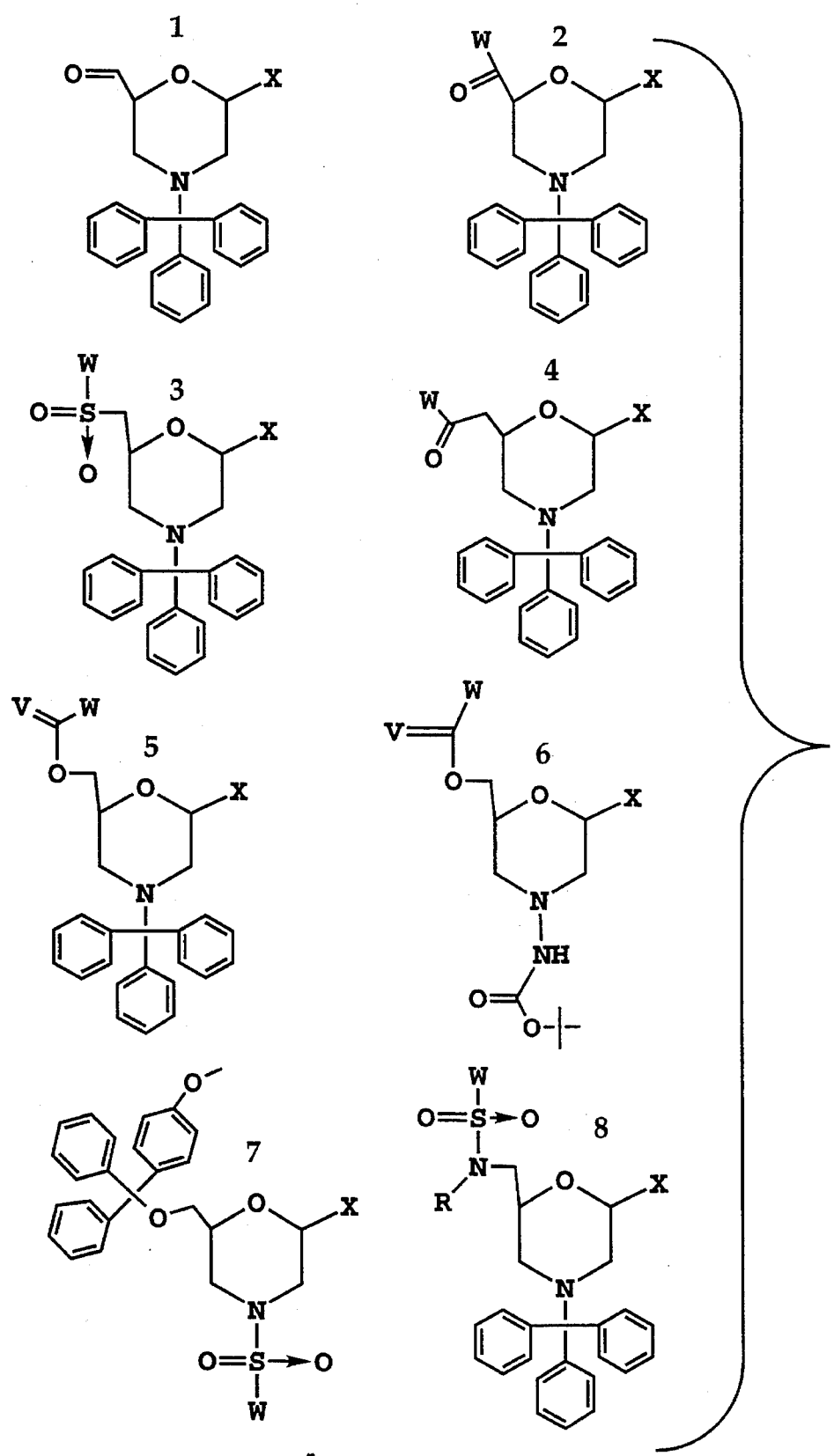
FIG. 7 illustrates a variety of activated subunit structures useful in forming the oligomers of the invention.

A preferred assembly method is to use subunit structures in which the nucleophilic moiety is in a protected form (often protected with a trityl group), and the electrophilic moiety is in an activated form, or is activated in situ just before or during the coupling step. FIG. 7 illustrates a number of representative morpholino subunits so configured for oligomer assembly, and Example 7 describes their preparation.

C. Conversion of Subunits to Morpholino Subunit Structures during oligomer assembly.

Figure 8:
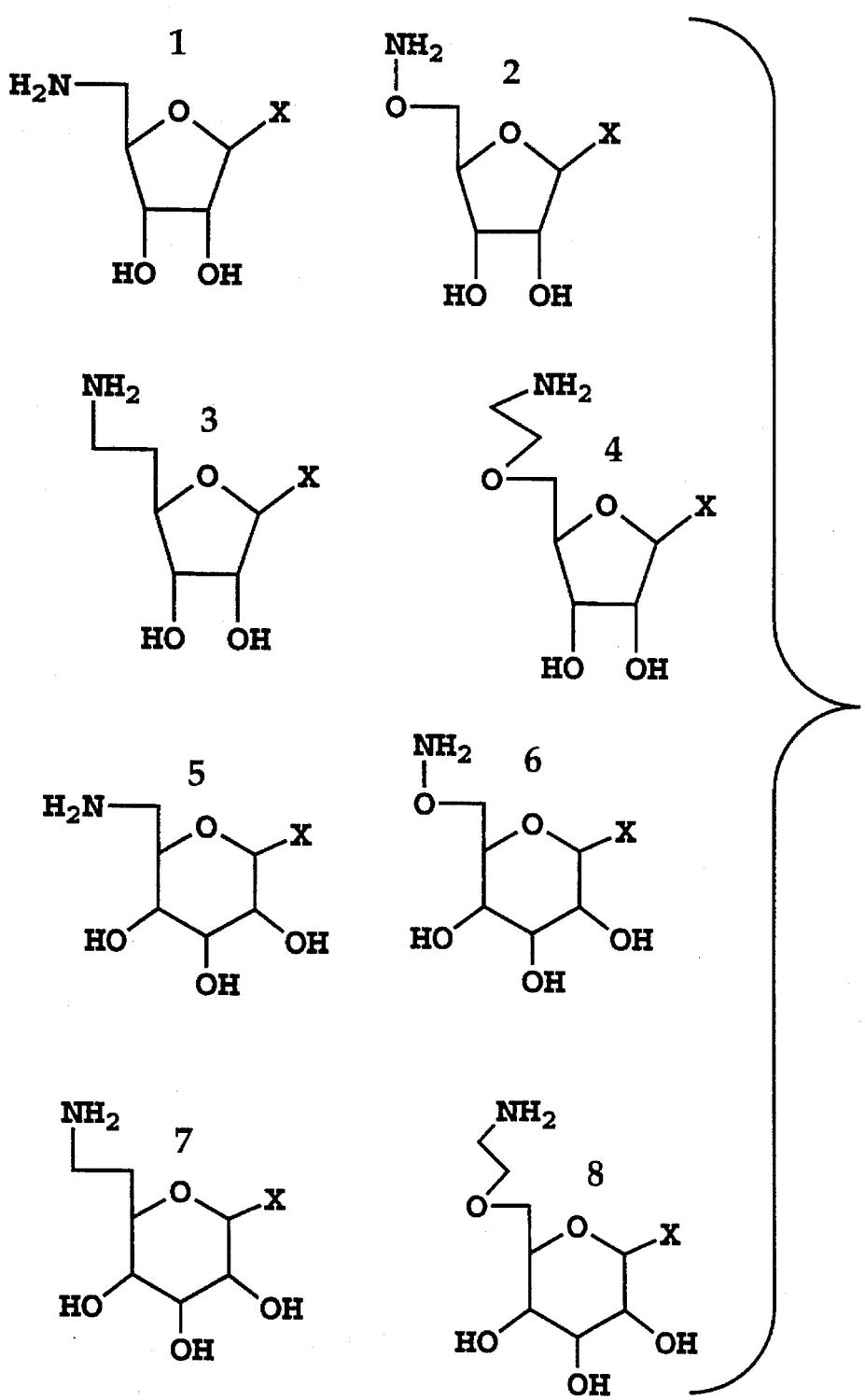
FIG. 8 illustrate compounds which may be converted to morpholino subunit structures during oligomer assembly.

In addition to oligomer assembly by coupling of preformed morpholino subunit structures, morpholino oligomers can also be assembled by a method in which the morpholino backbone moieties are formed in the course of oligomer assembly. FIG. 8 illustrates a number of representative compounds suitable for this purpose, and Example 8 describes their synthesis. Key structural characteristics of the backbone moiety of any such compound include a primary aliphatic amine moiety and two or more vicinal hydroxyls.

II. Oligomer Assembly

This section describes methods for preparing morpholino oligomers of the type used in the invention, and the spatial and geometric considerations important in polymer construction.

A. Side Chain Rotational Freedom

The diversity of spatial arrangements of the side chains in a library of morpholino oligomers can be increased appreciably by use of nucleobase and similar side chains which are structured so as to control their orientation about the bond between the side chain and the 1' atom of the morpholino backbone moiety. Based on NMR studies conducted in support of the invention, the morpholino backbone moiety exists predominantly in a chair conformation, with the X and Y groups positioned equatorial.

Figure 10:
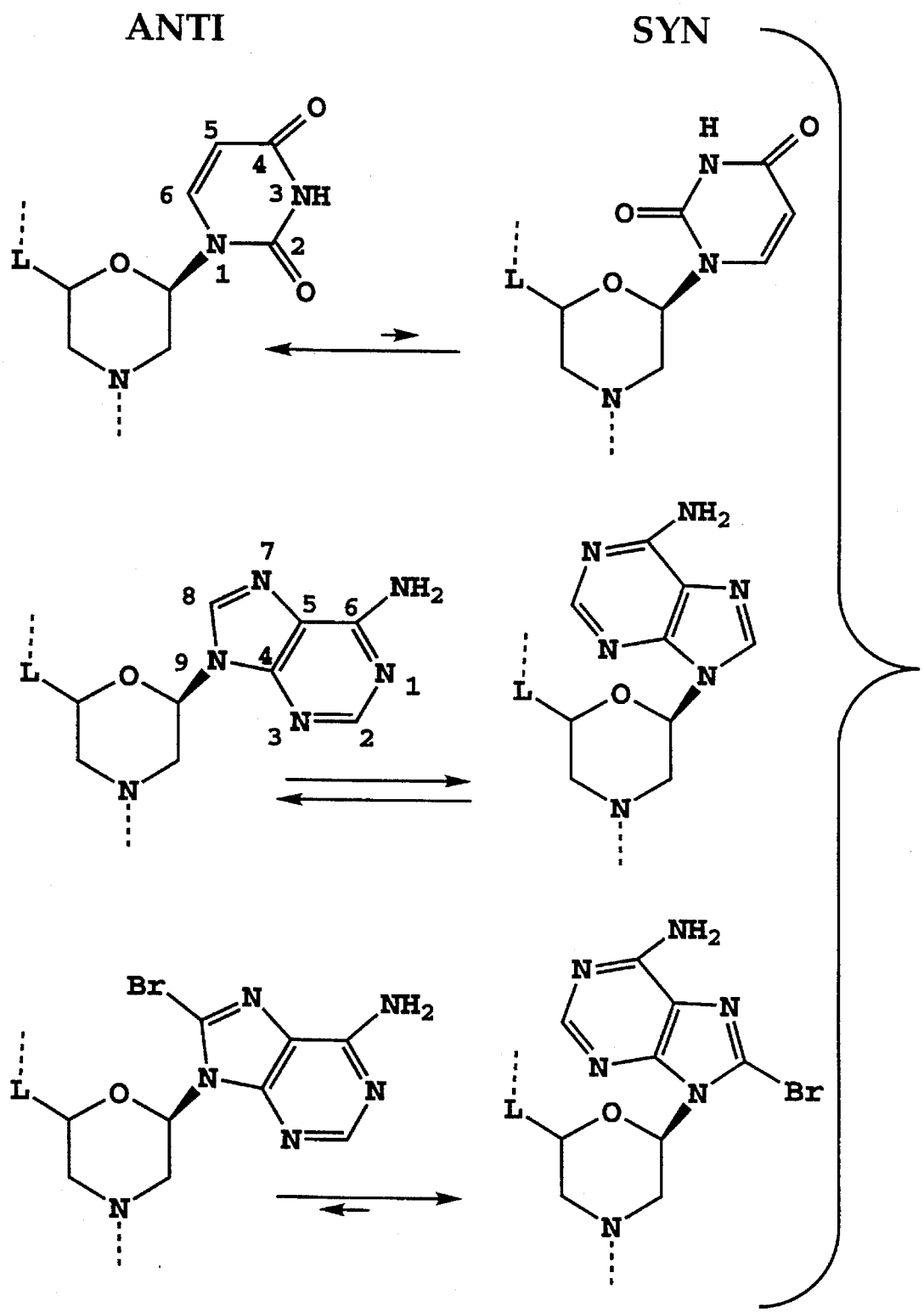
FIG. 10 illustrates orientation about the $X_i$ bond in morpholino subunit structures.

As indicated in FIG. 10, pyrimidines and related side chains which contain a bulky group at the 2 position and a hydrogen at the 6 position exist almost exclusively in the anti conformation about the X-1' bond. In contrast, purines and related side chains which contain a hydrogen at the 8 position can exist in either the syn or anti conformation about the X-1' bond. Further, purines and related side chains which contain a bulky group at the 8 position exist predominantly in the syn conformation about the X-1' bond.

B. Oligomer Linkage Rotomers

In selecting suitable intersubunit linkage types, a key objective is to prepare an oligomer library containing a collection of molecules, each of which has a definable spatial arrangement of side chains. In this regard, certain linkage constraints need to be considered. For example, if a bond has a high barrier to rotation, resulting in two distinct rotomers, and both rotomers are present at significant concentrations, then a given molecular specie containing such linkages would be expected to contain $2^n$ distinct, but slowly interconverting conformations, where n is the number of rotomer-generating restricted-rotation bonds in that oligomer. This results in a diverse collection of rotomers, only one of which has the desired spatial arrangement of side chains.

Even if the desired rotomer can be isolated, except in special cases it will slowly interconvert to form the original mixture of rotomers. In this context, tertiary amides and related groups containing a carbonyl linked to a nitrogen containing two alkyl groups are well known to exhibit two distinct rotomer forms which interconvert only very slowly at physiological temperatures. For instance, amides containing the dialkyl nitrogen of proline have been reported to have a $T_{1/2}$ of rotation of many hours at 37° C., and the temperature of coalescence (Tc), determined by nuclear magnetic resonance, has been found to be 114° C. To illustrate the impact of such rotomers on the spatial arrangement of side chains in polymeric structures, it is the slow interconversion of the tertiary amide of proline in polypeptides which is largely responsible for the failure of many proteins to spontaneously renature after heat denaturation.

Figure 11:
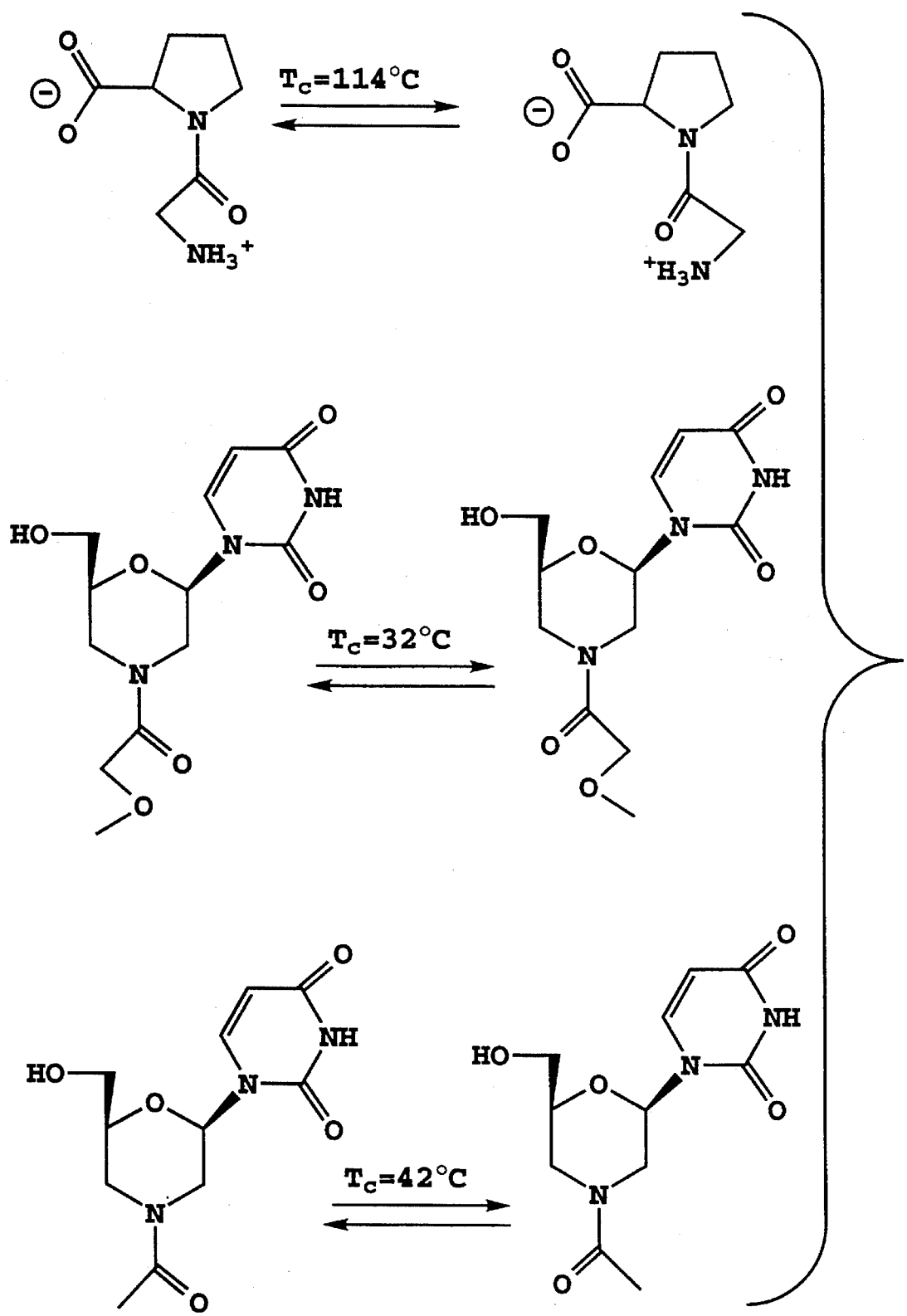
FIG. 11 illustrates rotational freedom about the amide linkage in selected tertiary amine linkages.

In view of the above considerations, intersubunit linkages containing tertiary amides might seem to be undesirable for morpholino oligomers destined for biological applications. However, in experiments carried out in support of the present invention, it has been discovered that in the special case of a carbonyl linked to the ring nitrogen of morpholino subunits, there is a relatively low barrier to rotation about this particular tertiary amide linkage, evidenced by the low Tc values for the amide-linked morpholino structures shown in FIG. 11.

Figure 14:
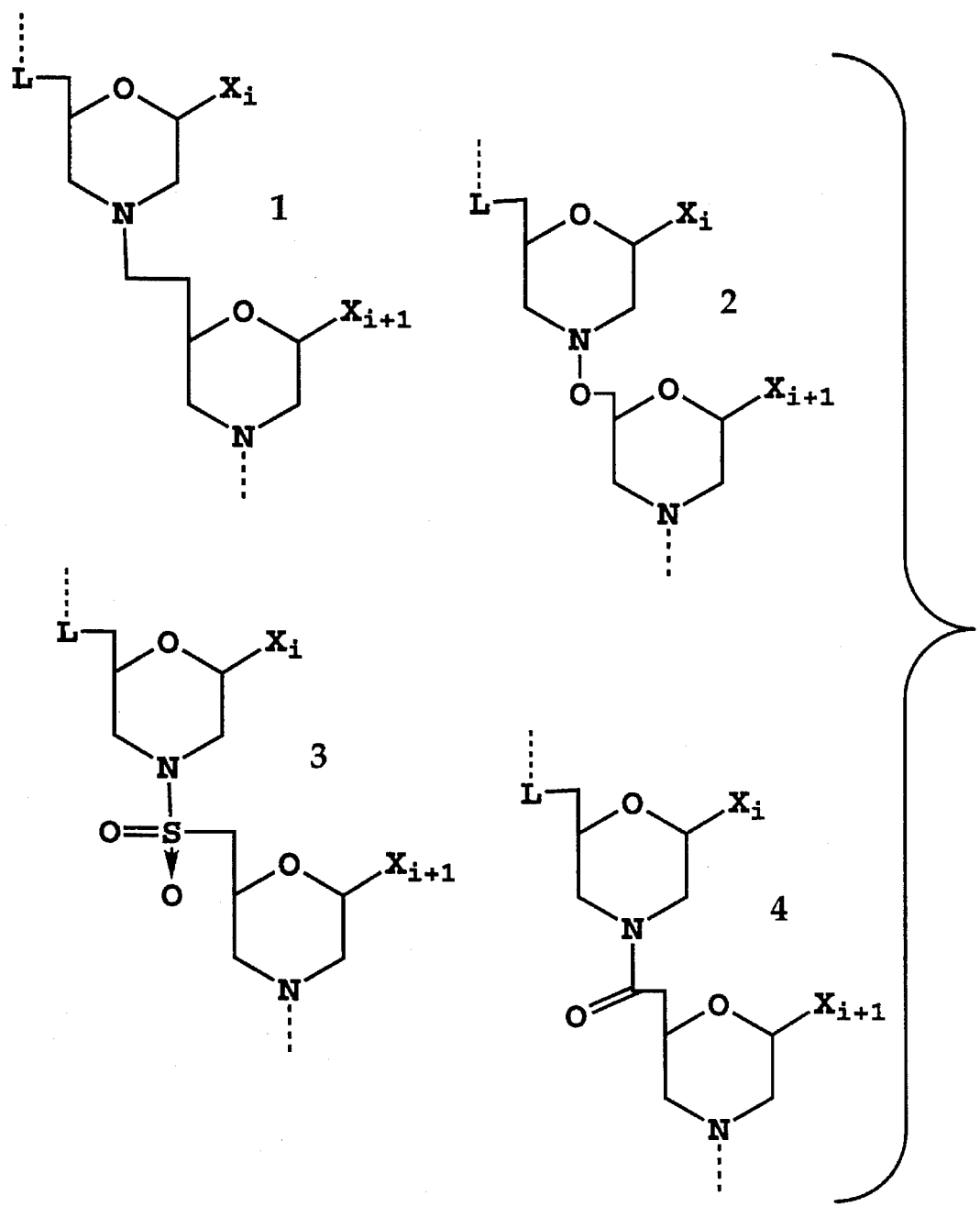
FIG. 14 shows representative two-atom linkages in oligomers of the invention.

Accordingly, tertiary amide intersubunit linkages to the ring nitrogen of the morpholino backbone moiety are now known to be acceptable linkages for a variety of morpholino oligomers. Novel intersubunit linkages of this type, which heretofore appeared to be unacceptable on the basis of previously available information, are illustrated in structure 1 of FIG. 12, structure 4 of FIG. 14, structure 2 of FIG. 15, and structure 2 of FIG. 16.

C. Forming Oligomers with One-Atom Linkages

One-atom-length linkages between morpholino subunits afford oligomer structures with little conformational freedom, which, in turn, minimizes the entropy cost of binding between such oligomers and suitable target structures. FIG. 12 shows two one-atom-length intersubunit linkages.

Figure 13A:
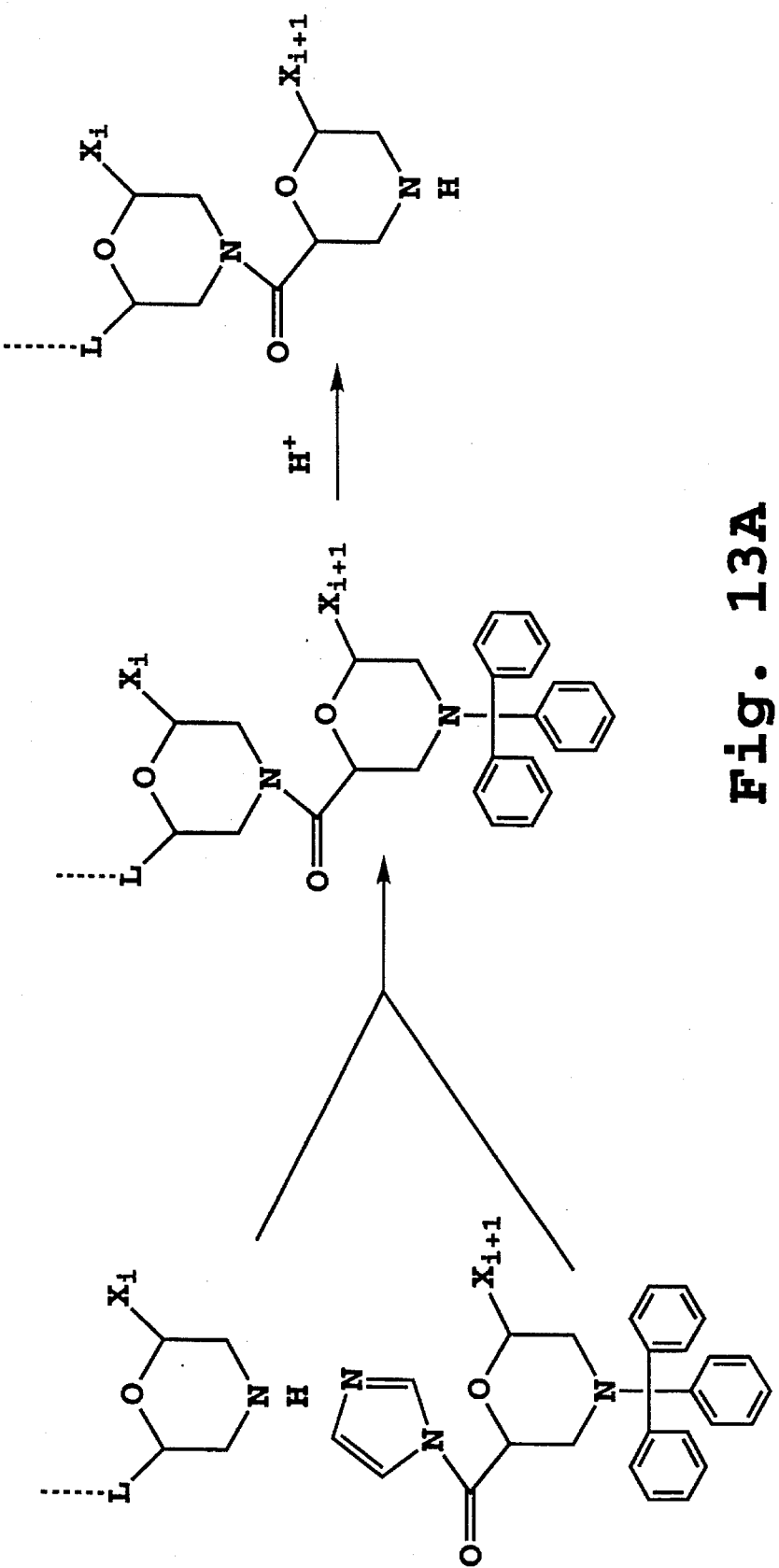
FIGS. 13A and 13B illustrates the syntheses of oligomers having one-atom linkages between morpholino subunit structures.
Figure 13B:
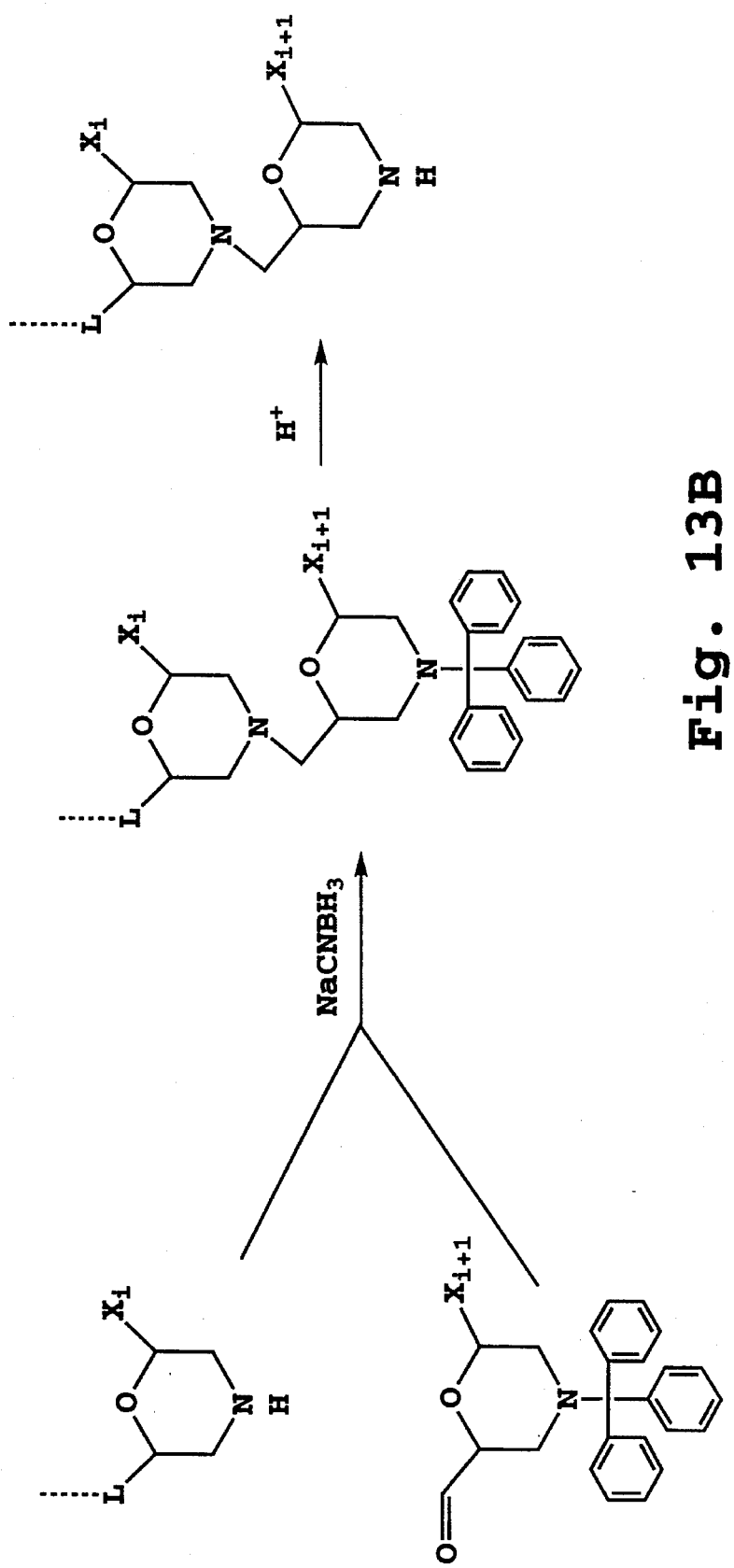

Methods for joining morpholino subunits to form these one-atom-length intersubunit linkages are illustrated in FIG. 13 and described in Example 9. Alternatively, oligomers containing one-atom linkages may be constructed by converting the last-added subunit to a morpholino group during oligomer synthesis, as illustrated in FIG. 9 for ribose and glucose subunits. The methods of synthesis are detailed in Example 10.

D. Forming Oligomers with Two-Atom Linkages

Two-atom-length linkages afford oligomer structures with greater conformational freedom than those with one-atom linkages. Exemplary two-atom linkages, shown in FIG. 14, can be formed by the general methods illustrated in FIG. 13 and described in Example 9, or by the general method illustrated in FIG. 9 and described Example 10.

Additional methods of synthesis of oligomers from morpholino subunits are also described in co-owned U.S. Pat. Nos. 5,235,033, and 5,185,444, which are incorporated herein by reference.

E. Forming Oligomers with Three-Atom Linkages

Figure 15:
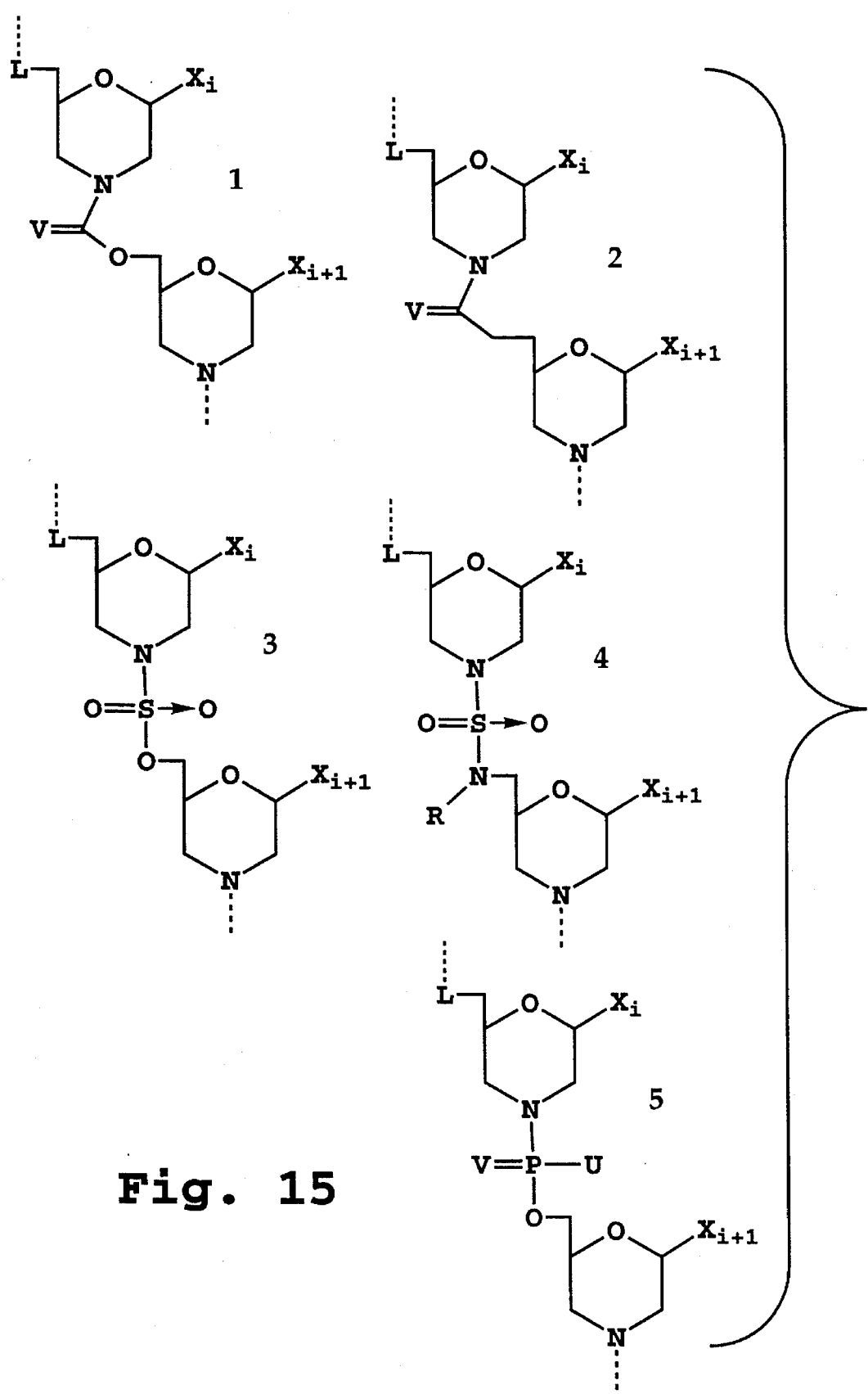
FIG. 15 shows representative three-atom linkages in oligomers of the invention.

FIG. 15 illustrates and Example 11 describes methods of forming representative three-atom-length linkages between morpholino subunits. Additional methods are described in co-owned U.S. Pat. Nos. 5,235,033 and 5,185,444. Such linkages properly space and position suitable nucleobase side chains for Watson/Crick binding to complementary single-stranded oligonucleotides, and to suitable complementary morpholino oligomers. Further, incorporation of a relatively rigid carbamate or thiocarbamate intersubunit linkage (structure 1 of FIG. 15) largely precludes stacking of adjacent nucleobase side chains in aqueous solution, resulting in substantial hydrophobic character for such nucleobase-containing oligomers. In contrast, incorporation of relatively flexible sulfonyl, and particularly phosphoryl linkages (structures 3, 4, and 5 of FIG. 15) affords good stacking of adjacent nucleobase side chains in aqueous solution, resulting in generally good water solubility for many such nucleobase-containing oligomers.

F. Forming Oligomers with Four-Atom Linkages

Figure 16:
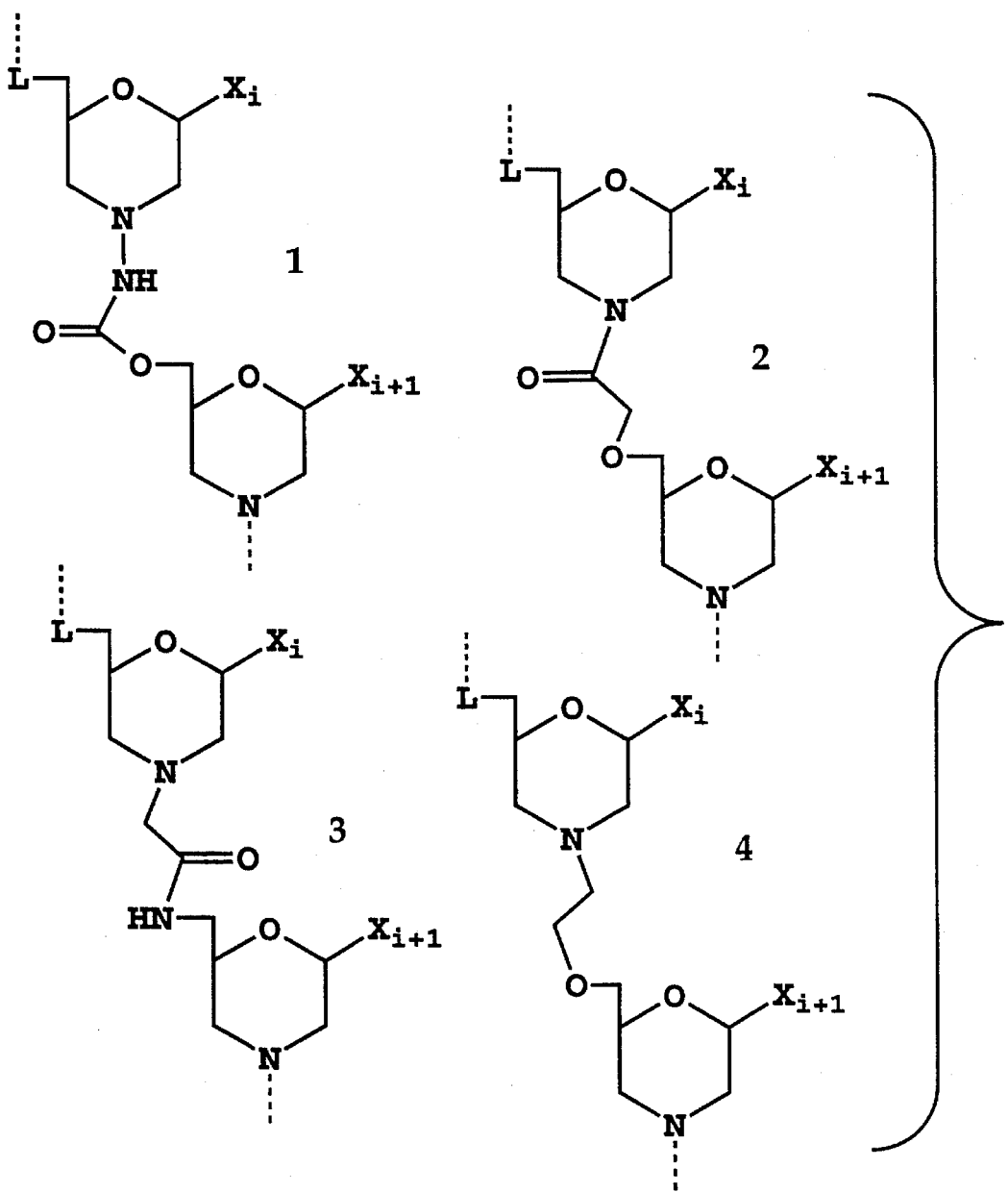
FIG. 16 shows representative four-atom linkages in oligomers of the invention.

Still greater spacing of the side chains in a morpholino oligomer is afforded by four-atom-length linkages between subunits. Representative four-atom-length intersubunit linkages are shown in FIG. 16. Methods of forming such linkages are described in Example 12.

It will be appreciated that non-morpholino subunits can be introduced into the morpholino-subunit oligomers, either in linear or branched portions thereof, by selecting subunit structures having suitable donor and acceptor groups, and incorporating these subunits into the oligomer by the general coupling methods described herein.

G. Forming Oligomers with Branches

Figure 17:
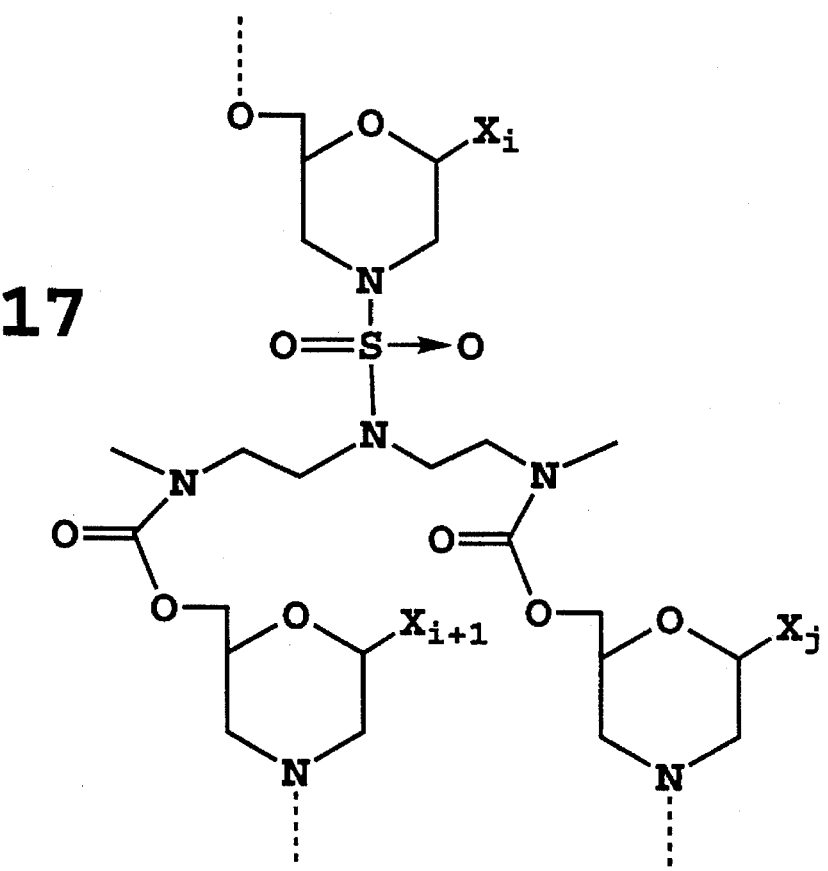
FIG. 17 shows a portion of a branched oligomer formed in accordance with another embodiment of the inventions.

Utilization of one or more branches in an oligomer can substantially increase the spatial diversity of its side chains relative to unbranched oligomers. One or more branches in an oligomer also serves to increase structural complexity by positioning a greater number of side chains in a small area, resulting in an increased likelihood of multiple interactions with a suitable target structure. FIG. 17 shows a portion of a morpholino-subunit oligomer having a branch linkage at which a 1–N subunit branch extends from a dominant linear portion of the oligomer (the longest linear chain in the oligomer).

Figure 18A:
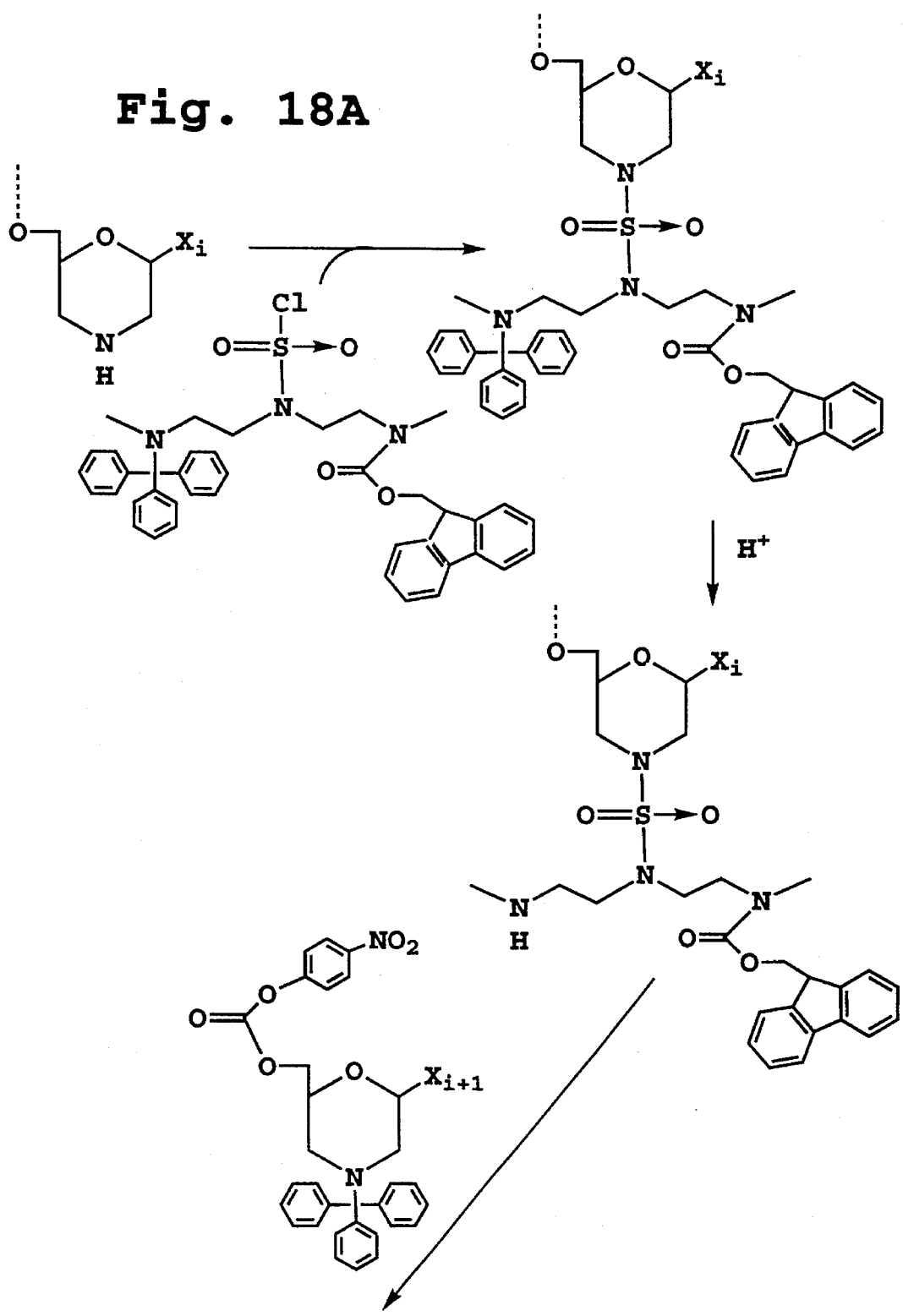
FIG. 18 illustrates the synthesis of the branched portion of the oligomer shown in FIG. 17.
Figure 18B:
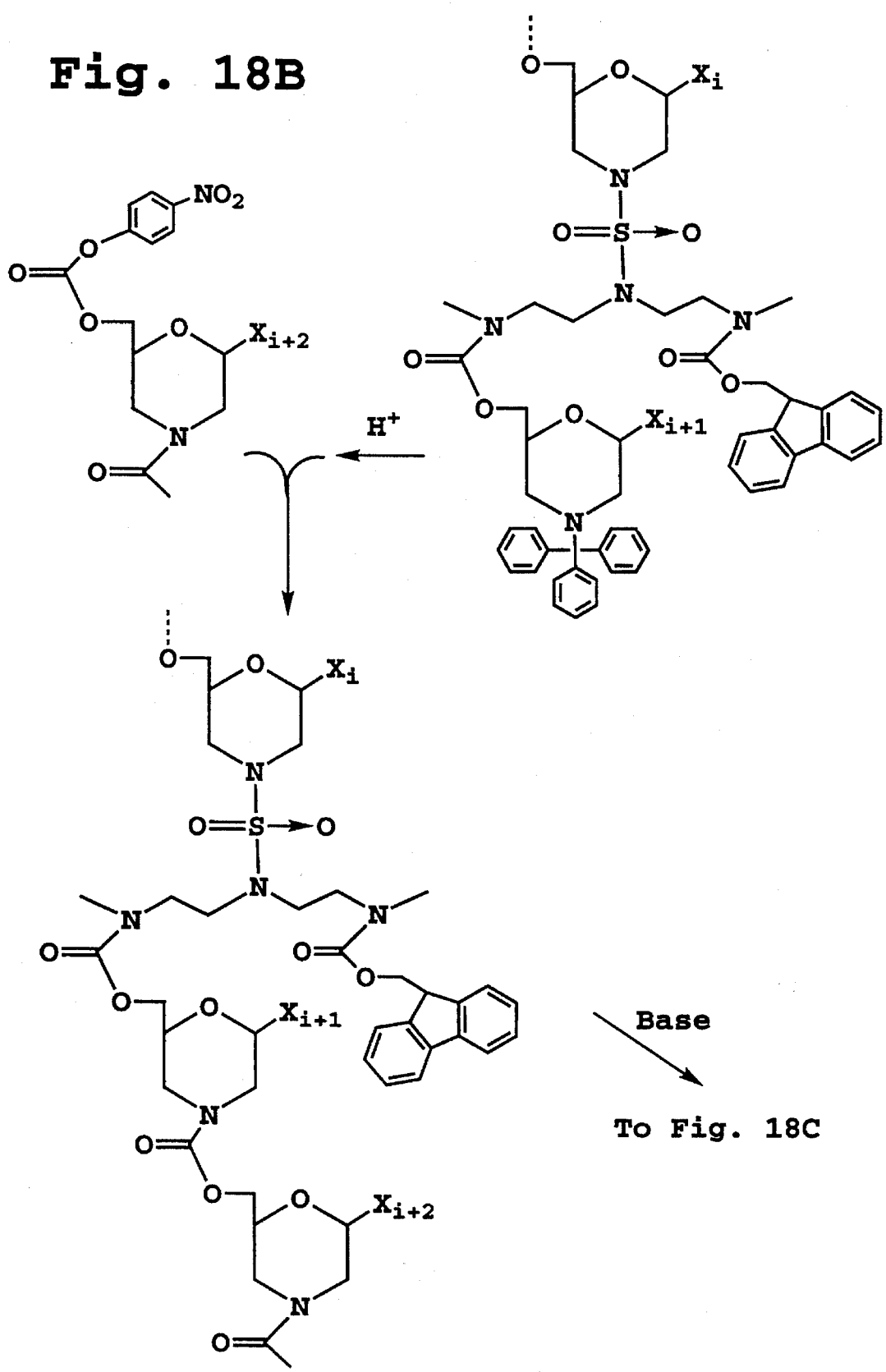
Figure 18C:
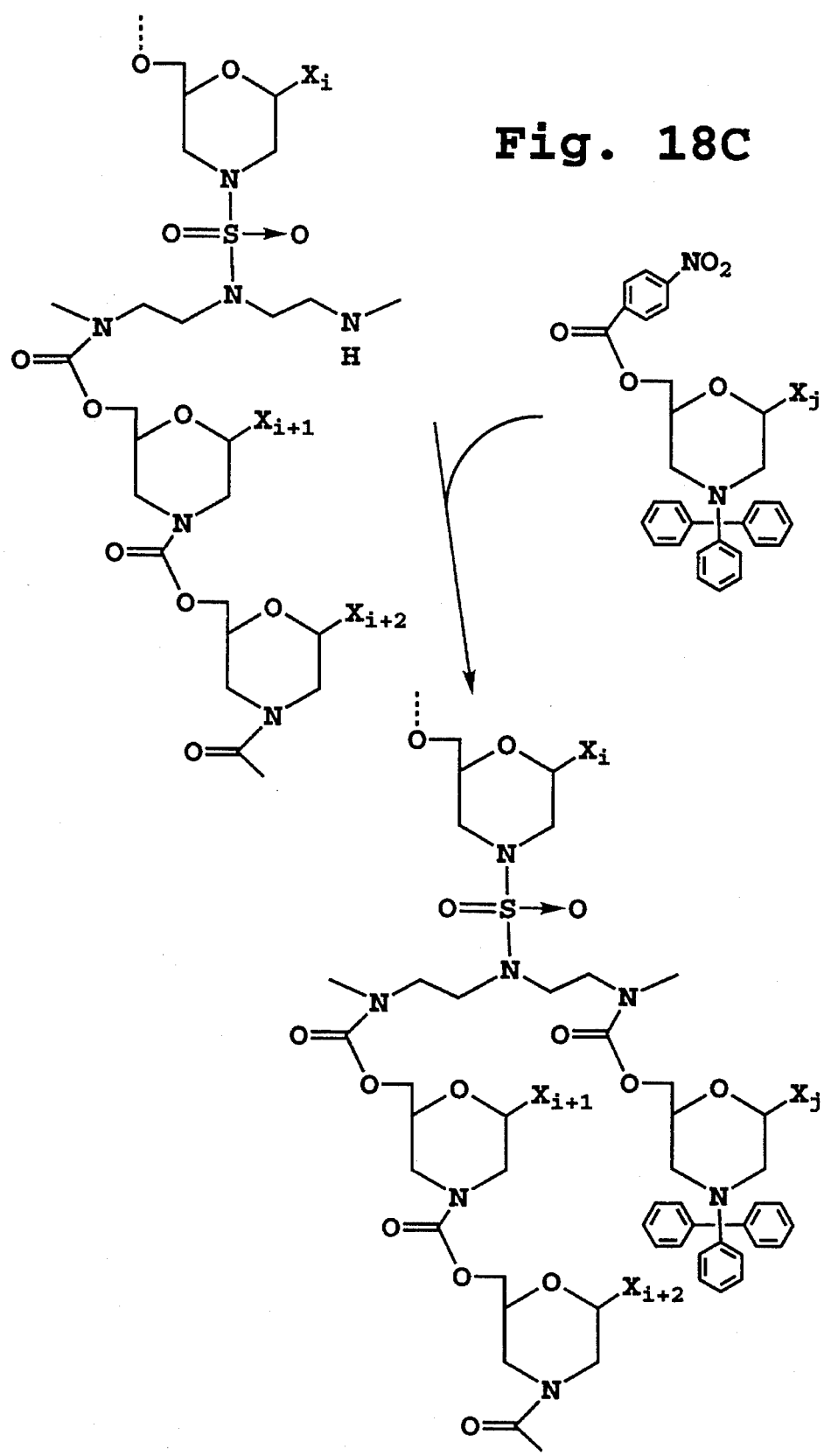

The branch oligomers may be formed by a variety of methods, typically by employing a branched structure which provides two nitrogens, each of which can be reacted with an activated subunit, as illustrated in FIG. 18. Example 13 describes the preparation of several such in-line type branches. Example 14 describes the synthesis of branced oligomers with hub branches. Example 15 describes the covalent joining of branched ends.

IV. Oligomer Libraries

This section describes the preparation and properties of combinatorial libraries of oligomers of the type described above. In general the libraries are constructed to contain oligomers having a large number of different sidechain sequences and, optionally, linkage sequences. Preferably, the oligomers making up the library include subunit structures with at least three, and typically 5–20 different side chains, and at least about 1,000 different side chain sequences. Preferably the library contains $10^4$ to $10^7$ different sequences, which may include different sidechains and different linkages. Each different-sequence specie in the library preferably exists in multiple copies, preferably $10^{10}$ or more where microsequencing is employed to determine oligomer sequence.

Subunits with the same X side chain but different Y and/or Z groups constitute different subunits, since changing the Y or Z moiety generally alters the relative spatial arrangement of the side chain in the oligomer. Further, subunits with the same X side chain and the same Y and Z, but with differing stereochemistry about the X and/or Y groups also constitute different subunits since changing the stereochemistry generally affords a substantial alteration of the spatial arrangement of the side chain in the oligomer. As a consequence, hundreds of different subunits can be readily prepared, in contrast to the four nucleotide subunits of enzymatically-prepared oligonucleotides and the 20 amino acids of biologically-generated peptides.

Combinatorial libraries of the type used in the invention may be formed by a variety of solution-phase or solid-phase methods in which subunits are added stepwise to growing oligomers, until a desired oligomer size is reached, as outlined below.

B. Solid-Phase Particle Library

In one preferred method, the library is formed by solid-phase synthetic methods in which beads containing different-sequence oligomers that form the library are alternately mixed and separated, with one of a selected number of subunits being added to each group of separated beads at each step. Each bead in the resultant library contains only one oligomer specie, allowing a single bead, once identified as containing the desired binding oligomer sequence, to provide oligomer for sequence identification.

Figure 20:
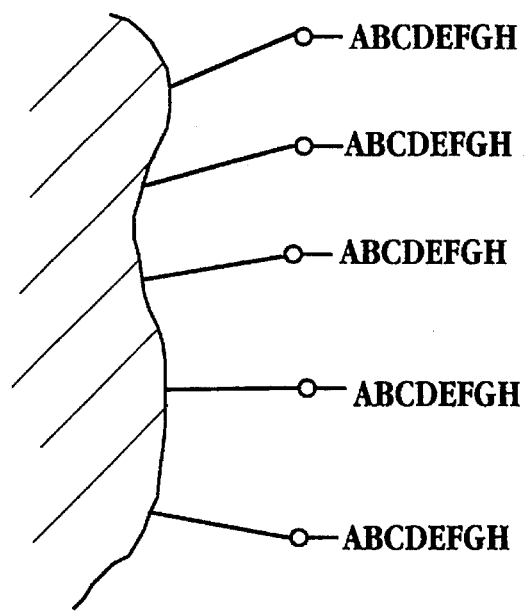
FIG. 20 shows a portion of a bead having a surface coating of same-sequence oligomer molecules.

One preferred particle or bead for use in library construction is a macroporous bead having a density of between 1 and 1.3, and a size of about 20–200 μm. With reference to FIG. 20, the particle, which is shown fragmentarily at 30, is preferably derivatized with a separator chain or tether, such as tether 32, having a cleavable linkage 34 adjacent its distal or free end, as detailed in Example 16.

Highly crosslinked macroporous polystyrene particles (buoyant density 1.05 g/cm$^3$) are particularly suited for use in preparing such oligomer-particles, and commercially available polystyrene particles with amine, hydroxyl, or carboxyl moieties covering their surfaces provide suitable sites for linking tethers and dyes or fluorescent groups.

Polyethylene glycols and polypropylene glycols, preferably with average molecular weights in the range of 400 to 6000, serve as effective tethers. Use of higher molecular weight tethers (>1000 MW) typically afford oligomer-particles with higher target binding capacities in the typical case where the target structure is relatively large, for example proteins, which generally range from 30 to 100 angstroms in diameter.

Figure 19A:
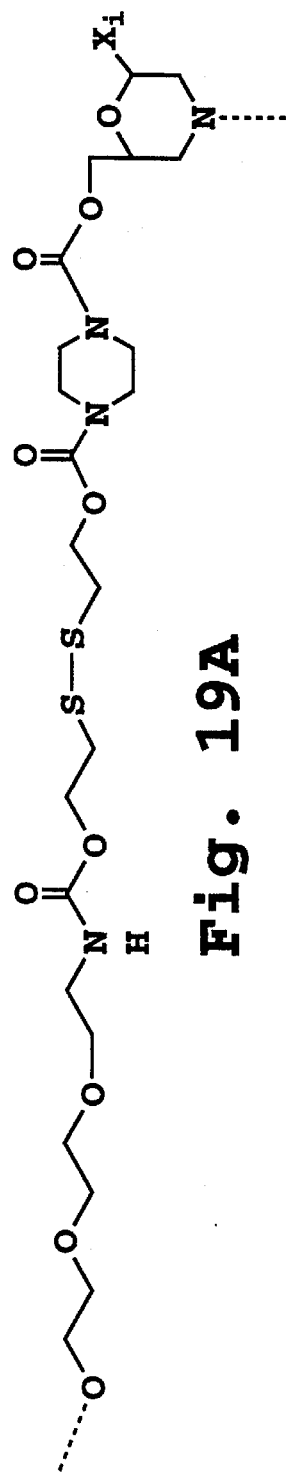
FIGS. 19A–19C show three different cleavable linkers used in attaching a morpholino oligomer to a tether bound to a particle surface.
Figure 19B:
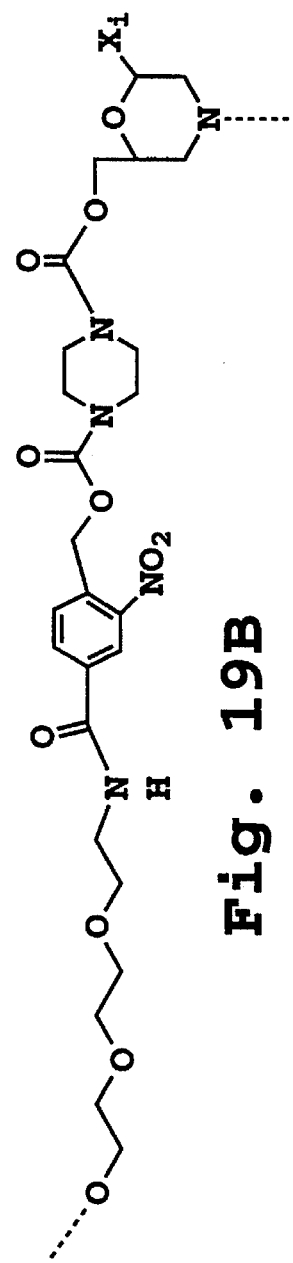
Figure 19C:
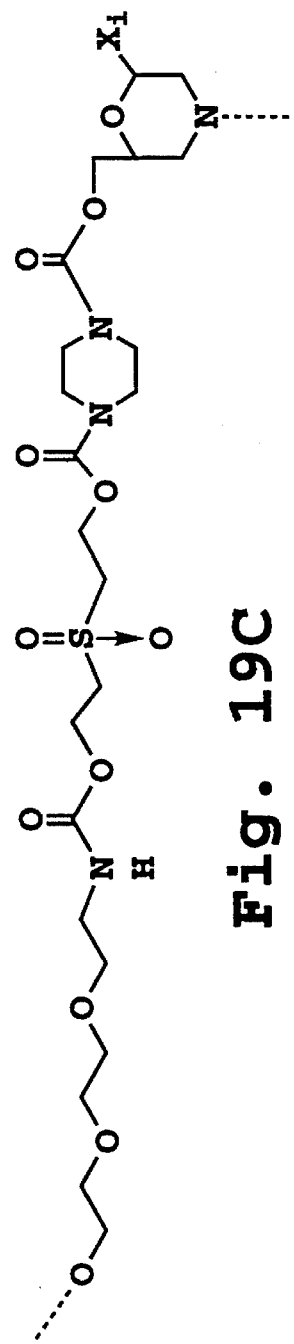

The selectively cleavable anchor between the tether and the oligomer should be stable to conditions used for subunit coupling, deprotection of termini, deprotection of side chains, and the aqueous conditions used for assessment of target binding. The linker should also be easily and selectively cleavable under simple conditions. Three linkages which satisfy these criteria are: disulfide (cleavable with mercaptoethanol); derivatives of 4-hydroxymethyl-3-nitrobenzoic acid (cleavable with 350 nm light); and vicinal alcohols (cleavable with periodate), as illustrated in FIGS. 19A–19C.

Macroporous particles, each containing many femtomoles to a few picomoles of functional sites on its surfaces, and preferably having a buoyant density appreciably less than that of the target structure, are reacted to add to the surface a water soluble tether ending in a selectively cleavable anchor. Remaining sites on the particle surfaces may be reacted with a suitable dye or fluorescent group, or dye or fluorescent material may be incorporated within the particle matrix during its polymerization. Such label is desirable to improve visualization of the oligomer-particles in the course of assessing for target binding.

A preparation of particles, containing at least several times as many particles as there will be oligomer species in the library, is next distributed into equal portions, where the number of portions is typically the same as the number of different subunits in the set of subunits to be used for assembly of the variable portion of the oligomers in the oligomer library. Each portion of particles is than reacted with a different subunit of the subunit set, such as subunit structure 36 in FIG. 20. After coupling, all portions of particles are combined, mixed thoroughly, washed, and treated to deprotect the oligomer termini.

This subunit addition cycle, comprising distribution of particles into separate portions, coupling each portion with a different subunit, recombining, mixing, washing, and deprotection of the oligomer termini, is repeated until the desired number of subunits have been added to give a complete library of oligomers covalently bound to the particles.

The collection of oligomer-particles are next treated to remove protective groups on the side chains, and then washed, after which they are ready for use. Example 16 describes representative procedures for preparing such oligomer-particles.

One particle in a completed library is illustrated in FIG. 20. The particle, shown fragmentarily at 38, contains a plurality of oligomer molecules, such as molecules 40, each having the oligomer sequence ABCDEFGH, representing the sequence of eight different subunit side chains. As shown, each oligomer molecules is attached to the particle through a tether, such as tether 42, containing a cleavable linker, such as linker 44. Methods for forming library beads of the type just described are given in Example 16.

C. Preparing Oligomer Sequence Families

In many applications, it may be desirable to prepare a library of oligomer families, where each family consists of different-length, but same-sequence oligomer molecules attached to the same particle. That is, the molecules all have the same sequence, beginning from one oligomer end, but contain different numbers of subunits, typically including molecules that contain from 1 to N subunits, where the largest oligomer contains N subunits.

Figure 21:
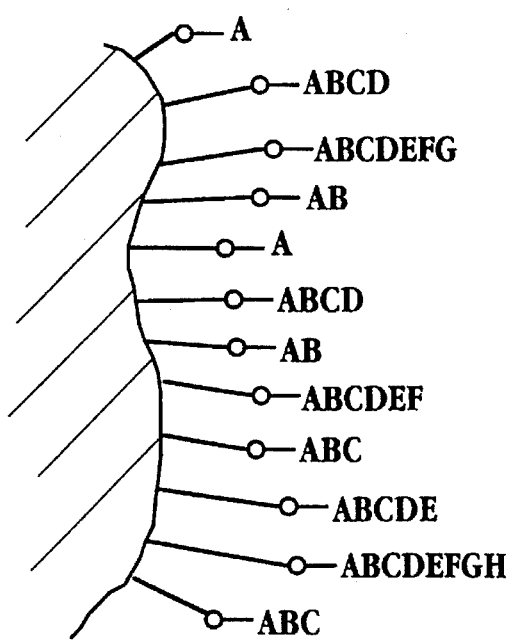
FIG. 21 illustrates a portion of a bead surface having a family of same-sequence, different-length oligomer molecules.

One exemplary particle in a completed library is illustrated in FIG. 21. The particle, shown fragmentarily at 46, contains a plurality of oligomer molecules, such as molecules 48, each having a portion of the sequence ABCDEFGH (including some molecules containing the entire sequence ABCDEFGH), of an oligomer having this side chain sequence. As above, the oligomer molecules are each attached to the particle through a tether, such as tether 50, containing a cleavable linkage, such as linkage 52. Two general methods for forming bead libraries of the type just will now be described and are detailed in Example 17.

In one method, when coupling a given subunit with a particular portion of particles a mixture of activated subunits is used wherein a defined fraction in the mixture (50% to 90%) contains a protective group which, after coupling, can be cleaved to allow coupling of a subsequent subunit in the next subunit addition cycle. The remaining fraction of subunit in the mixture (10% to 50%) is capped with a group which precludes coupling in subsequent subunit addition cycles. By this method each oligomer-particle will contain a family of oligomer species, this family comprising capped oligomers ranging from 1 to N–1 subunits, and an uncapped oligomer of N subunits.

If it is desirable to have the cap present during subsequent use of these particles for assessment of target binding, an acetyl cap is convenient. If it is desirable to remove the cap prior to use in the target binding assessment, a trifluoroacetate cap can be used. This group is removed during the treatment with ammonium hydroxide typically used for deprotecting side chains.

In using this method of generating families of oligomers on a single particle, when branched oligomers are prepared, the method can lead to ambiguities in sequence information generated in the final mass spectral analysis. Such ambiguities arise because truncation can occur independently in each of the branches. A strategy to remove most, and often all of this sequence ambiguity is to incorporate a dual-mass cap in those oligomers which are truncated in the first-synthesized branch. One representative dual-mass scheme which is easily assessed in the mass spectral sequencing step entails utilizing a mixture of acetyl and benzoyl capped subunits in the subunit mixtures used for the first-synthesized branch of a branched oligomer, while using just the acetyl cap for subunit mixtures used for all other subunits additions. This affords a mass series in which eah oligomer truncated in the first-synthesized branch is distinguished by dual masses, separated by 62 mass units. Another dual-mass scheme entails using a mixture of acetyl and trifluoroacetyl capped subunits for the first-synthesized branch, and just trifluoroacetyl capped subunits for subunit mixtures used for all other subunit additions. After assembly of the oligomer library is completed, the trifluoroacetyl moieties are cleaved by treatment with ammonia. This affords a mass series in which each oligomer truncated in the first-synthesized branch is distinguished by dual masses, separated by 42 mass units.

An alternative method for generating oligomer-particles containing families of different-length, same sequence oligomers has been developed for morpholino oligomers. In this approach (which does not utilize mixtures of capped and protected subunits), the protective group on the chain termini which is to be cleaved at the end of each subunit addition cycle is a trityl group on the ring nitrogen of a morpholino subunit. Trityl cleavage is carried out with dichloromethane solutions which contain >5% formic acid (v/v). This formic acid treatment is effective to formylate the terminal morpholino nitrogen at a relatively constant rate for a given concentration of formic acid. For example, 7% by vol formic acid in dichloromethane formylates morpholino chain termini at a rate of 2.5%/hr at 20° C.

Therefore, by simply exposing the particles containing nascent morpholino oligomers to a suitable formic acid deprotection solution for a selected period of time one can achieve truncation of a desired percent of chain termini. When concentrated ammonium hydroxide, neat or as a 1:1 v/v mixture with dimethylformamide, is used for deprotecting the side chains, these formyl moieties are cleaved from the truncated chains, leaving the terminal morpholino nitrogen in the free base form.

For branched oligomers, it is desirable to utilize the dual mass capping strategy described above for the first-synthesized branch, and this controlled formylation method for all other subunit additions.

V. Selecting Specific-Sequence Oligomer Molecules

The combinatorial libraries described above are used to select one or more oligomer species in the library that demonstrate a specific interaction with a selected receptor. The receptor is any biological receptor of interest, that is, one for which it is desired to identify a oligomer (ligand) that binds specifically to the receptor, to affect the functioning of the receptor in its normal physiological setting.

For example, the receptor may be an enzyme, where the oligomer is able to bind to the active site of the enzyme or otherwise inhibit the action of the enzyme on a normal substrate.

In another general embodiment, the receptor may be a cell receptor protein, such as an ion channel or other transport receptor protein, or a receptor site for a hormone or other cell effector, or a receptor site for binding of pathogenic bacteria or viruses to a cell surface. The receptor protein may be associated with isolated cells with culture cells, with biological membrane particles isolated from tissues, with cells which are transformed to produce the receptor recombinantly, or with isolated cell receptors. Receptor proteins of this type, and expressed or isolated in a variety of forms, have been described in the literature, such as that cited above.

In a related embodiment, the receptor is an antibody or antibody fragment, where it is desired to identify an "artificial" epitope ligand that binds specifically and with high affinity to the antibody.

In a typical application, the library of oligomers is screened for oligomer (ligand) molecules that bind specifically and with high affinity, e.g., with a binding constant $K_B$ greater than $10^6 M$, to the receptor. In one embodiment, illustrated in FIG. 22, receptor molecules, such as molecules 54, are attached to a solid support 56. Attachment may be by way of covalent or noncovalent attachment of an isolated receptor to the surface. Alternatively, the solid surface may be cells having surface-bound receptor, or the cells themselves may be anchored on a solid support. Methods for attaching proteins or cells to a solid support are well known.

In the selection method the support is contacted with the library oligomers, i.e., the different-sequence oligomer molecules making up the oligomer library, under conditions that allow binding of only one or a few oligomer species to the receptor. The binding conditions, e.g., salt concentration, pH and/or temperature may be selectively varied, according to standard methods, to ensure that only the highest-affinity oligomer species are bound to the receptor.

In the method illustrated in FIG. 22, the library is constructed as above to include a library of particles, each containing multiple copies of the same-sequence oligomer. The particles are reacted with support-bound receptors under conditions which promote binding to the solid surface of library particles, indicated at 58, that carry high-affinity ligands, such as oligomers 60, for the receptor.

Following this binding, the solid surface is washed to remove unbound or less tightly bound particles, and the one or more remaining bound particles are then analysed, according to methods described below, to determine the sequence of the high-affinity oligomers.

FIGS. 22A–22D illustrate various solution-phase methods for identifying desired library oligomer sequence(s). Here a library particle 62 carrying molecules, such as molecules 64, having one of the library sequences is reacted with the receptor 66 in solution phase, under conditions which lead to receptor binding to high-affinity library particles, as illustrated in FIG. 23B.

The particles with bound receptor may be further reacted with reported-labeled antibody 68 specific against the receptor molecules, to label the desired library particle(s) with a suitable reporter, such as a fluorescent label, as indicated in FIG. 23C. The labeled particles may be removed by micromanipulation, e.g., under fluorescent microscopy, or using standard cell sorting methods to isolated reporter-labeled particles.

Alternatively, the particle density may be so selected that binding of receptor protein to the particles increases the particle density sufficiently to separate receptor-bound particles on the basis of differential density, as illustrated in FIG. 23D. The figure shows a receptor-bound particle being separated by centrifugation or particle settling in a medium 70 whose density is intermediate between the density of particles 72 that do not contain bond receptor, and those, such as particle 62, that do.

A preferred type of particle for density separation which has desired density and solvent-resistance properties is macroporous polystyrene particles in the size range of 20 to 200 microns in diameter. Such macroporous particles, which are used for ion exchange chromatography, can be obtained which have large surface to mass ratios, suitable pore sizes (in the range of 400 to 1000 angstroms), and which have surfaces containing covalently linked amine, hydroxyl, or carboxyl groups, which provide convenient sites for anchoring oligomers.

Other methods of isolating library particles having desired receptor-binding properties are also contemplated. For example, in the case of an antibody receptor, the bivalent nature of the antibody could be used to crosslink particles having high-binding ligands on their surfaces.

Alternatively, where the receptor is carried on cell surface, the library particles, such as polymeric particles having particle sizes in the 0.5–2 μm range, are reacted with the cells under conditions that promote ligand-specific receptor surface binding, followed by one or more cell washes, to remove unbound particles, and release of bound particle(s) from teh washed cells.

VI. Determination of Oligomer Sequence

Once a library oligomer having a desired interaction, e.g., binding interaction, with a receptor is identified, the oligomer molecules, it must be sequenced to determine the sequence of side chains. This may be done in accordance with various sequencing methods, several of which are given below, and in Example 18.

A. Oligonucleotide Amplification

As indicated above, the oligomer library may be formed of oligomer molecules having (i) nucleobase side chains and (ii) intersubunit linkages that allow Watson-Crick base pairing between the nucleobases the bases of complementary-base sequence oligonucleotides.

In this embodiment, the isolated oligomer molecules, whether in solution phase or carried on a particle, are reacted with a combinatorial library of oligonucleotides, under hybridization conditions that permit complementary strand hybridization between the selected oligomer molecules and same-sequence oligonucleotide molecules.

The bound oligonucleotide molecules are then released, made double stranded, amplified, e.g., by polymerase chain reaction, and sequenced according to standard methods. The sequence obtained corresponds then to the side-chain sequence of the isolated oligomer molecules.

Both the library oligomer molecules and the random-sequence oligonucleotides may have known-sequence oligonucleotide end segments to enhance hybridization between the two. If the oligomers are designed to contain a mixture of nucleobases and either modified nucleobases or non-nucleobase sidechains, the stringency of the hybridization conditions may be reduced, to allow some non-pairing with oligomer bases. Sequencing the bound oligonucleotides would be effective to reconstruct the oligomer sequence in some, but not all, subunit positions.

B. Isolated Particle Sequencing

In the embodiment in which the library oligomers are contained on particles, with each particle containing only one oligomer sequence, the isolated particles are treated to release the attached oligomer molecules, and the release molecules are sequenced, e.g., by micro mass spectrometry, such as detailed in Example 17 below. Preferably, each particle provides sufficient oligomer material for microsequencing, to avoid the problem of sequencing mixed-sequence oligomers derived from different beads.

In a modification of this approach, the library particles are prepared to contain a family of different-length, same-sequence oligomer molecules, as described above. After cleavage of the family of oligomers from an isolated particle surface, sinapinic acid is added and the material is placed under reduced pressure to remove volatile material, and then inserted into a mass spectrometer, preferably a laser-desorption time-or-flight mass spectrometer. By this means, when the oligomer-particles are assembled as described above, the mass spectrum permits ready determination of the exact mass of each subunit, as well as the order of said subunits in each oligomer specie of the family of oligomers. This procedure even affords exact structures for properly assembled branched oligomers.

Once the sequence has been determined for the family of N oligomers species from a single particle, oligomers having that sequence, and sizes ranges from 1 to N subunits, may be prepared to determine the oligomer length that affords highest binding affinity, or which provides the best compromise between high binding affinity and length.

C. Solution-Phase Iterative-Search Method

In those cases where it is desirable to test oligomers free in solution, instead of attached to the surface of a particle, oligomer libraries can be prepared as described earlier, but cleaved from the support before testing. When testing is carried out with oligomer free in solution, one can assess for a broader range of activities than just target binding, such as inhibition or activation of enzymes, blocking of binding of ligands, etc.

Screening of these oligomers free in solution, along with an iterative selection and synthesis process for the systematic identification of oligomers having a desired biological activity can be carried out by methods modeled after those reported by Houghten, et al. (Nature 354 84 (1991)).

From the foregoing, it can be appreciated how various objects and features of the invention are met. The combinatorial library is easy to synthesis by stepwise solution-phase or solid-phase methods, with the morpholino subunit structures making up the oligomers being preformed or formed during stepwise synthesis. The ability to construct subunit structures with a wide range or nucleobase, modified nucleobase, aromatic, aliphatic, and mixed base side chains allows the construction of libraries having virtually any desired degree of complexity. The possible complexity of the libraries is further enhanced by the stereochemical variations, and variations in linkages that are possible, as well as the ability to construct branched oligomers.

The oligomers may be readily screened for a desired interaction with a selected receptor, e.g., according to binding affinity. The invention provides a variety of methods for isolating library particles containing desired oligomer ligands, as well as simple methods for determining oligomer sequences.

The following examples illustrate various synthetic procedures for preparing oligomers useful in the invention. The examples are intended to illustrate, but not limit the scope of the invention.

Materials

Unless otherwise indicated, chemicals are purchased from Aldrich Chemical Co. Abbreviations used: Tr=trityl (triphenylmethyl); DMT=4,4'-dimethoxytrityl; CBz=(phenylmethyl)oxycarbonyl; Boc=(1,1-dimethyl)ethyloxycarbonyl; FMOC=(9-fluorenylmethyl)oxycarbonyl; TBDMS=tert-butyldimethylsilyl; TBDPS=tert-butyldiphenylsilyl, Ac=acetate; Bz=benzoate, DBU=1,8-diazabicyclo[5.4.0]undec-7-ene, NMP=1-methyl-2-pyrolidinone.

Referenced Methods

The following references disclose various synthetic procedures referred to in the examples, and are incorporated herein by reference:

Allevi, et al., J. Chem. Soc., Perkin Trans 1 1275 (1981).

Araki, et al., Tetrahedron Lett. 29:351 (1988).

Armitage, et al., J. Chem. Soc., Perkin Trans 1 680 (1972).

Bellosta and Czernecki, J. Chem. Soc., Chem. Commun., 199 (1989).

Benseler and McLaughlin, Synthesis, 46 (1986).

Carpino, et al., J. Chem Soc., Chem. Commun. 358 (1978).

Carpino and Han, J. Org. Chem. 37:3404 (1972).

Chow and Danishefsky, J. Org. Chem. 55:4211 (1990).

Cook, et al., J. Amer. Chem. Soc., 98:1492 (1976)

Czernecki and Ville, J. Org. Chem. 54:610 (1989).

Heikkila and Chattopadhyaya, Acta Chem. Scand., B37:263 (1983).

Hiskey and Adams, J. Amer. Chem. Soc. 87:3969 (1965).

Holy, et al.,Collect. Chezh. Chem. Common., 42:2246 (1977).

Köster, et al., Tetrahedron, 40:1031 (1984).

Knieb-Cordonier, et al., Int. J. Peptie Protein Res., 35:527 (1990).

Kraus and Molina, J. Org. Chem. 53:752 (1988).

Kruse, et al., Tetrahedron Lett., 885 (1977).

Lichtenhaler, et al., Tetrahedron Lett., 24:2141 (1974).

Martin and Lai, J. Org. Chem. 55:5188 (1990).

Maercker, Org. React., 14:270 (1965).

Niedballa and Vorbrüggen, J. Org. Chem. 39:3654 (1974).

Pischel and Wagner, Arch. Pharm (Weinheim), 300:602 (1967).

Posner, Org. React., 22:253 (1975).

Rammler and Khorana, J. Amer. Chem. Soc., 84:3112 (1962).

Sakakibari, et al., Carb. Res. 95:291 (1981).

Southon and Pfleiderer, Chem. Ber., 111:996 (1978).

Srivastava and Nagpal, Experentia, 26:220 (1970).

Stork and Isobe, J. Amer. Chem Soc., 97:6260 (1975).

Tronchet, et al., Nucl. Nucl., 12:615 (1993).

Vorbrügen, et al.,Justus Liebigs, Ann. Chem. 988 (1975).

Winkley and Robins, J. Org. Chem. 33:2822 (1968).

Wittenberg, Z. Chem. 4:303 (1964).

Yamamato, et al., J. Chem. Soc., Perkin Trans 1 306 (1980).

Yanagisawa and Kanazaki, Heterocycles, 35:105 (1993).

EXAMPLE 1

Preparation of Morpholino Subunits from Substituted Ribofuranosides

A. General procedure for protection of the R group.

1. Protection of amino groups on heteroaromatic rings. The ribofuranoside (1 mol) is suspended in acetonitrile (2.5 L) and hexamethyldisilazane (5 mol) is added. The solution is refluxed until solution is complete and the solvents then are removed by distillation. Residual hexamethyldisilazane is removed by addition of xylene (1L) and removal by distillation. The residue is dissolved in pyridine (2.5L) and treated with trimethylchlorosilane (5 mol). After the solution is stirred for 15 minutes, an acid chloride or chloroformate or similar acylating agent (5 mol) is added and the solution is maintained at room temperature for 3–24 hours. The reaction is cooled in an ice bath and water (500 ml) is added. After stirring for 5 minutes conc. ammonia (500 ml) is added, and the reaction is stirred for 15 minutes. The solution is evaporated to near dryness and the residue is poured into water (10 L). The product is isolated by filtration.

Representative examples of ribofuransoides and the corresponding acylating agents are cytidine and benzoyl chloride; adenosine and benzoyl chloride; guanosine and the ester formed from 1-hydroxybenzotriazole and phenylacetyl chloride (Benseler and McLaughlin). Alternatively, the FMOC group may be introduced by the method of Heikkila and Chattopadhyaya.

2. Protection of aliphatic or carbocyclic aromatic amines. Amino groups are protected by conversion to the trifluoroacetamide by treatment with p-nitrophenyl trifluoroacetate or trifluoroacetic anhydride, or by conversion to the 2-trimethylsilylethyl carbamate by the method of Carpino or the FMOC group by the method of Carpino and Han.

3. Protection of thiols. The mercapto group is reacted by the method of Armitage, et al, to produce the S-disulfide.

4. Protection of alcohols. Alcohols may be protected by reaction with benzoyl chloride or a substituted benzoyl chloride, eg, anisoyl chloride, in pyridine to form the ester. Alternatively, the hydroxyl group is silylated with t-butyldiphenylsilyl chloride and imidazole in DMF.

B. General procedure for formation of the morpholino ring.

1. Using ammonia. The furanoside (1 mole) is oxidized in methanol (4L) at room temperature by the addition of sodium periodate (1.1 mol) in 400 mL of warm water with vigorous stirring and exclusion of light. After the oxidation is complete, the reaction is filtered to remove sodium iodate and the filtrate treated with ammonium biborate (1.2 equivalents). After stirring for 30 minutes, the mixture is treated with sodium cyanoborohydride (1 mol) followed by 6N hydrochloric acid until a pH=4.5 is obtained. The reaction is allowed to sit at zero degrees C. overnight and then evaporated.

As an alternative, p-toluenesulfonic acid (or other arylsulfonic acid) may be used in place of 6N HCl in the reduction step. In certain cases a crystalline salt of the morpholino derivative and the sulfonic acid is obtained which may be filtered off and used in the next step. This method is especially effective for morpholino derivatives of uridine, N-4 benzoylcytidine and N-2 phenylacetylguanosine.

2. Using primary amines. The ribofuranoside is oxidized with periodate as in the example above, and the filtered dialdehyde treated with 1.2 moles of a primary amine. Two amines which are satisfactory for this purpose are 4-methoxyaniline and 4-methoxybenzyl amine. After stirring for 30 minutes, the mixture is treated with sodium cyanoborohydride (1 mol) followed by 6N hydrochloric acid until a pH=4.5 is obtained. The reaction is allowed to sit at room temperature overnight and the product N-aryl or N-alkyl morpholino subunit is filtered from solution.

C. General procedure for protection of the morpholino ring nitrogen.

The crude residue, or sulfonate salt, from the morpholino ring synthesis is suspended in DMF (2L) and treated with triethylamine (10 moles) and evaporated to near dryness. The residue is again suspended in DMF (2L) and treated with triethylamine (4 moles) and trityl chloride (2 moles) while the temperature is maintained at 10 degrees C. The reaction is vigorously stirred for 15 minutes at room temperature, then quenched by the addition of piperidine (1 mole). After 5 minutes, the reaction is poured into 20L of a one to one water/satd NaCL solution. The solids are collected, washed with water, and dissolved in 2L of 20% methanol/chloroform. To this is added 2L of 20% isopropanol/chloroform and the mixture washed consecutively with water, 5% sodium bicarbonate, and brine. The organic layer is dried over sodium sulfate, filtered, and evaporated to provide crude N-tritylmorpholino subunit. The subunit may be purified by silica gel chromatography.

As alternatives, base sensitive amine protecting groups may be incorporated, for example, 9-fluorenylmethylcarbonyl (using FMOC chloride in pyridine/DMF and quenching with water).

D. General procedure for the removal of alkyl and aryl groups from the morpholino nitrogen of morpholino subunits.

For morpholino subunits possessing benzylic groups at the morpholino nitrogen, the compound is hydrogenated over Pd catalyst in methanol of methanol/DMF mixtures. The secondary amine produced may be protected as in the general Example.

For morpholino subunits possessing either 4-methoxyphenyl or 4-methoxybenzyl groups at the morpholino nitrogen, the compound is dissolved in methanol or methanol/DMF mixture containing 4 molar equivalents of acetic acid and 2 molar equivalents of sodium acetate. Cerric ammonium nitrate (2 molar equivalents) is added and the reaction stirred at room temperature for 1–24 hours. After evaporation of the solvents the morpholino nitrogen may be protected as in the general Example.

EXAMPLE 2

Preparation of Morpholino Subunits from Substituted Hexopyranosides

A. General procedure for protection of the R group.

1. Protection of amino groups on heteroaromatic rings. Protection is done as in Example 1A1.

2. Protection of aliphatic or carbocyclic aromatic amines. Protection is done as in Example 1A2.

3. Protection of thiols. Protection is done as in Example 1A3.

4. Protection of alcohols. Protection is done as in Example 1A4.

B. General procedure for formation of the morpholino ring.

The morpholino ring is constructed as in Example 1B with the sole exception that 2.2 moles of sodium periodate are used in the oxidation step.

C. General procedure for protection of the morpholino ring nitrogen. The morpholino ring nitrogen is protected as in Example 1C.

D. General procedure for the removal of alkyl and aryl groups from the morpholino nitrogen of morpholino subunits.

The nitrogen is deprotected as in Example 1D.

EXAMPLE 3

Preparation of Subunits with Nucleobase Side Chains

The example illustrate the use of the D-sugars. The enantiomeric subunits may be obtained by employing the corresponding L-sugars.

A. Uracil as nucleobase.

1. Uridine was converted into the morpholino subunit 32.2b (Xi=uracil-1-yl) by the general procedure.

2. Uracil is bis-trimethylsilylated according to the procedure of Niedballa and Vorbruggeno Uracil is dissolved in benzene, and added to 1,2,3,4,6-penta-O-acetyl-β -D-glucopyranose 33.1b (Xi=β-OAc) (Niedbala and Vorbruggen) in 1,2 dichloroethane followed by tin tetrachloride in 1,2-dichloroethane according to the method of Vorbruggen and Niedballa to provide the 1-( 2,3,4,6-tetra-O-acetyl-β-D-glucopyranosyl)uracil 33.1b (Xi=β-uracil-1-yl). Following methanolysis with sodium methoxide in methanol the 1-(B-D-glucopyranosyl)uracil 33.1a (Xi=β-uracil-1-yl) is obtained. This is converted into the morpholino subunit 32.2b (Xi=β-uracil-1-yl) by the general procedure.

B. Thymine as nucleobase.

1. Ribothymidine 32.1a (Xi=β-thymin-1-yl) is prepared by the method of Tronchet, et al. It is converted into the morpholino subunit 32.2b (Xi=β-thymin- 1-yl) by the general procedure.

2. Thymine is silylated by the general procedure of Wittenberg and reacted as for uracil in the Example 3a2 above to prepare the morpholino T derivative 32.2b (Xi=β-thymin-1-yl). A wide variety of other 5-substituted uracils (halo, alkynyl, alkyl, alkenyl, nitro) may be prepared in this manner. In some cases the use of acetonitrile in the Hilbert-Johnson reaction is advantageous.

C. N4-benzoylcytosine as nucleobase.

1. Cytidine was converted into the morpholino subunit 32.2b (Xi=β-N4-benzoylcytidin-1-yl) by the general procedure.

2. The 1-(2,3,4,6-tetra-O-acetyl-β-D-glucopyranosyl)uracil from Example 3A2 is treated with phosphorus pentasulfide in benzene to provide the 4-thiouracil derivative. Reaction with triethylamine and dimethyl sulfate produce the S-alkylated species which is converted into 1-(β-D-glucopyranosyl)cytosine 33.1a (Xi=β-cytidin-1-yl) by treatment with methanolic ammonia. Following protection of the heterocyclic amine this is converted into the morpholino subunit 32.2b (Xi=β-N4-benzoylcytidin-1-yl) by the general procedure.

3. The 1-(β-D-glucopyranosyl)uracil from Example 3A2 is treated with hexmethyldisilazane by the method of Vorbruggen, et al. Following protection of the heterocyclic amine this is converted into the morpholino subunit by the general procedure.

4. Cytosine is silylated by the general method of Wittenberg. It is reacted with 1,2,3,4,6-penta-O-acetyl-β -D-glucopyranose in 1,2 dichloroethane followed by tin tetrachloride in 1,2-dichloroethane (or acetonitrile) according to the method of Vorbruggen and Niedballa to provide the 1-(2,3, 4,6-tetra-O-acetyl-β-D-glucopyranosyl)cytosine 33.1b (Xi= β-cytidin-1-yl). Following methanolysis with sodium methoxide in methanol the 1-(β-D-glucopyranosyl) cytosine is obtained. Following protection of the heterocyclic amine this is converted into the morpholino subunit 32.2b (Xi=β-N4-benzoylcytidin-1-yl) by the general procedure.

D. N4-Benzoyladenine as nucleobase.

1. Adenosine was converted into the morpholino subunit 32.2b (Xi=β-N6-benzoyladenin-1-yl) by the general procedure.

2. N-6-Benzoyl-9-(2,3,4,6-tetra-O-acetyl-β-D-glucopyranosyl)adenine (Lichtenhaler, et al.) is treated with 2:1 ammonium hydroxide/DMF at 45 degrees C. for 15 hours to give 9-(β-D-glucopyranosyl)adenine 33.1a (Xi=β-adenin-9-yl). The amino group is protected as in the general Example and the morpholino subunit 32.2b (Xi=β-N4-benzoyladenin-9-yl) produced by the general procedure for hexopyranosides. A more direct method for the conversion of the glucoside into the morpholino subunit employs the selective O-deacylation procedure of Rammler and Khorana on N-6-Benzoyl- 9-(2,3,4,6-tetra-O-acetyl-β-D-glucopyranosyl)adenine to give N-6-Benzoyl-9-(β-D-glucopyranosyl)adenine which is converted into the morpholino subunit by the general procedure.

E. Hypoxanthine as nucleobase

1. Inosine was converted into the morpholino subunit 32.2b (Xi=β-hypoxanthin-9-yl) by the general procedure for ribofuranosides.

2. Inosine is silylated by the general procedure of Wittenberg. It is reacted with 1,2,3,4,6-penta-O-acetyl-β -D-glucopyranose in 1,2 dichloroethane followed by tin tetrachloride in 1,2-dichloroethane (or acetonitrile) to prepare 9-(2,3,4,6-tetra-O-acetyl-β-D-glucopyranosyl)hypoxanthine 33.1b (Xi=β-hypoxanthin-9yl). Methanolysis of the esters and application of the standard procedure for morpholino ring synthesis produce the subunit 32.2b (Xi=β-hypoxanthin-9-yl).

F. N2-Phenylacetylguanine as nucleobase.

1. Guanosine was converted into the morpholino subunit 32.2b (Xi=β-N-2-phenylacetylguanin-9-yl) by the general procedure for ribofuranosides.

2. N-2-Acetyl-9-(2,3,4,6-tetra-O-acetyl-β-D-glucopyranosyl)guanine (Lichtenhaler, et al.) was treated with 2:1 ammonium hydroxide/DMF at 45 degrees C. for 15 hours. The amino group is protected as in the general Example and the morpholino subunit 32.2b (Xi= β-N-2-phenylacetylguanin-9-yl) produced by the general procedure for hexopyranosides.

EXAMPLE 4

Preparation Subunits with Modified Nucleobase Side Chains

A variety of pyrimidines, purines, and their analogs may be converted into the corresponding ribofuranosides and hexopyranosides by the methods of Niedballa and Vorbruggen and by the methods of Lichtenhaler, et al. These may be further processed to morpholino subunits as per the examples below.

A. 6-Methyluracil as side chain. 6-Methyluridine (Winkley and Morris) is converted into the N-tritylated morpholino subunit by the general procedure to give 32.2b (Xi=β-6-methyluracil-1-yl).

B. N3,6-Dimethyluracil as side chain. Treatment of 32.2b (Xi=β-6-methyluracil-1-yl) from Example 4A with methyl iodide and DBU in DMF affords the N-3 methylated derivative 32.2b (Xi=β-N3,6-dimethyluracil-1-yl).

C. 6-Methylcytosine as side chain.

1. 6-Methylcytidine (Winkley and Robins) is converted into the morpholino subunit 32.2b (Xi=β-6-methylcytosin-1-yl) by the general procedure.

2. Treatment of 32.2b (Xi=β-6-methyluracil-1-yl) from Example 4A with TBDMS-Cl in pyidine followed by tri-isopropylbenzenesulfonyl chloride in methylene chloride containing triethylamine provides the O-4 sulfonated species which is converted into 32.2b (Xi=β-N4-benzoyl-6-methylcytosin-1-yl) by treatment with ammonia in DMF followed by protection of the base by the standard procedure and silyl cleavage.

D. N4,6-Dimethylcytosine as side chain. Treatment of 32.2b (Xi=β-6-methyluracil-1-yl) from Example 4A with TBDMS-Cl in pyidine followed by triisopropylbenzene-sulfonyl chloride in methylene chloride containing triethylamine provide the O-4 sulfonated species which is converted into 32.2b (Xi= β-N4-benzoyl-N4,6-dimethylcytosin-1-yl) by treatment with methylamine in DMF followed by protection of the base by the standard procedure and silyl cleavage.

E. N6,N6-dimethyladenine as side chain. Inosine was converted into the N-tritylated morpholino subunit 32.2b (Xi= hypoxanthin-9-yl) by the general procedure. Following conversion into the 5-t-butyldimethylsilyl ether using TBDMS-Cl in pyridine, treatment with triisopropylbenzenesulfonyl chloride in methylene chloride containing triethylamine provide the O-6 sulfonated species which is converted into 32.2b (Xi= β-N6,N6-dimethyladenin-9-yl) by treatment with dimethylamine in DMF and silyl cleavage.

F. 8-Methylhypoxanthine as side chain. 8-Methylhypoxanthine (Koppel and Robins) is silylated by the general procedure of Wittenberg and converted into 8-methyl-9-(2,3,5-Tri-O-benzoyl-beta-D-ribofuranosyl)hypoxanthine 32.1b (Xi=β-8-methylhypoxanthin- 9-yl) by the method of Lichtenhaler, et al. This product is converted into the morpholino subunit 32.2b(Xi=β-8-methylhypoxanthin-9-yl) produced by the general procedure for ribofuanosides.

G. 8-Methylhypoxanthine as side chain. The hypoxanthine morpholino subunit from Example 3E is treated with 1.1 equivalents of sodium hydride in DMF followed by methyl iodide to produce the 1,8-dimethylhypoxanthine morpholino subunit 32.2b (β-N1-methylhypoxanthin- 9-yl). The use of other alkyl groups allows the formation of other 1-alkyated hypoxanthine subunits.

H. N1,8-Dimethylhypoxanthine as side chain. The 8-methylhypoxanthine morpholino subunit from Example 4F is treated with 1.1 equivalents of sodium hydride in DMF followed by methyl iodide to produce the 1,8-dimethylhypoxanthine morpholino subunit 32.2b (β-N1,8-dimethylhypoxanthin- 9-yl).

I. 8-Bromo-N2-phenylacetylguanine as side chain. The guanosine is brominated by stirring with N-bromosuccinimide in DMF at room temperature by the method of Srivastava and Nagpal. This is converted into the morpholino subunit 32.2b (Xi=β-8-bromo-N2-phenylacetylguanin- 9-yl) by protection of the amine, morpholino ring synthesis and tritylation as per the general proceudres. The 8-bromoadenine and 8-bromohypoxanthine species may be prepared similarly.

J. 8-Methylthio-N2-phenylacetylguanine as side chain. The 8-bromoguanine derivatives in Example 4I are converted into the 8-methylthio species by reaction with sodium thiomethoxide in DMF. The 8-bromoadenine and 8-bromohypoxanthine species may be similarly converted.

EXAMPLE 5

Preparation of Subunits with Non-Nucleobase Side Chains

A. Methyl 4(5)-methylimidazole-5(4)-carboxylate as side chain.

Methyl 4(5)-methylimidazole-5(4)-carboxylate is silylated and reacted with an equimolar amount of 1,2,3,4,6-penta-O-acetyl-β-D-glucopyranose by the method of Cook, et al., using at least 1.44 mole of stannic chloride per mole sugar yields the acetylated sugar. Methanolysis with sodium methoxide in methanol provides methyl 5-methyl-1-(β-D-glucopyranosyl)imidazole- 4-carboxylate 33.1a (Xi=4-methoxycarbonyl- 5-methylimadzol-1-yl. This may be converted into the morpholino subunit 32.2b (Xi=β-4-methoxycarbonyl- 5-methylimadzol-1-yl) by the standard procedure.

B. 2-Oxo-1,2-dihyropyridin-1-yl as side chain.

The pyridone ribofuranoside 32.1a (Xi=β-2-oxo- 1,2-dihyropyridin-1-yl) (Pischel and Wagner) is conveted into the corresponding morpholino subunit 32.2b (Xi=β-2-oxo-1,2-dihyropyridin-1-yl) by the standard procedures.

C. 2-Oxo-1,2-dihyropyrimidin-1-yl as side chain.

The pyrimidone ribofuranoside 32.1a (Xi=β-2-oxo- 1,2-dihyropyrimidin-1-yl) (Holy, et al) is conveted into the corresponding morpholino subunit 32.2b (Xi=β- 2-oxo-1,2-dihyropyrimidin-1-yl) by the standard procedures.

D. Benzimidazole as side chain.

The benimidazole containing ribofuranoside 32.1a (Xi= β-benzimidazol-1-yl) prepared by the method of Southon and Pfleiderer is converted into the morpholino subunit 32.2b (Xi=β-benzimidazol-1-yl) by the standard procedure.

E. Phenyl as side chain.

The methods below may be used to prepare a wide variety of aryl substutitued morpholino subunits.

1. 34.1a (Xi=C$_6$H$_5$) The C-phenyl glycoside 33.1a (Xi= β-phenyl) prepared by the method of Czernecki and Ville is converted into the morpholino subunit 32.2b (Xi=β-phenyl) by the general procedure.

2. 34.2a (Xi=C$_6$H$_5$) 3,4,6-Tri-O-benzyl-1,2-anhydro-β -D-mannopyranose was reacted with lithium diphenyl cuprate (Posner) using the procedure of Bellosta and Czernecki. The phenyl mannopyranoside 33.3d (Xi=β-phenyl) is hydrogenated to remove the benzyl groups and converted into the morpholino subunit by the standard procedure to provide 34.2a (Xi=α-phenyl).

3. 34.3a (Xi=C$_6$H$_5$) This is made from L-mannose by the procedure in 4E2.

4. 34.4a (Xi=C$_6$H$_5$) This is made from L-glucose by the procedure in 4E1.

F. Alkyl as side chain.

The methods below may be used to prepare a wide variety of alkyl or aralkyl (for example, benzyl or phenethyl) substutitued morpholino subunits.

1. 34.1a (Xi=CH$_3$) The C-methyl glycoside 33.1b (Xi=β-methyl) prepared by the method of Bellosta and Czernecki is converted into the morpholino subunit 32.2b (Xi=β-methyl) by the general procedure.

2. 34.2a (Xi=CH$_3$) 3,4,6-Tri-O-benzyl-1,2-anhydro-β -D-mannopyranose was reacted with lithium dimethyl cuprate (Posner) using the procedure of Bellosta and Czernecki. The methyl mannopyranoside 33.3d (Xi=α-ethyl) is hydrogenated to remove the benzyl groups and converted into the morpholino subunit by the standard procedure to provide 34.2a (Xi=α-methyl).

3. 34.3a (Xi=CH₃) This is made from L-mannose by the procedure in 4E2.

4. 34.4a (Xi=CH₃) This is made from L-glucose by the procedure in 4E1.

G. Aliphatic side chains bearing bearing hydroxy groups.

1. Hydroxymethyl.

a. 34.1a (Xi=CH$_2$OTBDPS): The vinyl glucopyranoside 33.1d (Xi=β-ethenyl), prepared by the method of Kraus and Molina is ozonolyzed in a mixture of methanol and ethyl acetate and after removal of the ozone the reaction is quenched with sodium borohydride in methanol to provide the alcohol 33.1d (Xi=β-CH$_2$OH). This is converted into the t-butyldiphenylsilyl ether by the general procedure. Catalytic hydrogenation removes the benzyl protecting groups and the molecule is converted into the morpholino subunit 34.1a [32.2b] (Xi=β-CH$_2$OTBDPS) by the general procedure.

b. 34.2a (Xi=CH$_2$OTBDPS): 3,4,6-Tri-O-benzyl- 1,2-anhydro-β-D-mannopyranose is reacted with lithium divinyl cuprate (Posner) (REF) using the procedure of Bellosta and Czernecki. The vinyl mannopyranoside 33.3d (Xi=β-ethenyl) is further treated as per the procedure in Example 4G1a to provide 34.2a (Xi= CH$_2$OTBDPS).

c. 34.3a (Xi=CH$_2$OTBDPS): The alcohol 33.1d (Xi=β-CH$_2$OH) prepared as in Example 4G1a is converted into the t-butyldiphenylsilyl ether by the general procedure. Catalytic hydrogenation removes the benzyl groups. The glcoside is converted to the "α-morpholino" subunit 34.3a (Xi=CH$_2$OTBDPS) by the procedure in Summerton, et al (U.S. Pat. No. 5,235,033). This compound may also be prepared by application of the procedures in Example 4G1b to L-mannose.

d. 34.4a (Xi=CH$_2$OTBDPS): The hydroxymethyl glucopyranoside 33.1d (Xi=β-CH$_2$OH) prepared as in Example 4G1a is reacted with trimethylacetyl chloride in pyridine. Catalytic hydrogenation removes the benzyl protecting groups and the molecule is converted into the morpholino subunit 32.2b (Xi=β-CH$_2$OCO-C(CH$_3$)$_3$) by the general procedure. The free alcohol is silylated according to the general procedure and the product is treated with lithium aluminum hydride in THF to prepare the free alcohol 34.4a (Xi=CH$_2$OTBDPS). This compound may also be obtained by application of the procedures in Example 4G1a to L-glucose.

2. Hydroxyethyl.

a. 34.1 (Y=CH$_2$OH, Xi=CH$_2$CH$_2$OTBDPS): The tetrabenzylated hydroxyethyl derivative 33.1d (Xi=β-CH$_2$CH$_2$OH) prepared by the method of Allevi, et al, is protected as the t-butyldiphenylsilyl ether by the general procedure, the benzyl groups removed by catalytic hydrogenation over Pd on charcoal, and the morpholino ring formed by the general procedure. Alternatively, the vinyl glucopyranoside 33.1d (Xi=β-ethenyl) from Example 4G1a is treated with borane-THF followed by alkaline hydroperoxide to yield the tetrabenzylated starting material.

b. 34.2 (Y=CH$_2$OH, Xi=CH$_2$CH$_2$OTBDPS): The tetrabenzylated hydroxyethyl derivative 33.1d (Xi=α-CH$_2$CH$_2$OH), prepared by the method of Allevi, et al, is protected as the t-butyldiphenylsilyl ether by the general procedure, the benzyl groups removed by catalytic hydrogenation over Pd on charcoal, and the morpholino ring formed by the general procedure. Alternatively, the vinyl mannopyranoside 33.3d (Xi=α-ethenyl) from Example 4G1b is reacted with sodium hydride in DMF with benzyl chloride, then treated with borane-THF followed by alkaline hydroperxide to yield the 33.1d (Xi=αCH$_2$CH$_2$OH). This is protected as the t-butyldiphenylsilyl ether by the general procedure, the benzyl groups removed by catalytic hydrogenation over Pd on charcoal, and the morpholino ring formed by the general procedure.

c. 34.3 (Y=CH$_2$OH, Xi=CH$_2$CH$_2$OTBDPS): Is prepared from L-glucose or L-mannose by the methods in Example 4G2b.

d. 34.4 (Y=CH$_2$OH, Xi=CH$_2$CH$_2$OTBDPS): Is prepared from L-glucose by the methods in Example 4G2a.

3. Hydroxypropyl.

a. 34.1 (Y=CH$_2$OH, Xi=CH$_2$CH$_2$CH$_2$OTBDPS): Xanthate 32.1 (R$_2$,R$_3$=isopropylidene, R$_5$=benzoyl, Xi=O-CS-SCH$_3$) (Araki, et al. ) is reacted with methyl acrylate in the presence of tributyltin hydride and 2,2'-azobis (isobutyronitrile) as initiator to produce the C-riboside ester 32.1 (R$_2$, R$_3$=isopropylidene, R$_5$=benzoyl, Xi=CH$_2$CH$_2$CO$_2$CH$_3$). Treatment with methanolic HCl gave the free triol which was converted into the morpholino subunit 32.2b (Xi=β-CH$_2$CH$_2$CO$_2$CH$_3$) by the standard procedure. Protection of the hydroxy group as the benzyloxymethyl ether (Stork and Isobe) followed by treatment with lithium aluminum hydride in THF, then silylation as in the standard procedure, and catalytic hydrogenation provides the desired protected alcohol 34.1 (Y=CH$_2$OH, Xi=CH$_2$CH$_2$CH$_2$OTBDPS).

b. 34.2 (Y=CH$_2$OH, Xi=CH$_2$CH$_2$CH$_2$OTBDPS): Ester 33.1b (Xi=α-CH$_2$CH$_2$CO$_2$CH$_3$) (Adlington, et al.) is reacted with methanolic HCl to give the free tetraol which was converted into the morpholino subunit 32.2b (Xi=α-CH$_2$CH$_2$CO$_2$CH$_3$) by the standard procedure. Protection of the hydroxy group as the benzyloxymethyl ether (Stork and Isobe) followed by treatment with lithium aluminum hydride in THF, then silylation as in the standard procedure, and catalytic hydrogenation provides the desired protected alcohol 34.2 (Y=CH$_2$OH, Xi= CH$_2$CH$_2$CH$_2$OTBDPS).

a. 34.3 (Y=CH$_2$OH, Xi=CH$_2$CH$_2$CH$_2$OTBDPS): Is prepared from L-glucose by the methods in Example 4G3b.

a. 34.4 (Y=CH$_2$OH, Xi=CH$_2$CH$_2$CH$_2$OTBDPS): Is prepared from L-ribose by the methods in Example 4G3a.

4. Homologous ω-hydroxyalkyl derivatives. Higher order alcohols 34.1–34.4 (Y=CH$_2$OH, Xi=CH$_2$[CH$_2$]$_n$CH$_2$OTBDPS) may be made by the following procedure from lower order alcohols: The hydroxymethyl group of 34.1–34.4 (y=CH$_2$OH, Xi=[CH$_2$]$_n$OTBDPS) is protected as the benzyloxymethyl ether by the method of Stork and Isobe, then the TBDPS group is removed with tetrabutylammonium fluoride. The alcohol is converted into a tosylate and reacted with sodiodiethylmalonate in DMSO. The ester is saponified, acidified and decarboxylated. Following treatment with trityl chloride in DMF to replace any trityl cleaved in the process, the acid is reduced with lithium aluminum hydride in THF, the alcohol silylated by the standard procedure to provide 34.1–34.4 (Y= CH$_2$OH, Xi= [CH$_2$]$_{n+2}$OTBDPS).

5. Other alcohol containing side chains. The hydroxyymethyl group of 34.1–34.4 (Y=CH$_2$OH, Xi= [CH$_2$]$_n$OTBDPS) is protected as the benzyloxymethyl ether by the method of Stork and Isobe, then the TBDPS group is removed with tetrabutylammonium fluoride. The alcohol is converted into an aldehyde with diisopropylcarbodiimide in DMSO containing a small amount of pyridinium methanesulfonate. The aldehyde may be reacted with any of a large variety of Grignard or organolithium reagents to provide secondary alcohols. These may be silylated by the general procedure and the hydroxymethyl freed by hydrogenolysis. The secondary alcohols may by oxidized to ketones which may be reacted again with any of a large variety of Grignard or organolithium reagents to provide tertiary alcohols. These typically do not require protection and the final subunit may be prepared by hydrogenolysis.

H. Aliphatic side chains containing carbon-carbon double bonds. The hydroxyymethyl group of 34.1–34.4 (Y=CH$_2$OH, Xi=[CH$_2$]$_n$OTBDPS) is protected as the benzoate ester then the TBDPS group is removed with tetrabutylammonium fluoride. The alcohol is converted into the aldehyde with diisopropylcarbodiimide in DMSO containing a small amount of pyridinium methanesulfonate. The aldehyde may be reacted with any of a large variety of Wittig reagents (Maercker) to produce alkenes. For example, reaction of 34.1 (Y= CH$_2$OBz, Xi=CHO) with isopropylidene triphenylphosphorane (prepared from isopropyltriphenylphosphonium bromide and butyllithium in THF) provides the alkene 34.1 (Y=CH$_2$OBz, Xi= CH=C(CH$_3$)$_2$). This is converted into the morpholino subunit 34.1 (Y=CH$_2$OH, Xi=CH=C(CH$_3$)$_2$) by saponification.

Similarly, reaction with benzylidene triphenylphosphorane (prepared from benzyltriphenylphosphonium chloride and butyllithium in THF) followed by saponification provides the morpholino subunit 34.1 (Y=CH$_2$OH, Xi=CH=CHPhenyl), the isomers of which may be separated by silica gel chromatography.

Subunits 34.2–34.4 with aliphatic side chains containing carbon-carbon double bonds are prepared in a similar fashion.

I. Aliphatic side chains containing carboxylic acids and esters.

Alcohol 34.1 (Y=CH$_2$OH, Xi=[CH$_2$]$_n$OTBDPS) is treated with 80% acetic acid in water followed by reaction with benzyl chloroformate to provide the carbamate 34.1c (Xi= [CH$_2$]$_n$OTBDPS). The alcohol is protected as the benzyloxymethyl ether by the method of Stork and Isobe, then the TBDPS group is removed with tetrabutylammonium fluoride. The hydroxymethyl group is converted into a carboxyl by oxidation with potassium permanganate or pyridinium dichromate. The acids are protected by conversion into the ester by treatment with diisopropylcarbodiimide, 4-dimethylaminopyridine and either methyl alcohol or 2-(phenylsulfonyl)ethyl alcohol in dichloromethane. Treatment with hydrogen and Pd on charcoal followed by tritylation of the morpholino nitrogen prepares the morpholino subunits.

Similar procedures may be performed on the acids 34.1–34.4 (Y=CH$_2$OH, Xi=[CH$_2$]$_n$OTBDPS) to prepare the corresponding acid. Other alcohols may be employed to produce a large variety of esters.

J. Aliphatic side chains containing carboxylic acid amides. The acids prepared in part I above are reacted with diisopropylcarbodiimide and morpholino in dichloromethane to produce the morpholino amide. Conversion to the subunit follows hydrogenolytic cleavage of the carbamate and acetal with Pd on charcoal. Other amides may be prepared by use of ammonia or other amines.

K. Aliphatic side chains containing amines.

1. From alcohol derivatives. The hydroxyymethyl group of 34.1–34.4 (Y=CH$_2$OH, Xi=[CH$_2$]$_n$OTBDPS) is protected as the benzyloxymethyl ether by the method of Stork and Isobe, then the TBDPS group is removed with tetrabutylammonium fluoride. The alcohol is converted into an aldehyde with diisopropylcarbodiimide in DMSO containing a small amount of pyridinium methanesulfonate. The alcohol is treated with triphenylphosphine, sodium or lithium azide and carbon tetrabromide in DMF to produce the azide by the method of Yamamato, et al. Catalytic reduction with Pd on charcoal in the presence of ammonia provides the amine and frees the alcohol. The amine is protected as the general procedure.

2. From alcohols via oxidation to the aldehyde and reductive amination. The hydroxyymethyl group of 34.1–34.4 (y=CH$_2$OH, Xi=[CH$_2$]$_n$OTBDPS) is protected as the benzyloxymethyl ether by the method of Stork and Isobe, then the TBDPS group is removed with tetrabutylammonium fluoride. The alcohol is converted into an aldehyde with diisopropylcarbodiimide in DMSO containing a small amount of pyridinium methanesulfonate. The aldehyde is treated with a large excess of the appropriate amine in methanol at pH=6 in the presence of sodium cyanoborohydride. The resulting amine is protected as in the general Examples and the acetal cleaved by hydrogenolysis. Additionally, the ketones prepared in Example 4G5 may be employed as starting materials for the production of more amines species.

L. Preparation of thiol derivatives.

The hydroxyymethyl group of 34.1–34.4 (Y=CH$_2$OH, Xi=[CH$_2$]$_n$OTBDPS) is protected as the benzoate ester then the TBDPS group is removed with tetrabutylammonium fluoride. The alcohol is converted into the tosylate by treatment with p-toluenesulfonyl chloride in pyridine. The tosylate group is displaced with thiourea to give the thiol which is protected by conversion into the S-ethyl disulfide by the general method. The benzoate group is removed by saponification.

M. Hydrogen as side chain.

1. (S)-4-Trityl-2-hydroxymethylmorpholino 32.2b (Xi= H) is prepared from the (S)-4-tert-butoxycarbonyl- 2-hydroxymethylmorpholino prepared by Yanagisawa and Kanazaki, by cleavage of the Boc group in 50% trifluoroacteic acid in dichloromethane followed by retritylation by the general method.

2. (R)-4-Trityl-2-hydroxymethylmorpholine 32.2b (Xi= H) is prepared from the (R)-4-tert-butoxycarbonyl- 2-hydroxymethylmorpholine prepared by Yanagisawa and Kanazaki, by cleavage of the Boc group in 50% trifluoroacteic acid in dichloromethane followed by retritylation by the general method.

EXAMPLE 6

Synthetic Strategies for Stereochemical Control of R and Y Groups of Morpholino Subunits Examples 3 and 4 above generally illustrate the preparation of morpholino subunits with nucleobase or modified nucleobase side chains with groups R and Y in FIG. 6 both in the β position (FIG. 34.1). This derives principally from the use of D-glucose or D-galactose or D-ribose and their derivatives as precursors. For the preparation of the enantiomeric subunits, that is, morpholino subunits with groups R and Y in FIG. 6 both in the α position (species 34.4), corresponding L-sugars are employed.

For the preparation of morpholino subunits with nucleobase or modified nucleobase side chains with groups Y in FIG. 6 in the β position, and group R in the α position (species 34.3), it is preferred to use the method of Chow and Danishefsky. In this procedure silylated nucleobases and modified nucleobases are reacted with 3,4,6-tri-O-TBDMS-1,2-anhydro-β-D-mannopyranose to give the O-TBDMS-α-D-glycosides which are converted into the morpholino subunits 34.3 following desilylation with tertabutylammonium fluoride. For the preparation of morpholino subunits with nucleobase or modified nucleobase side chains with groups Y in FIG. 6 in the α position, and group R in the β position (species 34.4), it is preferred to use the method of Chow and Danishefsky. In this procedure silylated nucleobases and modified nucleobases are reacted with 3,4,6-tri-O-TBDMS-1,2-anhydro-β-L-mannopyranose to give the O-TBDMS-α-

L-glycosides which are converted into the morpholino subunits 34.4 following desilylation with tertabutylammonium fluoride.

EXAMPLE 7

Preparartion of Morpholino Subunits with Representative Y and Z

A. 7.1 (Xi=β-N4-benzoylcytosin-1-yl).

The alcohol 32.2b (Xi=β-N4-benzoylcytosin-1-yl) is oxidized to the aldehyde 7.1 (Xi=β-N4-benzoylcytosin- 1-yl) with diisopropyl carbodiimide in DMSO containing a small amount of pyridinium methanesulfonate.

B. 7.2 (X=OH, Xi=β-N4-benzoylcytosin-1-yl).

The aldehyde from Example 7A is oxidized with potassium permanganate in acetone or t-butanol/dioxane/water buffered with magnesium sulfate to the acid 7.2 (X=OH, Xi=β-N4-benzoylcytosin-1-yl). Higher yields may be obtained if the trityl group in the alcohol 32.2b (Xi=β-N4-benzoylcytosin-1-yl) is replaced with a CBz group. Oxidation with permanganate, hydrogenolysis of the CBz group, and retritylation prepare the acid needed for activation.

C. 7.2 (X=O-p-nitrophenyl, Xi=β-N4-benzoylcytosin-1yl).

The acid from Example 7B is reacted with p-nitrophenol and diisopropyl carbodiimide in dichloromethane to produce the ester 7.2 (X=O-p-nitrophenyl, Xi=β-N4-benzoylcytosin-1-yl) suitable for coupling reactions.

D. 7.2 (X=imidazol-1-yl, Xi=β-N4-benzoylcytosin-1yl).

Reaction of the acid with carbonyl diimidazole produces the imidazolide 7.2 (X=imidazol-1-yl, Xi=β-N 4-benzoyl-cytosin-1-yl) suitable for coupling reactions.

E. 7.3 (X=Cl, Xi=β-N6-benzoyladenin-1-yl).

The alcohol 32.2b (Xi=β-N6-benzoyladenin-1-yl) is converted into the tosylate using tosyl chloride and pyridine. This is reacted with thiourea in methanol to provide the thiol deriviative. This may be oxidized to the sulfonic acid using potassium permanganate in acetone or t-butanol/dioxane/water buffered with magnesium sulfate. Higher yields in the oxidation are obtained if the trityl group is replaced by the benzyloxycarbonyl group. The sulfonic acid is isolated as its triethylamonium salt by extraction into chloroform from water saturated with triethylamine hydrochloride. The salts of sulfonic acids can be easily chromatographed on silica gel using triethylamine/methanol/chloroform mixtures if the silica is first pre-eluted with 2% triethylamine in chloroform. Retritylation may be efected by hydrogenolysis with Pd on charcoal to remove the carbamate followed by tritylation by the general procedure. For activation, ten mmole of the triethylamine salt of sulfonate subunit is dissolved in 10 ml of dichloromethane and then 40 mmole of pyridine is added. This solution is chilled for 15 minutes on a bed of dry ice and then 11 mmole of phosgene (20% in Toluene) is slowly added while the solution is rapidly stirred. After addition the solution is allowed to come to room temperature and then washed with aqueous $NaHCO_3$, dried, and chromatographed on silica gel eluting with a mixture of chloroform and acetone to give the desired sulfonyl chloride 7.3 (X=Cl, Xi=β-N- 6-benzoyladenin-1-yl).

F. 7.4 (X=OH, Xi=α-methyl).

The alcohol 32.2b (Xi=α-methyl) is oxidized to the aldehyde 7.1 (Xi=α-methyl) with diisopropyl carbodiimide in DMSO containing a small amount of pyridinium methanesulfonate. This is reacted with 2,6-dithianylidene-triphenylphosphorane by the method of Kruse, et al. The resulting ketenedithioacetal is converted into the carboxylic acid by hydrolysis with mercuric chloride in wet acetonitrile to give the subunit 7.4 (X=OH, Xi=α-methyl), which can be chromatographed on silica gel using triethylamine/methanol/chloroform mixtures if the silica is first pre-eluted with 2% triethylamine in chloroform.

G. 7.4 (X=O-p-nitrophenyl, Xi=α-methyl).

The acid salt from the previous example is activated by treatment with diisopropylcarbodiimide in dichloromethane containing p-nitrophenol containing 1 equivalent of pyridinium p-toluenesulfonate.

H. 7.5 (X=OH, Xi=α-methyl).

Benzyl α-bromoacetate is reacted with triphenylphosphine and the phosphonium salt product is reacted with sodium hydroxide to produce the ylid. This is reacted with aldehyde 7.1 (Xi=α-methyl), produced from alcohol 32.2b Xi=α-methyl) as in Example 7A, to give the unsaturated ester. Treatment with hydrogen and Pd on charcoal yields the acid 7.5 (X=OH, Xi=α-methyl), which can be chromatographed on silica gel using triethylamine/methanol/chloroform mixtures if the silica is first pre-eluted with 2% triethylamine in chloroform.

I. 7.5 (X=O-p-nitrophenyl, Xi=α-methyl).

The acid salt from the previous example is activated by treatment with diisopropylcarbodiimide in dichloromethane containing p-nitrophenol containing 1 equivalent of pyridinium p-toluenesulfonate.

J. 7.6 (X=O-p-nitrophenyl, Y=O, Xi=β-N2-phenylacetylguanin- 9-yl).

Dry, N-protected, 5'-hydroxyl morpholino subunit 32.2b (Xi=β-N2-phenylacetylguanin-9-yl) (1 mmol), is treated with bis-(p-nitrophenyl)carbonate (BNPC) and triethylamine (TEA) in DMF under anhydrous conditions. The solution is stirred for three hours, then evaporated to dryness. The residue is dissolved in chloroform and chromatographed on silica gel eluting with a chloroform/methanol mixture to give activated subunit.

K. 7.6 (X=imidazol-1-yl, Y=S, Xi=β-N2-phenylacetylguanin- 9-yl).

Dry, N-protected, 5'-hydroxyl morpholino subunit 32.2b (Xi=β-N2-phenylacetylguanin-9-yl) is treated with thiocarbonyldiimidazole in pyridine at room temperature for 12 hours. Water is added to quench the reagents, the solvents evaporated and the residue is dissolved in chloroform and chromatographed on silica gel eluting with an a chloroform/methanol mixture to give activated subunit.

L. 7.7 (X=Cl, Xi=β-$CH_2CH_2OTBDPS$).

An N-tritylated morpholino subunit 32.2b (Xi=β-CH 2CH2OTBDPS) is detritylated by treatment with 2% dichloroacetic acid in dichloromethane followed by addition to ether to precipitate the product salt. The crude salt is dissolved in dichloromethane/pyridine and treated with 3 equivalents of dimethoxytrityl chloride. The solvents are evaporated and the residue taken up in 1:1 methanol/acetic acid to cleave the DMT group on the nitrogen. The solvents are removed, the residue dissolved in dichloromethane, washed with water, sodium bicarb solution and brine. The solution is dried over sodium sulfate, filtered and evaporated to give a residue which is purified by chromatography on silica gel eluting with a chloroform/methanol mixture. The free morphline is sulfated by treatment with $SO_3$/pyridine complex (with excess pyridine) in dimethylformamide (DMF). It should be mentioned that the salts of sulfamic acids can be easily chromatographed on silica gel using triethylamine/methanol/chloroform mixtures if the silica is first pre-eluted with 2% triethylamine in chloroform. For activation, ten mmole of the triethylamine salt of sulfated subunit is dissolved in 10 ml of dichloromethane and then 40 mmole of pyridine is added. This solution is chilled for 15 minutes on a bed of dry ice and then 11 mmole of phosgene (20% in Toluene) is slowly added while the solution is rapidly stirred. After addition the solution is allowed to come to room temperature and then washed with aqueous $NaHCO_3$, dried, and chromatographed on silica gel eluting with a mixture of chloroform and acetone to give the desired sulfamoyl chloride 7.7 (X=Cl, Xi= CH2CH2OTBDPS).

M. 7.8 (R'=H, X=Cl, Xi=β-uracil-1-yl).

The alcohol derivative 32.2b (Xi=β-uracil-1-yl) is treated with triphenylphosphine, sodium azide and carbon tetrabromide in DMF to produce the azide by the method of Yamamato, et al. This may be reduced by either triphenylphosphine and ammonia, or catalytic hydrogenation over Pd and charcoal. The amine is sulfated by treatment with $SO_3$/pyridine complex (with excess pyridine) in dimethylformamide (DMF). It should be mentioned that the salts of sulfamic acids can be easily chromatographed on silica gel using triethylamine/methanol/chloroform mixtures if the silica is first pre-eluted with 2% triethylamine in chloroform.

For activation, ten mmole of the triethylamine salt of sulfated subunit is dissolved in 10 ml of dichloromethane and then 40m mole of pyridine is added, This solution is chilled for 15 minutes on a bed of dry ice and then 11 mmole of phosgene (20% in Toluene) is slowly added while the solution is rapidly stirred. After addition the solution is allowed to come to room temperature and then washed with aqueous $NaHCO_3$, dried, and chromatographed on silica gel eluting with a mixture of chloroform and acetone to give the desired sulfamoyl chloride.

N. 7.8 (R'=$CH_3$, X=Cl, Xi=β-uracil-1-yl).

The alcohol derivative 32.2b (Xi=β-uracil-1-yl) is oxidized to the aldehyde with diisopropyl carbodiimide in DMSO containing a small amount of pyridinium methanesulfonate. The aldehyde may be reacted with metylamine in buffered (p-nitrophenol) methanol at pH=7 in the presence of sodium cyanoborohydride to give the morpholine-2-methanamine derivative. The amine is sulfated by treatment with $SO_3$/pyridine complex (with excess pyridine) in dimethylformamide (DMF). It should be mentioned that the salts of sulfamic acids can be easily chromatographed on silica gel using triethylamine/methanol/chloroform mixtures if the silica is first pre-eluted with 2% triethylamine in chloroform.

For activation, ten mmole of the triethylamine salt of sulfated subunit is dissolved in 10 ml of dichloromethane and then 40 mmole of pyridine is added. This solution is chilled for 15 minutes on a bed of dry ice and then 11 mmole of phosgene (20% in Toluene) is slowly added while the solution is rapidly stirred. After addition the solution is allowed to come to room temperature and then washed with aqueous $NaHCO_3$, dried, and chromatographed on silica gel eluting with a mixture of chloroform and acetone to give the desired sulfamoyl chloride.

O. 7.9 (X=Cl, Y=O, Z=$N(CH_3)_2$, Xi=β-phenyl).

One mmole of 5'-hydroxyl subunit 34.1a (Xi=phenyl), protected and tritylated on the morpholino nitrogen is dissolved in 5 ml of dichloromethane. Six mmole of N,N-diethylaniline and 2 mmole of dimethylaminodichlorophosphate (OP$(Cl)_2$N$(CH_3)_2$) is added to the solution followed by the addition of 0.5 mmole of either N-methylimidazole, tetrazole, or 4-methoxypyridine-N-oxide. After the reaction is complete (assessed by thin layer chromatography) the reaction solution may be washed with aqueous $NaH_2PO_4$. The activated subunit is isolated by chromatography on silica gel developed with acetone/chloroform or ethyl acetate/dichloromethane mixtures. Alternatively, the reaction mixture is placed on the top of a silica column and chormatographed without workup. The dimethylaminodichlorophosphate used in the above procedure was prepared as follows: a suspension containing 0.1 mole of dimethylamine hydrochloride in 0.2 mole of phosphorous oxychloride was refluxed for 12 hours and then distilled (boiling point is 36° C. at 0.5 mm Hg).

P. 7.9 (X=Cl, Y=S, Z=O-ethyl, Xi=β-phenyl).

One mmole of 5'-hydroxyl subunit 34.1a (Xi=β-phenyl) is reacted with ethyl dichlorothiophosphate according to the conditions in Example 7O.

Q. 7.10 (X=p-nitrophenyl, Xi=β-N4-benzoylcytosin-1-yl).

1. The N-tritylated morpholino subunit derivative 32.2b (Xi=β-N4-benzoylcytosin-1-yl) is detrylated using 2% acetic acid in 20% trifluoroethanol/dichloromethane. The resulting secondary amine is reacted with isoamyl nitrite and the N-nitroso species reduced with hydrogen over Pd on charcoal or Zn in acetic acid. The amino group may be protected as the benzhydryl carbamate by the method of Hiskey and Adams or as the Boc carbamate using ditertbutyl dicarbonate. The alcohol is activated for coupling as the carbonate by reaction with bis-(p-nitrophenyl) carbonate to give 7.10 (X=p-nitrophenyl, Xi=β-N4-benzoylcytosin-1-yl). Other activated species may be prepared using thiocarbonyldiimidazole or N,N-dimethylaminophosphoryl chloride as described in the preceeding examples.

2. Alternatively, ribofuranoside 32.1a (Xi=β-N4-benzoylcytosin-1-yl) is reacted with periodate as in the general method for morpholino subunit synthesis, but t-butylcarbazate is substituted for ammonia in the reductive ring closure step to give the 5'-free subunit which may be activated as in the example above.

R. 7.11 (X=OH, Xi=β-uracil-1-yl). The alcohol 32.2b (Xi=β-uracil-1-yl) (1 mol) is treated with an excess of sodium hydride in a DMF/THF mixture. Sodium chloroacetate (1 mol) is added and the solution stirred for 24 hours. The solution is filtered in an inert atmosphere, and excess of triethylammonium hydrochloride in DMF is added, the mixture filtered, and the solvents removed by evaporation. The residue can be chromatographed on silica gel using triethylamine/methanol/chloroform mixtures if the silica is first pre-eluted with 2% triethylamine in chloroform.

S. 7.11 (X=O-p-nitrophenyl, Xi=β-uracil-1-yl).

The acid salt from the previous example is activated by treatment with diisopropylcarbodiimide in dichloromethane containing p-nitrophenol containing 1 equivalent of pyridinium p-toluenesulfonate.

T. 7.12 (X=O-p-nitrophenyl, Xi=β-thymin-1-yl).

1. The subunit 32.2b (Xi=Xi=β-thymin-1-yl) is detrylated using 2% acetic acid in 20% trifluoroethanol/dichloromethane. The resulting secondary amine is reacted with benzyl bromoacetate. The alcohol is converted into the primary amine my the procedure in method 7M. The amine is tritylated by the general procedure, the benzyl ester cleaved by catalytic hydrogenolysis in DMF/ethanol containing trieylamine. The acid is activated by treatment with diisopropylcarbodiimide in dichloromethane containing p-nitrophenol and one equivalent of pyridinium tosylate.

2. Alternatively, ribothymidine (Tronchet) is reacted with periodate as in the general method for morpholino subunit synthesis, but glycine benzyl ester is substituted for ammonia in the reductive ring closure step to give the 5'-free subunit which may be further converted as in the example above.

EXAMPLE 8

Representative Subunits which are Converted to Morpholino Structures during Oligomer Assembly A. 5'-Aminoribofuranosides 8.1.

Ribofuranosides may be converted into their 5'-amino derivatives by reaction with triphenylphosphine, sodium or lithium azide and carbon tetrabromide in DMF (Yamamato), followed by reduction with either triphenyl phosphine/ammonia or with hydrogen over Pd on charcoal.

B. 6'-Aminohexopyranosides 8.4.

Hexopyranosides may be converted into their 6'-amino derivatives by the procedure in Example 8A or by the following procedure. The glycoside is treated with dimethoxytrityl chloride in pyridine to selectively protect the primary alcohol. The remaining hydroxy groups are protected by reaction with t-butyldimethylsilyl chloride in DMF containing imidazole. The dimethoxytrityl group is cleaved by treatment with zinc bromide in nitromethane at room temperature (Köster, et al). The free 6'-alcohol is converted into the 6'-amino derivative by reaction with triphenylphosphine, sodium or lithium azide and carbon tetrabromide in DMF (Yamamato), followed by reduction with either triphenyl phosphine/ammonia or with hydrogen over Pd on charcoal. The silyl groups are removed by treatment with HF/pyridine of tetrabutylammonium fluoride in THF.

C. 5'-O-Aminoribofuranosides 8.2.

Ribofuranosides may be converted into their 5'-O-amino derivatives by the following procedure. The glycoside is treated with dimethoxytrityl chloride in pyridine to selectively protect the primary alcohol. The remaining hydroxy groups are protected by reaction with t-butyldimethylsilyl chloride in DMF containing imidazole. The dimethoxytrityl group is cleaved by treatment with zinc bromide in nitromethane at room temperature (Köster, et al) and the primary alcohol converted into the desired aminoxy species using N-hydroxyphthalimide by the procedure of Vassuer, et al. The silyl groups are removed by treatment with HF/pyridine of tetrabutylammonium fluoride in THF.

D. 5'-O-Aminohexopyranosides 8.5.

May be converted into their 6'-O-amino derivatives by the procedure for the ribofuranosides in Example 8C.

EXAMPLE 9

Coupling Morpholino Subunits to form Representative One-Atom-Length Intersubunit Linkages and Two-Atom-Length Intersubunit Linkages A. General.

Whenever the morpholino nitrogen of a subunit, or the terminal subunit in an oligomer, contains an acid labile group such as the trityl group, deprotection is performed with mild acid. Representative acid mixtures which are suitable include 10% cyanoacetic acid in 4:1 dichloromethane/acetonitrile, 7% formic acid in dichloromethane, and 2.5% cyanoacetic acid in 7:93 trifluoroethanol/dichloromethane. For molecules which contain a Boc or benzhydryl carbamate a 20–50% solution of trifluoroacetic acid in dichloromethane may by employed. The acid is removed by precipitation of the deprotected subunit in ether if the reaction is done in homogeneous solution, or by washing with the appropriate rinse solvent if solid phase methods are employed.

Whenever the morpholino nitrogen of a subunit, or the terminal subunit in an oligomer, contains a base labile group such as the FMOC group, deprotection is performed with mild base. Representative base reagents which are suitable include 1–10% DBU/DMF, 10% N-methylpyrrolidine/DMF, and 2–20% piperidine/DMF. The excess reagent, dibenzofulvene, and derived by products are removed by precipitation of the deprotected subunit in ether if the reaction is done in homogeneous solution, or by washing with the appropriate rinse solvent if solid phase methods are employed. Coupling to a morpholino subunit requires that the morpholino nitrogen be present in the uncharged state.

This may be achieved as follows. A mild base such as triethylamine, diisopropylethylamine, or diisopropylaminoethanol (or its ethers or esters) is employed to neutralize residual charge produced in acidic deprotections and/or to maintain any unreacted morpholino nitrogen in the neutral state during the coupling reaction.

B. Coupling to form amide linkages.

The nitrophenyl ester formed in Example 7C, is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.

C. Coupling to form an amine linkage.

The aldehyde formed in Example 7A is dissolved in methanol, or DMF/methanol mix containing nitrophenol and sodium cyanoborohydride at pH=6.5. This is mixed with the deprotected monomeric or oliogomeric species with an uncharged morpholino nitrogen produced as in Example 9A.

1. Formation of amide linkages. The nitrophenyl ester formed in Example 7G, is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.)

EXAMPLE 10

Method for Conversion of Non-morpholino Subunit to Morpholino Subunit during Oligomer Assembly Oligomer may be assembled by construction of the morpholino ring from a dialdehyde and a primary amine. The coupling is performed as follows. The 5'-aminoribofuranoside or 6'-aminohexopyranoside from Example 8 is protected on the amine with trityl as in the general procedure. The molecule is dissolved or suspended in methanol and treated with periodate as per the general procedure in Examples 1 or 2. To the dialdehyde so formed is added a second 5'-aminoribofuranoside or 6'-aminohexopyranoside followed by sodium cyanoborohydride and the pH is maintained between 4.5 and 6.5.

A particularly advantageous method for the synthesis of oligomers by this method involves fixing the the amino group of the first aminoglycoside to a solid support by a cleavable anchor, as in Example 16 below, and performing the oxidation and reductive amination steps on the solid support.

EXAMPLE 11

Coupling Morpholino Subunits to form Representative Three-atom-length Intersubunit Linkages A. Formation of amide linkages.

The nitrophenyl ester formed in Example 7I, is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.

B. Formation of carbamate linakges.

This linkage is prepared from the nitrophenyl carbonate formed in Example 7J and the morpholino-deprotected subunits/oligomer formed as in Example 9A. The coupling follows the method of Summerton and Weller (U.S. Pat. No. 5,034,506).

C. Formation of sulfamide linkages.

This linkage is prepared from the sulfamoyl chlorides produced in Examples 7M or 7N and the morpholino deprotected subunits/oligomer formed as in Example 9A. The coupling follows the method of Summerton and Weller (U.S. Pat. No. 5,034,506).

D. Formation of phosphorodiamidate linkages.

This linkage is prepared from the phosphoryl chloride produced in Example 7O and the morpholino deprotected subunits/oligomer formed as in Example 9A. The coupling follows the method of Summerton and Weller (U.S. Pat. No. 5,185,444).

EXAMPLE 12

Coupling Morpholino Subunits to form Representative Four-Atom-Length Intersubunit Linkages A. Formation of amide linkages.

1. The nitrophenyl ester formed in Example 7S, is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.

2. The nitrophenyl ester formed in Example 7T, is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.

B. Formation of carbazates.

This linkage is prepared from the nitrophenyl carbonate formed in Example 7Q is dissolved in DMF or NMP (containing 0.2–0.4 molar of an appropriate base, such as methyl diisopropylaminoethyl ether) at a concentration of about 0.2 molar, and mixed with the deprotected monomeric or oliogomeric species with an uncharged morpholino nitrogen produced as in Example 9A.

EXAMPLE 13

Preparation of In-Line Branches

A. From Diethylenetriamine

The triamine is reacted with one equivalent of triamine and the terminally reacted monotritylated species isolated by chromatography on alumina. The diamine is now reacted with FMOC chloride, followed immediately by sulfation in pyridine with the sulfur trioxide/pyridine complex. It should be mentioned that the salts of the sulfamic acids can be easily chromatographed on silica gel using triethylamine/ methanol/chloroform mixtures if the silica is first pre-eluted with 2% triethylamine in chloroform. For activation, ten mmole of the triethylamine salt of sulfated subunit is dissolved in 10 ml of dichloromethane and then 40 mmole of pyridine is added. This solution is chilled for 15 minutes on a bed of dry ice and then 11 mmole of phosgene (20$ in Toluene) is slowly added while the solution is rapidly stirred. After addition the solution is allowed to come to room temperature and then washed with aqueous $NaHCO_3$, dried, and chromatographed on silica gel eluting with a mixture of chloroform and acetone to give the desired sulfamoyl chloride. The sulfamate can be coupled to an amino group or morpholino amine in the same fashion in which an activated subunit may be coupled (Examples 9–12). Following incorporation of the branching subunit, cleavage of the trityl group allows construction of the oligomeric branches by sequential coupling of subunits. When the first branch is complete is capped and the molecule treated with 10% DBU/DMF to remove the FMOC group. The second branch may now be synthesized using by sequential coupling of subunits.

B. From 1,3-Diamino-2-Hydroxypropane

The diamine is dissolved in DMF and treated with one equivalent of trityl chloride. The monotritylated species is separated by chromatography on silica gel and then reacted with FMOC chloride to protect the remaining amino group. The alcohol is reacted with bis(p-nitrophenyl carbonate) in DMF containing triethylamine to produce the activated carbonate. The carbonate can be coupled to an amino group or morpholino amine in the same fashion in which an activated subunit may be coupled (Example 9–12). Following incorporation of the branching subunit, cleavage of the trityl group allows construction of the oligomeric branch by sequential coupling of subunits. When the first branch is complete, it is capped and the molecule treated with 10% DBU/DMF to remove the FMOC group. The second branch may now be synthesized using by sequential coupling of subunits.

EXAMPLE 14

Preparation of Hub Branches

A. Using 1,3,5-Benzenetricarboxylic acid amides.

One mmol of 1,3,5-benzenetricarbonyl chloride in pyridine is reacted with 1 mmol of o-nitrobenzyl alcohol, followed by 1 mmol of p-nitrophenethyl alcohol, and the reaction quencehed with piperidine. The desired species containing one o-nitrobenzyl ester and one p-nitrophenethyl ester is isolated by chromatography on silica gel. The free piperazine is coupled to activated subunits prepared in Example 7 using the methods in Examples 9–12. After the coupling, the product is purified on silica gel. Additional subunits may be introduced by detrityalation and repetition of the coupling. Following introduction of the final subunit, the chain is detritylated and capped with acetic anhydride. The nitrophenethyl ester is cleaved by treatment with 10% DBU/DMF. The free acid is coupled with N-trityl piperazine prepared below using diisopropylcarbodiimide in dichloromethane. Sububits may be introduced by detrytilation and coupling as above. When this chain is finished it is capped with acetic anhydride.

The o-nitrobenzyl ester is cleaved by irradiation with 320 nm light. Following coupling with N-trityl piperazine as above, sububits may be introduced by detrytilation and coupling as above.

B. Using 1,3,5-Benzenetricarboxylic acid.

One mmol of 1,3,5-benzenetricarbonyl chloride in pyridine is reacted with 1 mmol of o-nitrobenzyl alcohol, followed by 1 mmol of p-nitrophenethyl alcohol, and the reaction quenceched with water. The desired species containing one o-nitrobenzyl ester and one p-nitrophenethyl ester is isolated by chromatography on silica gel. The free acid is coupled to subunits or preformed oligomers, at the free morpholino nitrogen (produced by detrytilation and neutralization as described in Example 9), using diisopropylcarbodiimide in dichloromethane. The nitrophenethyl ester is cleaved by treatment with 10% DBU/DMF. The free acid is coupled to subunits or preformed oligomers, at the free morpholino nitrogen, coupled with using diisopropylcarbodiimide in dichloromethane. The o-nitrobenzyl ester is cleaved by irradiation with 320 nm light. The free acid is coupled to subunits or preformed oligomers, at the free morpholino nitrogen, using diisopropylcarbodiimide in dichloromethane. It should be recognized that the acid may be employed in solid phase synthesis by coupling to a growing chain on a solid support. The two esters which may each be selectively deprotected are reacted sequentially with subunits or oligomers.

C. From piperazine.

N-tritylpiperazine is reacted with FMOC chloride. The trityl group is removed by the method in Example 9, and the free piperazine nitrogen reacted with an activated subunit by the method above. As many subunits as desired may be introduced by the method in Example 14A above. Following end capping of this chain, the FMOC group is cleaved using 10% DBU/DMF. The free piperazine nitrogen is reacted with an activated subunit by the method above. As many subunits as desired may be introduced by the method in Example 14A above.

EXAMPLE 15

Joining Two Ends of an Oligomer by Covalent Linkage

Two chains of a divergent branch are constructed so as to place subunits with $Xi=[CH_2]_n$-SS-ethyl at the termini. The disulfide is cleaved using dithiothreitol in mildy basic aqueous solution. The oligomeric dithiol is separated from the reagents by passage over a column of chromatographic grade polypropylene and eluting with an acetonitrile in dilute aqueous acetic acid. The dilute solution is neutralized to pH=8, and treated with iodine to produce the disulfide.

EXAMPLE 16

Preparation of Oligomer Library on a Solid Support

A. Solid support

The following supports are suitable for solid phase synthesis of oligomers: aminomethyl polystyrene resin, 1% divinylbenzene crosslinked, 200–400 mesh, 0.5–1.5 mmoles N per gram (Sigma Chemical CO. A1160); polystyrene resin, 1% divinylbenzene crosslinked, grafted with polyethylene glycol, primary amino terminated, 0.1–0.3 mmoles N per gram (TentaGel, Rapp Polymere, Germany); custom-synthesized macroporous polystyrene, 8% divinylbenzene crosslinked, functionalized with 1,12-diaminododecane, with particle sizes in the range of 50–80 microns in diameter, and with pore sizes approximately 700 Å.

B. Construction of anchors

The following anchors are employed for solid phase oligomer synthesis:

1. 10 mmol of bis[2-(succinimidooxycarbonyloxy)ethyl] sulfone (Pierce, Rockford Ill.) is treated with 5 mmol of momotritylpiperazine (made as in the example below) and the product purified by silica chromatography or crystallization.

2. 2,2'-Thiodiethanol is treated with an equimolar amount of bis(p-nitrophenyl) carbonate in DMF containing triethylamine. The monoesterified species is purified by chromatography and reacted with an excess of monotritylpiperazine, formed by adding trityl chloride to a solution of excess piperazine in DMF. This is converted to the nitrophenyl carbonate with a slight excess of as above bis(p-nitrophenyl) carbonate in DMF containing triethylamine.

3. 4-Hydroxymethyl-3-nitrobenzoic acid (Knieb-Cordonier, et al) is esterifed with methanol and diisopropylcarbodiimide in dichloromethane. The alcohol is converted into the p-nitrophenylcarbonate by the method above and reacted with monotritylpiperazine. The ester is cleaved by saponification and converted into the p-nitrophenyl ester by treatment with p-nitrophenol and diisopropylcarbodiimide in dichloromethane.

C. Construction of tethers.

Polyethylene glycol 4600 is converted into its mono-p-nitrophenyl carbonate by reaction of 10 mmol of the PEG with 1 mmol of bis(p-nitrophenyl) carbonate in DMF containing triethylamine. To the solution is add an excess of piperazine and the excess reagents thoroughly removed by evaporation. The mixture is taken up in water, acidified and the amine is purified from the neutral PEG chains by ion exchange chromatography on Dowex-50. The amine is converted into the N-trityl species by the standard procedure and then the alcohol is converted to the nitrophenyl carbonate with a slight excess of bis(p-nitrophenyl) carbonate in DMF containing triethylamine.

D. Configuration of the particle for oligomer assembly

1. Atttachment of the tether. The solid support is placed in a column such as the 2 mL polypropylene Biorad Bio-Spin Disposable Chromatography Column, cat #732-6008, whose frit has been replaced with a new frit (Isolab Quik-Sep Disc # D-4301). The resin is treated with DMF for 1–12 hours, during which time it is placed in a aspirator vacuum to remove trapped air, and gently agitated to break up clumps. The tether is dissolved in DMF or NMP (containing 0.2–0.4 molar of an appropriate base, such as triethylamine) at a concentration of about 0.05 molar and added to the support. Sufficient tether is added so as to react 5– 50% of the free amines on the resin surface. After 12–48 hours at 45 degrees C. the solvents are drained and the resin washed with DMF.

2. Capping with dansyl chloride. The resin from the previous example is washed with dichloromethane and treated with a solution of 0.2 molar dansyl chloride in 20% tetramethylene sulfone in dichloromethane containing 0.4 molar of an appropriate amine such as diisopropylethylamine. After 30 minutes at room temperature the resin is drained and washed with DMF.

3. Attachment of the anchor. The trityl group is removed from the end of the tether by three washings with 2% dichloroacetic acid in dichloromethane. The resin is washed with dichloromethane, then 5% diisopropylethylamine in dichloromethane. The anchor is dissolved in DMF or NMP (containing 0.2–0.4 molar of an appropriate base, such as methyl diisopropylaminoethyl ether) at a concentration of about 0.2 molar, and mixed with the resin containing the deprotected tether for 2–48 hours at room temperature. The resin is thoroughly washed with DMF.

E. Solid phase synthesis of oligomers for solution phase testing.

1. Coupling to produce an oligomer with only morpholino backbone type. Aminomethyl polystyrene resin is loaded with the anchor from Example 16B1 to achieve about 350 umol of trityl species per gram resin. The following cycle is repeated. Suitable washes of dichloromethane, 25% isopropanol/dichlromethane, or DMF are incorporated between the steps to remove excess reagents and reaction byproducts.

a. The protecting group is removed by an acidic reagent from Example 9A.
   b. The resin is neutralized with 5–20% diisopropylethylamine in dichloromethane.
   c. A mixture of activated subunits prepared in Example 7 is coupled to the end of the growing chain by the procedures defined in Examples 9–12. It is critical, in order to achieve roughly equimolar amounts of the individual oligomers, that the concentrations of each activated subunit in the reaction be adjusted so that the rate of coupling for each subunit will be as nearly the same as possible. The coupling rates for the activated subunit are determined in solution, by reaction with a monomeric morpholino subunit. The appearance of coupling product as a function of time monitored by HPLC. A rate constant is calculated and used to adjust the concentrations in the coupling mixture so that the rate of incorporation of each activated species in the mixture is the same.

2. Preparation of a mixed backbone oligomer. The method of Example 16E1 is employed, but activated subunits other than morpholino species are employed. For example, Boc-alanine may be converted into is p-nitrophenyl ester using diisopropylcarbodiimide in dichloromethane. It is used as an activated subunit in the repetitive steps outlined in the method of example 16E1. The oligomer so produced has a mixed morpholino-peptide backbone.

F. Deprotection of the oligomers.

Deprotection of the functional groups on the side chains is acheived as follows. Silylated groups are removed by treatment with either t-butylammonium fluoride in THF or pyridinium/HF complex in pyridine. Amides may be cleaved by ammonolysis with 2:1 conc ammonia/DMF. Phenylsulfonyl or FMOC carbamates are cleaved DBU/DMF treatment. Disulfides are converted into thiols by treatment with mercaptoethanol or dithiothreitol in DMF or water containing triethylamine.

EXAMPLE 17

Solid Phase Synthesis of Oligomers for Oligomer Family Testing Methods

The method of Example 16E1 is employed with the following differences. A macroporous resin is treated with tether, then anchor. Two additional steps, a and e below, are incorporated into each cycle to produce the following sequence:

a. The resin is distributed, in equal portions, into a number of synthesis columns that is the same as the number of subunits species desired to couple in step e.
   b. The protecting group is removed by an acidic reagent from Example 9A.
   c. The resin is neutralized with 5–20% diisopropylethylamine in dichloromethane.
   d. Only a single activated subunit species is coupled in each column.
   e. The resin is recombined.

For example, to prepare an oligomer family which consists of activated subunits derived from the following set of subunits:

1. 32.2b (Xi=β-methyl)
   2. 32.2b (Xi=β-uracil-1-yl)
   3. 32.2b (Xi=β-N4-benzoylcytosin-1-yl)
   4. 32.2b (Xi=β-N6-benzoyladenin-1-l)
   5. 32.2b (Xi=β-N2-phenylacetylguanin-1-yl)

requires that following incorporation of the anchor onto the resin, the macroporous resin is divided into five equal portions and placed in five columns (Example 16D1) suitable for solid phase synthesis.

The synthesis cycle is then preformed with each column receiving a single activated subunit species (prepared by the methods in Example 7, from the subunits in the list above) for the coupling step. When the coupling step is finished, the resin is recombined and distributed into five new solid phase synthesis columns for the second synthesis cycle, where again, each column recieves a single activated subunit species.

2. Incorporation of truncated species into the oligomer family.

a. By use of partially pre-capped subunits. The five subunits species from Example 16F1 are converted into their acetamides or trifluoroacetamides by removal of the trityl protecting group and reaction with either 5% acetic anhydride and 5% triethylamine in DMF for 5 minutes or with p-nitrophenyl trifluoroacetate in DMF.

These are then individually activated by the methods in Example 7 and individually mixed with the corresponding activated, but still tritylated, subunits with the same Xi group. The correct proportion of capped to tritylated subunits for a given synthesis cycle in the construction of a hexamer is given in Table 1. The synthesis is then performed exactly as described in Example 16F1 with these five mixtures of capped and tritylated activated subunit species.

b. By capping during the synthesis. After the deprotection step of each coupling cycle, the resin containing the detritylated chain is treated with 7% formic acid in dichloromethane. The extent of formylation is controlled by the length of the treatment. For example, to achieve a 2.5% conversion to formylated chains requires one hour with this reagent. As an alternative, the cleavage of trityl may be done with formic acid/dichloromethane mixtures as described in example 9A. Instead of immediately washing the resin after detritylation, to remove the acidic reagent, the reaction is continued to promote the formylation of the morpholino nitrogen.

EXAMPLE 18

Determination of Oligomer Sequence

A. Removal of oligomers from a Selected Bead

The treament necessary to remove the oligomer from the resin depends on the anchor:

1. Anchor from 16B1 is cleaved by treatment with 10% DBU/DMF.
   2. Anchor from 16B2 is cleaved by treatment with mercaptoethanol or dithiothreitol in DMF or water containing triethylamine.
   3. Anchor from 16B3 is cleaved by iradiation of the resin with light of 350 nm. Wavelengths shorter than 300 nm are are excluded by a pyrex filter.

B. Analysis of the oligomer by mass spectrometry.

A single bead, containing an oligomer family, and sorted by the procedures described above, is washed by the methods described above to remove protein. The anchor is then cleaved by the method in Example 16H using 2 uL of reaction solution. The reaction mixture is combined with a mixture of sinapinic acid and aqueous acetonitrile (4 parts). The solution is then introduced onto the probe of a Matrix Assisted Laser Desorption Time Of Flight (MALDE-TOF) mass spectrometer. The composition and sequence of the oligomer is determined by the molecular weights of the peaks of the full-length molecule and the truncated species.

EXAMPLE 19

Density Gradient Separation of Oligomer-Library Particles

Libraries of oligomers are formed on the particles in accordance with the examples above. The oligomer-particles preferably contain an intense dye or fluorescent material to facilitate visualization of individual particles. Each particles is preferably prepared to contain a single family of N-subunit oligomer species, and together the collection of particles in a given preparation contain the full library of oligomer species.

To utilize such a library of oligomer-particles for detection of target binding by one or more component oligomer species and for determining the sequence of an oligomer family containing an oligomer which exhibits said target binding, the oligomer-particle library preparation is mixed with a suitable concentration of target in a solution having a density greater than that of the oligomer-particle, but less than that of an oligomer-particle/target complex. Sucrose solutions are generally convenient for this purpose. After gentle mixing for a period of time sufficient to allow binding of target to any particle-bound oligomer which has a suitable affinity for said target, the solution is allowed to stand for a period of time, whereupon any oligomer-particle/target complex which forms will settle to the bottom of the container. If the particles are quite small (eg., 20 to 30 microns in diameter) or the buoyant density differential between the solution and the oligomer-particle/target is small, then centrifugation can be used to speed the settling of complexed particles.

Alternatively, the oligomer-particle preparation is mixed with a suitable concentration of target in a solution containing a density-gradient-forming component, such as metrizamide, Centrifugation in an ultracentrifuge then generally rapidly separates oligomer-particles from any oligomer-particle/target complex which may have formed.

Although the invention has been described with reference to specifc synthetic, and sequencing methods, it will be appreciated that various changes and modification can be made without departing from the invention.

It is claimed:

1. A combinatorial library of oligomers, each formed of at least four linked morpholino subunits of the form:

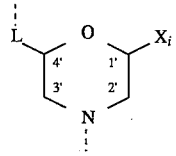

in which (i) morpholino subunit structures are linked together by linkages L one to four atoms long joining the morpholino nitrogen of one subunit to the 4' cyclic carbon of an adjacent subunit, (ii) $X_i$ is a side chain in subunit i in each oligomer of the library, (iii) the different oligomers in the library have different sequences of side chains in at least three subunit positions, (iv) $X_i$ is selected from the group consisting of purines, pyrimidines, non-nucleobase aromatic side chains, aliphatic side chains, and mixed aromatic/aliphatic moieties, and (v) said library contains at least 1,000 different side chain sequence oligomers.

2. The composition of claim 1, wherein oligomer linkages in the library include one-atom linkages of the form:

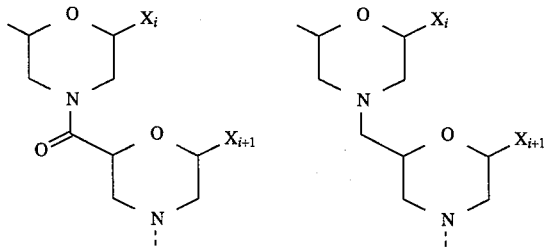

where $X_{i+1}$ is a side chain in a subunit adjacent subunit i.

3. The composition of claim 1, wherein oligomer linkages in the library include carbonyl-containing linkages of the form:

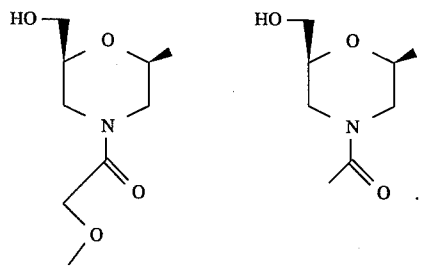

4. The composition of claim 1, wherein an oligomer in the library includes side chains selected from the group consisting of purines and pyrimidines, and side chains selected from the group consisting of a non-nucleobase aromatic moieties, aliphatic moieties, and mixed aromatic/aliphatic moieties.

5. The composition of claim 1, wherein said oligomers are effective to hybridize, by Watson-Crick base pairing to random-sequence oligonucleotides.

6. The composition of claim 1, wherein said oligomers have different sequences of linkages.

7. The composition of claim 1, wherein the linkages are selected from the group consisting of 3-atom carbamate and 3-atom phosphorodiamidate.

8. The composition of claim 1, wherein the oligomers include an oligomer having one or more morpholino subunit structures that are covalently attached to a linkage that itself directly links two additional morpholino subunit structures in the oligomer.

9. The composition of claim 1, wherein the combinatorial library is formed on a plurality of particles, each particle having a surface coating of oligomer molecules of the same sequence.

10. The composition of claim 9, wherein the oligomer molecules on each particle are carried on dendritic polymers attached to the particles and coupled to the oligomer molecules through cleavable linkages.

11. The composition of claim 9, wherein the particles are macroreticular particles having selected sizes in the 40–200 μm range, and the oligomer molecules are coupled to the particles through cleavable linkages.

12. A composition of oligomers, each formed of at least four linked morpholino subunits of the form:

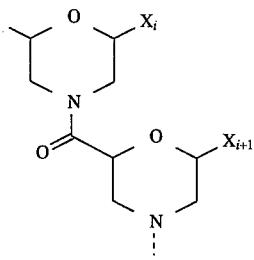 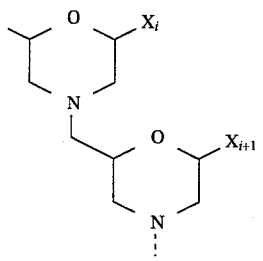

in which (i) morpholino subunit structures are linked together by one-atom linkages joining the morpholino nitrogen of one subunit to the 4' cyclic carbon of an adjacent subunit, (ii) $X_i$ is a side chain in subunit i in each oligomer of the composition, (iii) the different oligomers in the composition have different sequences of side chains in at least three subunit positions, and (iv) $X_i$ is selected from the group consisting of purines, pyrimidines, non-nucleobase aromatic side chains, aliphatic side chains, and mixed aromatic/aliphatic moieties.

13. A composition of oligomers, each formed of at least four linked morpholino subunits of the form:

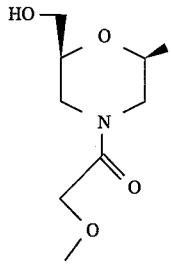 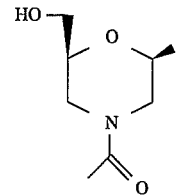

in which (i) morpholino structures are linked together by carbanoyl-containing linkages joining the morpholino nitrogen of one subunit to the 4' cyclic carbon of an adjacent subunit, (ii) $X_i$ is a side chain in subunit i in each oligomer of the composition, (iii) the different oligomers in the composition have different sequences of side chains in at least three subunit positions, and (iv) $X_i$ is selected from the group consisting of purines, pyrimidines, non-nucleobase aromatic side chains, aliphatic side chains, and mixed aromatic/aliphatic moieties.

14. The composition of claim 13, wherein $X_i$ is a purine or pyrimidine Watson-Crick base-pairing moiety.

* * * * *